US012239629B2

(12) United States Patent
Tran

(10) Patent No.: US 12,239,629 B2
(45) Date of Patent: Mar. 4, 2025

(54) METHODS FOR THE PROPHYLAXIS AND TREATMENT OF COVID AND COVID-19

(71) Applicant: Lloyd Hung Loi Tran, San Jose, CA (US)

(72) Inventor: Lloyd Hung Loi Tran, San Jose, CA (US)

(*) Notice: Subject to any disclaimer, the term of this patent is extended or adjusted under 35 U.S.C. 154(b) by 0 days.

(21) Appl. No.: 18/047,432

(22) Filed: Oct. 18, 2022

(65) Prior Publication Data

US 2023/0172902 A1 Jun. 8, 2023

Related U.S. Application Data

(63) Continuation-in-part of application No. PCT/US2021/027848, filed on Apr. 17, 2021.

(60) Provisional application No. 63/012,432, filed on Apr. 20, 2020, provisional application No. 63/018,768, filed on May 1, 2020, provisional application No. 63/032,116, filed on May 29, 2020, provisional application No. 63/037,373, filed on Jun. 10, 2020, provisional application No. 63/041,812, filed on Jun. 19, 2020, provisional application No. 63/170,350, filed on Apr. 2, 2021.

(51) Int. Cl.

| | | |
|---|---|---|
| A61K 31/357 | (2006.01) | |
| A61K 9/51 | (2006.01) | |
| A61K 31/27 | (2006.01) | |
| A61K 31/41 | (2006.01) | |
| A61K 31/445 | (2006.01) | |
| A61K 31/4706 | (2006.01) | |
| A61K 31/4725 | (2006.01) | |
| A61K 31/4985 | (2006.01) | |
| A61K 31/536 | (2006.01) | |
| A61K 31/573 | (2006.01) | |
| A61K 31/675 | (2006.01) | |
| A61K 38/05 | (2006.01) | |
| A61K 39/00 | (2006.01) | |
| A61K 39/13 | (2006.01) | |
| A61P 31/14 | (2006.01) | |

(52) U.S. Cl.
CPC .......... *A61K 31/357* (2013.01); *A61K 9/5161* (2013.01); *A61K 31/27* (2013.01); *A61K 31/41* (2013.01); *A61K 31/445* (2013.01); *A61K 31/4706* (2013.01); *A61K 31/4725* (2013.01); *A61K 31/4985* (2013.01); *A61K 31/536* (2013.01); *A61K 31/573* (2013.01); *A61K 31/675* (2013.01); *A61K 38/05* (2013.01); *A61K 39/13* (2013.01); *A61P 31/14* (2018.01); *A61K 2039/545* (2013.01)

(58) Field of Classification Search
CPC .... A61K 31/357; A61K 9/5161; A61K 31/27; A61K 31/41; A61K 31/445; A61K 31/4706; A61K 31/4725; A61K 31/4985; A61K 31/536; A61K 31/573; A61K 31/675; A61K 38/05; A61P 31/14
See application file for complete search history.

(56) References Cited

U.S. PATENT DOCUMENTS

| 7,232,798 B2 | 6/2007 | Tran |
| 10,980,756 B1 | 4/2021 | Glick |
| 11,090,303 B2 | 8/2021 | Tran |
| 11,162,080 B2 | 11/2021 | Wimmer |
| 2003/0109531 A1 | 6/2003 | Tran |
| 2007/0244039 A1 | 6/2007 | Tran |

FOREIGN PATENT DOCUMENTS

| WO | WO 2003/039487 | 5/2003 |
| WO | WO 2019/222339 | 11/2019 |
| WO | WO 2021/216385 | 10/2021 |

OTHER PUBLICATIONS

Koftis et al. "COVID-19: ICU delirium management during SARS-CoV-2 pandemic", Crit Care. Apr. 28, 2020;24(1):176. (Year: 2020).*
Dasuri et al. "Dietary and donepezil modulation of mTOR signaling and neuroinflammation in the brain", Biochim Biophys Acta. Feb. 2016; 1862(2): 274-283 (Year: 2016).*
Garg et al. "Current Advances in Chitosan Nanoparticles Based Drug Delivery and Targeting", Adv Pharm Bull. Jun. 2019; 9(2): 195-204 (Year: 2019).*
D'Alessandro et al. "The Use of Antimalarial Drugs against Viral Infection", Microorganisms. Jan. 2020; 8(1): 85 (Year: 2020).*
Beck et al. "Predicting commercially available antiviral drugs that may act on the novel coronavirus (SARS-CoV-2) through a drug-target interaction deep learning model", Comput Struct Biotechnol J. Mar. 30, 2020;18:784-790 (Year: 2020).*

(Continued)

*Primary Examiner* — Amy E Juedes
*Assistant Examiner* — Peter Johansen
(74) *Attorney, Agent, or Firm* — David R. Preston

(57) ABSTRACT

The present invention recognizes that there is a need for the prophylaxis or treatment of COVID and COVID-19. A first aspect of the present invention generally relates to methods of prophylaxis or treatment of COVID or COVID-19 using various pharmaceutical compositions. A second aspect of the present invention generally relates to methods of prophylaxis or treatment of COVID or COVID-19 using combinations of antimalarial drugs and antiviral drugs. A third aspect of the present invention generally relates to methods of prophylaxis or treatment of COVID or COVID-19 using nanoparticle formulations that include pharmaceutical compositions. A fourth aspect of the present invention generally relates to methods of prophylaxis or treatment of COVID or COVID-19 using combinations of various pharmaceutical compositions. A fifth aspect of the present invention generally relates to methods of prophylaxis or treatment of COVID or COVID-19 using a polio vaccine and pharmaceutical compositions.

58 Claims, 37 Drawing Sheets

(56) References Cited

OTHER PUBLICATIONS

WO 2021/216385 International Search Report and Written Opinion, Sep. 2021, PCT.

WO 2021/216385 International Preliminary Report on Patentability, Nov. 2022, PCT.

Liu, Y.; Yang, Y.; Zhang, C.; Huang, F.; Wang, F.; Yuan, J.; Wang, Z.; Li, J.; Feng, C.; Zhang, Z.; et al. Clinical and biochemical indexes from 2019-nCoV infected patients linked to viral loads and lung injury. Sci. China Life Sci. 2020, 63, 364-374.

D'Alessandro et al., "The Use of Antimalarial Drugs Against Viral Infection," Microorganisms, vol. 8:85 (pp. 1-26), Jan. 8, 2020.

Grein et al., "Compassionate Use of Remdesivir for Patients With Severe COVID-19," The New England Journal of Medicine382:24 (pp. 2327-2336, Jun. 11, 2020.

Dorothy H.J. Cheong, Daniel W.S. Tan, Fred W.S. Wong, Thai Tran, Anti-malarial drug, artemisinin and its derivatives for the treatment of respiratory diseases, Pharmacological Research, vol. 158, 2020, 104901, ISSN 1043-6618, https://doi.org/10.1016/j.phrs.2020.104901.

Fintelman-Rodrigues N, Sacramento CQ, Ribeiro Lima C, Souza da Silva F, Ferreira AC, Mattos M, de Freitas CS, Cardoso Soares V, da Silva Gomes Dias S, Temerozo JR, Miranda MD, Matos AR, Bozza FA, Carels N, Alves CR, Siqueira MM, Bozza PT, Souza TML. Atazanavir, Alone or in Combination with Ritonavir, Inhibits SARS-CoV-2 Replication and Proinflammatory Cytokine Production. Antimicrob Agents Chemother. Sep. 21, 2020;64(10):e00825-20. doi: 10.1128/AAC.00825-20. PMID: 32759267; PMCID: PMC7508582.

Cho, J., Lee, Y.J., Kim, J. et al. Antiviral activity of digoxin and ouabain against SARS-CoV-2 infection and its implication for COVID-19. Sci Rep 10, 16200 (2020). https://doi.org/10.1038/s41598-020-72879-7.

Mukaetova-Ladinska EB, Kronenberg G, Raha-Chowdhury R. COVID-19 and neurocognitive disorders. Curr Opin Psychiatry. Mar. 1, 2021;34(2):149-156. doi: 10.1097/YCO.0000000000000687. PMID: 33395101; PMCID: PMC7924920.

Hasanagic S, Serdarevic F. Potential role of memantine in the prevention and treatment of COVID-19: its antagonism of nicotinic acetylcholine receptors and beyond. Eur Respir J. Aug. 13, 2020;56(2):2001610. doi: 10.1183/13993003.01610-2020. PMID: 32554535; PMCID: PMC7301831.

Naughton SX, Raval U, Pasinetti GM. Potential Novel Role of COVID-19 in Alzheimer's Disease and Preventative Mitigation Strategies. J Alzheimers Dis. 2020;76(1):21-25. doi: 10.3233/JAD-200537. PMID: 32538855; PMCID: PMC8057202.

Ahmad F. COVID-19 induced ARDS, and the use of galantamine to activate the cholinergic anti-inflammatory pathway. Med Hypotheses. Dec. 2020;145:110331. doi: 10.1016/j.mehy.2020.110331. Epub Oct. 6, 2020. PMID: 33038588; PMCID: PMC7536172.

Capone F, Motolese F, Luce T, Rossi M, Magliozzi A, Di Lazzaro V. COVID-19 in teriflunomide-treated patients with multiple sclerosis: A case report and literature review. Mult Scler Relat Disord. Feb. 2021;48:102734. doi: 10.1016/j.msard.2020.102734. Epub Jan. 2, 2021. PMID: 33429305; PMCID: PMC7836732.

Yagovkina NV, Zheleznov LM, Subbotina KA, Tsaan AA, Kozlovskaya LI, Gordeychuk IV, Korduban AK, Ivin YY, Kovpak AA, Piniaeva AN, Shishova AA, Shustova EY, Khapchaev YK, Karganova GG, Siniugina AA, Pomaskina TV, Erovichenkov AA, Chumakov K, Ishmukhametov AA. Vaccination With Oral Polio Vaccine Reduces COVID-19 Incidence. Front Immunol. May 30, 2022;13:907341. doi: 10.3389/fimmu.2022.907341. PMID: 35711442; PMCID: PMC9196174.

Aghagoli, G., Murphy, S.A., et al., "Neurological Involvement in COVID-19 and Potential Mechanisms: A Review", *Neurocrit Care*, 2021, 34, pp. 1062-1071 (published online on Jul. 13, 2020).

Arbour, N., Talbot,P. J., et al., "Neuroinvasion by human respiratory coronaviruses", *Journal of Virology*, 2000, pp. 8913-8921. Mentions human coronaviruses (HCoV) 229E and OC43 (Jul. 10, 2001).

Biomed Industries, Inc., "A Phase 3 Randomized Double Blind Efficacy and Safety Study of Oral Polio Vaccine and NA-831 for Covid-19 (OPV-NA831)", details of proposed clinical study, published at ClinicalTrials.gov (Sep. 9, 2020).

Biomed Industries, Inc., Press Releases released by Biomed Industries, Inc. and/or by NeuroActiva Inc. (pp. 1-2 + pp. 7-13). (Sep. 4, 2020, Jul. 21, 2020, Dec. 6, 2019 and Jul. 14, 2019).

Cao, R., Hu, Z., Wang, M, Zhong, W., et al., "Anti-SARS-COV-2 potential of artemisinins in vitro", *ACS Infectious Diseases*, 2020, vol. 6, No. 9, pp. 2524-2531 (published online on Jul. 31, 2020).

Cimolai, N. "Potentially repurposing adamantanes for COVID-19", *Journal of Medical Virology*, 2020, DOI: 10.1002/jmv.25752 (published online on Mar. 16, 2020 (source: PubMed, https://pubmed.ncbi.nlm.nih.gov/32176361/)).

Cheng, J., Zhang, G., et al., "The S2 Subunit of QX-type Infectious Bronchitis Coronavirus Spike Protein Is an Essential Determinant of Neurotropism", *Viruses*, 11, 972, doi: 10.3390/v11100972 (Oct. 22, 2019).

Cortés Borra, A. "Does amantadine have a protective effect against COVID-19?", *Neurologia i Neurochirurgia Polska (Polish Journal of Neurology and Neurosurgery)*, 2020, vol. 54, No. 3, pp. 284-285 (published online on Jun. 4, 2020 (source: PubMed, https://pubmed.ncbi.nlm.nih.gov/32495926/)).

European Medicines Agency (EMA) Press Release, "EMA provides recommendations on compassionate use of remdesivir for COVID-19" (Apr. 3, 2024).

European Medical Agency (EMA) "Summary on Compassionate Use—Remdesivir Gilead—International non-proprietary name: remdesivir"; Procedure No. EMEA/H/K/005622/CU; Human Medicines Division, document EMA/178637/2020—Rev.2 *. See p. 6: "Remdesivir when used as part of a compassionate use programme, is indicated for the treatment of adults with coronavirus disease 2019 (COVID-19) who require invasive mechanical ventilation" (published Apr. 3, 2020).

European Search Opinion from the European Patent Office (EPO) dEuropean patent application No. 21793162.5, derived from PCT/US2021/027848; and the accompanying covering letter from EPO (dated and sent Oct. 1, 2024).

Fehr, A.R., and Perlman, S. "Coronaviruses: An overview of their replication and pathogenesis", *Methods in Molecular Biology*, vol. 1282, DOI 10.1007/978-1-4939-2438-7_1 (2015).

Foley and Leutenegger, "A review of coronavirus infection in the central nervous system of cats and mice", *J Vet. Intern. Med.*, 2001, 15, pp. 438-444. Mentions for example feline infectious peritonitis (FIPV) and mouse hepatitis virus (MHV) (Feb. 28, 2001).

Gendrot, M., Pradines, B et al., "Antimalarial artemisinin-based combination therapies (ACT) and COVID-19 in Africa: In vitro inhibition of SARS-COV-2 replication by mefloquine-artesunate", *International Journal of Infectious Diseases*, 2020, 99, pp. 437-440 (published online on Aug. 14, 2020 (source: Pub Med, https://pubmed.ncbi.nlm.nih.gov/32805422/)).

Jung, K., Saif, L.J., and Wang, Q. "Porcine epidemic diarrhea virus (PEDV); An update on etiology, transmission, pathogenesis, and prevention and control", *Virus Research*, 2020, 286, 198045 (13 pages) (published online on Jun. 2, 2020).

Li, Y.-C. Bai, W.-Z, and Hashikawa, T. "The neuroinvasive potential of SARS-COV2 may play a role in the respiratory failure of COVID-19 patients", *Journal of Medical Virology*, Jun. 2020; 92(6); pp. 552-555 (Original version published online on Mar. 11, 2020 (source: PubMed, https://pubmed.ncbi.nlm.nih.gov/32104-915/); corrected version published online after Mar. 17, 2020).

Malik, Y.A. "Properties of Coronavirus and SARS-COV-2", *Malaysian J. Pathol.*, 42(1), pp. 3-11 (Apr. 2020).

Mora-Diaz, J.C., Gimenez-Lirola, L.G., et al., "Porcine Hemagglutinating Encephalomyelitis Virus (Phev): A Review", *Frontiers in Veterinary Science*, vol. 6, article 53 (12 pages). doi: 10.3389/fvets.2019.00053 (Feb. 27, 2019).

Ochani, R.K., Surani, S., et al., "COVID-19 pandemic: from origins to outcomes. A comprehensive review of viral pathogenesis, clinical manifestations, diagnostic evaluation, and management", *Le Infezioni in Medicina*, 2021, vol. 29, No. 1, pp. 20-36 (in English) (published online on Mar. 1, 2021 (source: PubMed, https://pubmed.ncbi.nlm.nih.gov/33664170/)).

Partial European Search Report and Provisional Opinion from the European Patent Office (EPO) European patent application No.

(56) References Cited

OTHER PUBLICATIONS 21793162.5, derived from PCT/US2021/027848; and the accompanying covering letter from EPO (dated Apr. 30, 2024).

Patel, A.B, and Verma, A. "COVID-19 and Angiotensin-Converting Enzyme Inhibitors and Angiotensin Receptor Blockers - What Is the Evidence?", *Journal of the American Medical Association (JAMA)*, vol. 323, No. 18, pp. 1769-1770 (May 12, 2020 published online Mar. 23, 2020).
Płusa, T. "Anti-inflammatory effects of amantidine and memantine in SARS-COV-2 infection", *Pol. Merkur Lekarski (Polish Medical Journal*) 49(289), pp. 67-70; abstract only (Feb. 24, 2021).
Popov, D. "Treatment of Covid-19 infection. A rationale for current and future pharmacological approach" (Review article), *EC Pulmonology and Respiratory Medicine*, 2020, vol. 9, issue 4, pp. 38-58 (published on Mar. 23, 2020).
Regla-Nava, "The replication of a mouse adapted SARS-COV in a mouse cell line stably expressing the murine SARS-COV receptor mACE2 efficiently induces the expression of proinflammatory cytokines", *Journal of Virological Methods*, 193, pp. 639-646 (Aug. 1, 2013).
Rejdak, K. and Grieb, P. "Adamantanes might be protective from COVID-19 in patients with neurological diseases: multiple sclerosis, parkinsonism and cognitive impairment—Case report", *Multiple Sclerosis and Related Disorders*, 2020, 42, pp. 10263-10264. (published online on Apr. 30, 2020).
Roberts, A., Subbarao, K. et al., "Mouse-adapted Sars-Cov MA15 causes disease+ mortality in BALB-c mice +is in mouse brain", PloS Pathogens, vol. 3, issue 1, e5 (pp. 0023-0037) doi: 10.1371/journal.ppat.0030005 (Jan. 12, 2007).
Sanders, J.M., Monogue, M.L., Jodlowski T.Z. and Cutrell, J.B. "Pharmacologie Treatments for Coronavirus Disease 2019 (COVID-19)—A Review", *Journal of the American Medical Association (JAMA)*, vol. 323, No. 18, pp. 1824-1836 (May 12, 2020, published online Apr. 13, 2020).
Sharifian-Dorche, M., Mowla, A., et al., "Neurological complications of coronavirus infection; a comparative review and lessons learned during COVID-19 pandemic", *Journal of the Neurological Sciences*, 2020, 417, 117085 (published online on Aug. 7, 2020).
Smieszek, S.P., Przychodzen, B.P., and Polymeropoulos, M.H. "Amantadine disrupts lysosomal gene expression: A hypothesis for COVID19 treatment", *International Journal of Antimicrobial Agents*, 55(6), 106004 (published online on Apr. 30, 2020 (source: PubMed, https://pubmed.ncbi.nlm.nih.gov/32361028/)).
Song, E., Iwasaki, A. et al., "Neuroinvasion of SARS-COV-2 in human and mouse brain", *Journal of Experimental Medicine*, vol. 218, No. 3, e20202135 (18+7 pages); https://doi.org/10.1084/jem.20202135 (published online on Mar. 1, 2021 (source: PubMed, https://pubmed.ncbi.nlm.nih.gov/33433624/)).
Stasi, C. Fallani, S., Voller, F., and Silvestri, C. "Treatment for COVID-19: An overview", *European Journal of Pharmacology*, 2020, 889, 173644 (published online on Oct. 11, 2020).
Supplementary European Search Report from the European Patent Office (EPO) (including a new search of the cyclo prolyl glycine scope), in respect of the corresponding (equivalent) European patent application No. 21793162.5, derived from PCT/US2021/027848; and the accompanying covering letter from EPO (dated Sep. 18, 2024 and sent Oct. 1, 2024).
Tipton, P. W., and Wszolek, Z.K. "Response to 'Does amantadine have a protective effect against COVID-19?'", *Neurologia i Neurochirurgia Polska (Polish Journal of Neurology and Neurosurgery*), 2020, vol. 54, No. 3, pp. 286-287 (published online on Jun. 25, 2020 (source: PubMed, https://pubmed.ncbi.nlm.nih.gov/3258-3401/)).
Tipton, P. W. and Wszolek, Z. K. "What can Parkinson's disease teach US about COVID-19?"; *Neurologia i Neurochirurgia Polska (Polish Journal of Neurology and Neurosurgery*), 2020, vol. 54, No. 2, pp. 204-206 (published online on Apr. 23, 2020 (source: PubMed, https://pubmed.ncbi.nlm.nih.gov/32323862/)).
Torres, J., Gong, X., et al., "Conductance and amantadine binding of a pore formed by a lysine-flanked transmembrane domain of SARS coronavirus envelope protein", *Protein Science*, 2007, 16, pp. 2065-2071 (May 28, 2007).
Verma, D.K., and Das, S. "Potential inhibitors of SARS-COV-2 main protease (Mpro) identified from the library of FDA approved drugs using molecular docking studies", ResearchGate preprint, Apr. 2020, 25 pages (published on Apr. 8, 2020).
World Health Organization (WHO), Novel Coronavirus(2019-nCoV), Situation Report 22, this document states that: WHO has named the disease COVID-19, short for "coronavirus disease 2019" (published on Feb. 11, 2020).
Wu, Y., Liu, C., Yang, C., et al., "Nervous system involvement after infection with COVID-19 and other coronaviruses", *Brain, Behavior, and Immunity*, 2020, 82, pp. 18-22 (published online on Mar. 30, 2020).
Yassin, A., Shaban, A., et al., "Neurological manifestations and complications of coronavirus disease 2019 (COVID-19): a systematic review and meta-analysis", *BMC Neurology*, 2021, 21, 138 (17 pages) (published online on Mar. 30, 2021).

* cited by examiner

—— % Wt Vehicle (A)
—— % Wt Dexamethasome (B)
—— % Wt GS-5734 (C)
—— % Wt Dexamethasone + GS-5734 (D)

---% Wt Vehicle (A)
---% Wt Methylprednisolone (B)
---% Wt Cyclo-Prolyl Glycine (C)
---% Wt Methylprednisolone + Cyclo-Prolyl Glycine (D)

A ▓ Vehicle
B ▓ Methylprednisolone
C ▓ Cyclo-Prolyl Glycine
D ▓ Methylprednisolone + Cyclo-Prolyl Glycine

METHODS FOR THE PROPHYLAXIS AND TREATMENT OF COVID AND COVID-19

CROSS REFERENCE TO RELATED APPLICATIONS

The present application:
is a Continuation in Part of PCT/US2021/027848, filed Apr. 17, 2022, which:
claims benefit of priority to U.S. Provisional Application Ser. No. 63/012,432, filed Apr. 20, 2020;
claims benefit of priority to U.S. Provisional Application Ser. No. 63/018,768, filed May 1, 2020;
claims benefit of priority to U.S. Provisional Application Ser. No. 63/032,116, filed May 29, 2020;
claims benefit of priority to U.S. Provisional Application Ser. No. 63/037,373, filed Jun. 10, 2020;
claims benefit of priority to U.S. Provisional Application Ser. No. 63/041,812, filed Jun. 19, 2020; and
claims benefit of priority to U.S. Provisional Application Ser. No. 63/170,350, filed Apr. 2, 2021;
each of which is incorporated by reference herein in its entirety.

TECHNICAL FIELD

The present invention relates generally to the fields of treatment and prophylaxis of COVID, notably COVID-19.

BACKGROUND

Coronaviruses are a group of related viruses that cause diseases in mammals and birds. In humans, coronaviruses cause respiratory tract infections that can range from mild to lethal. Mild illnesses include some cases of the common cold, while more lethal varieties can cause SARS, MERS, and Covid-19. No effective prophylactic or post-exposure therapy is currently available.

Coronaviruses were first discovered in the 1930s when an acute respiratory infection of domesticated chickens was shown to be caused by infectious bronchitis virus (IBV). In the 1940s, two more animal coronaviruses, mouse hepatitis virus (MHV) and transmissible gastroenteritis virus (TGEV), were isolated (McIntosh K (1974). Arber W, Haas R, Henle W, Hofschneider P H, Jerne N K, Koldovský P, Koprowski H, Maaløe O, Rott R (eds.). "Coronaviruses: A Comparative Review". Current Topics in Microbiology and Immunology/Ergebnisse der Mikrobiologie und Immunitätsforschung. Current Topics in Microbiology and Immunology/Ergebnisse der Mikrobiologie und Immunitätsforschung. Berlin, Heidelberg: Springer: 87. doi:10.1007/978-3-642-65775-7_3. ISBN 978-3-642-65775-7.).

Human coronaviruses were discovered in the 1960s. The earliest ones studied were from human patients with the common cold, which were later named human coronavirus 229E and human coronavirus OC43. Other human coronaviruses have since been identified, including SARS-CoV in 2003, HCoV NL63 in 2004, HKU1 in 2005, MERS-CoV in 2012, and SARS-CoV-2, in 2019. Most of these have involved serious respiratory tract infections (Zhu, Na; Zhang, Dingyu; Wang, Wenling; Li, Xingwang; Yang, Bo; Song, Jingdong; Zhao, Xiang; Huang, Baoying; Shi, Weifeng; Lu, Roujian; Niu, Peihua (2020-02-20). "A Novel Coronavirus from Patients with Pneumonia in China, 2019". The New England Journal of Medicine. 382 (8): 727-733. doi: 10.1056/NEJMoa2001017. ISSN 0028-4793. PMC 7092803. PMID 31978945.).

Coronaviruses vary significantly in risk factor. Some can kill more than 30% of those infected (such as MERS-CoV), and some are relatively harmless, such as the common cold. Coronaviruses cause colds with major symptoms, such as fever, and a sore throat from swollen adenoids, occurring primarily in the winter and early spring seasons. Coronaviruses can cause pneumonia (either direct viral pneumonia or secondary bacterial pneumonia) and bronchitis (either direct viral bronchitis or secondary bacterial bronchitis). The human coronavirus discovered in 2003, SARS-CoV, which causes severe acute respiratory syndrome (SARS), has a unique pathogenesis because it causes both upper and lower respiratory tract infections.

An outbreak of severe acute respiratory syndrome (SARS) began in 2002 in Asia. The virus was officially named the SARS coronavirus (SARS-CoV). More than 8,000 people were infected, about ten percent of whom died (Li F, Li W, Farzan M, Harrison S C (September 2005). "Structure of SARS coronavirus spike receptor-binding domain complexed with receptor". Science. 309 (5742): 1864-68. Bibcode:2005Sci . . . 309.1864L. doi:10.1126/science.1116480. PMID 16166518.).

In September 2012, a new type of coronavirus was identified, initially called Novel Coronavirus 2012, and officially named Middle East respiratory syndrome coronavirus (MERS-CoV). As of December 2019, 2,468 cases of MERS-CoV infection had been confirmed by laboratory tests, 851 of which were fatal, a mortality rate of approximately 34.5%("Middle East respiratory syndrome coronavirus (MERS-CoV)". WHO Archived from the original on 2019-10-18. Retrieved 2019-12-10.).

In early December 2019, a pneumonia outbreak was reported in Wuhan, China. On Dec. 31, 2019, the outbreak was traced to a novel strain of coronavirus, which was given the interim name 2019-nCoV by the World Health Organization (WHO), later renamed SARS-CoV-2 or Covid-19 by the International Committee on Taxonomy of Viruses ("Novel Coronavirus 2019, Wuhan, China". www.cdc.gov (CDC). 2020-01-23. Archived from the original on 2020-01-20. Retrieved 2020-01-23.)

As of Apr. 11, 2021, there have been at least 2,934,981 confirmed deaths and more than 135,855,351 confirmed cases worldwide in the coronavirus pneumonia pandemic. The US is the country with the highest number of casualties with more than 562,064 recorded deaths and 31,196,121 confirmed cases (COVID-19 Dashboard by the Center for Systems Science and Engineering (CSSE) at Johns Hopkins-coronavirus.jhu.edu/map. html).

SUMMARY

The present invention recognizes that there is a need for the prophylaxis or treatment of COVID and COVID-19.

A first aspect of the present invention generally relates to methods of prophylaxis or treatment of COVID or COVID-19 using various pharmaceutical compositions.

A second aspect of the present invention generally relates to methods of prophylaxis or treatment of COVID or COVID-19 using combinations of antimalarial drugs and antiviral drugs.

A third aspect of the present invention generally relates to methods of prophylaxis or treatment of COVID or COVID-19 using nanoparticle formulations that include pharmaceutical compositions.

A fourth aspect of the present invention generally relates to methods of prophylaxis or treatment of COVID or COVID-19 using combinations of various pharmaceutical compositions.

A fifth aspect of the present invention generally relates to methods of prophylaxis or treatment of COVID or COVID-19 using a polio vaccine and pharmaceutical compositions.

(4 mg/kg) in Chitosan nanoparticles, or Donepezil (0.15 mg/kg) plus GS-5734 (4 mg/kg) in Chitosan nanoparticles (n=24).

Figure 48:
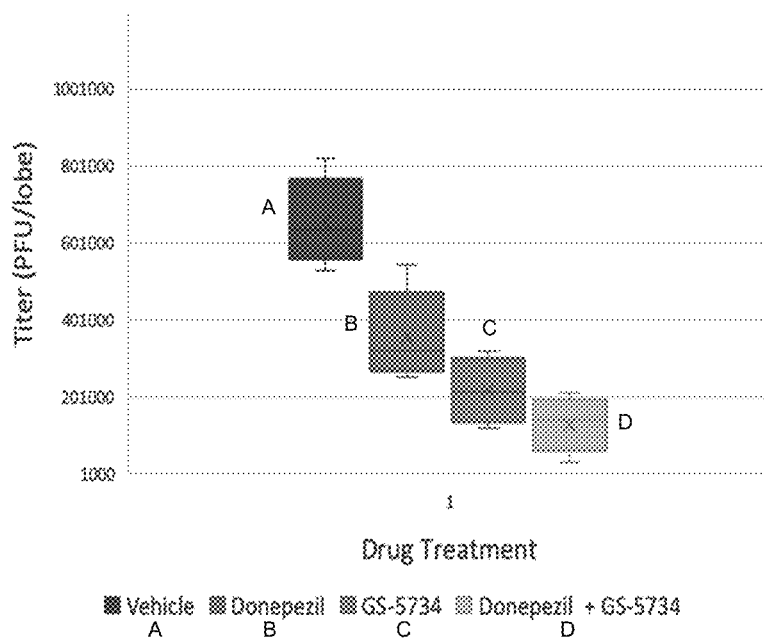

FIG. 48 generally depicts Lung Titers studies of Donepezil and GS-5734 (intranasal). SARS-CoV lung titers in mice infected and treated beginning at −1 dpi with either vehicle (n=8) or Donepezil (0.15 mg/kg) in Chitosan nanoparticles, GS-5734 (4 mg/kg) in Chitosan nanoparticles, or Donepezil (0.15 mg/kg) plus GS-5734 (4 mg/kg) in Chitosan nanoparticles (n=24).

Figure 49:
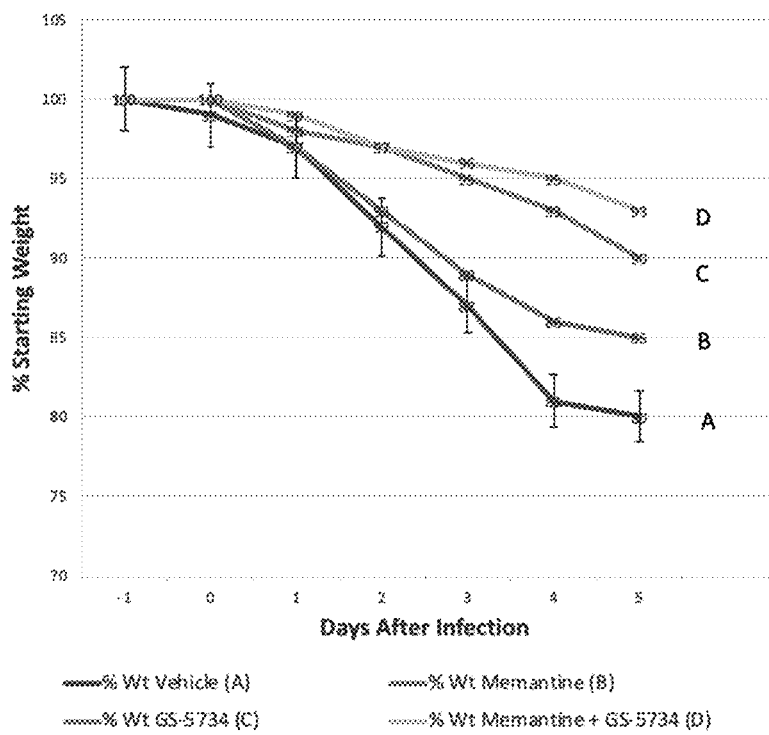

FIG. 49 generally depicts Weight loss studies of Memantine and GS-5734 (Intranasal). Percent starting weight of Ces1c−/− mice infected with 104 PFU SARS-CoV MA15 treated beginning at −1 dpi with either vehicle (n=8) or Memantine (0.15 mg/kg) in Chitosan nanoparticles, GS-5734 (4 mg/kg) in Chitosan nanoparticles, or Memantine (0.15 mg/kg) plus GS-5734 (4 mg/kg) in Chitosan nanoparticles (n=24).

Figure 50:
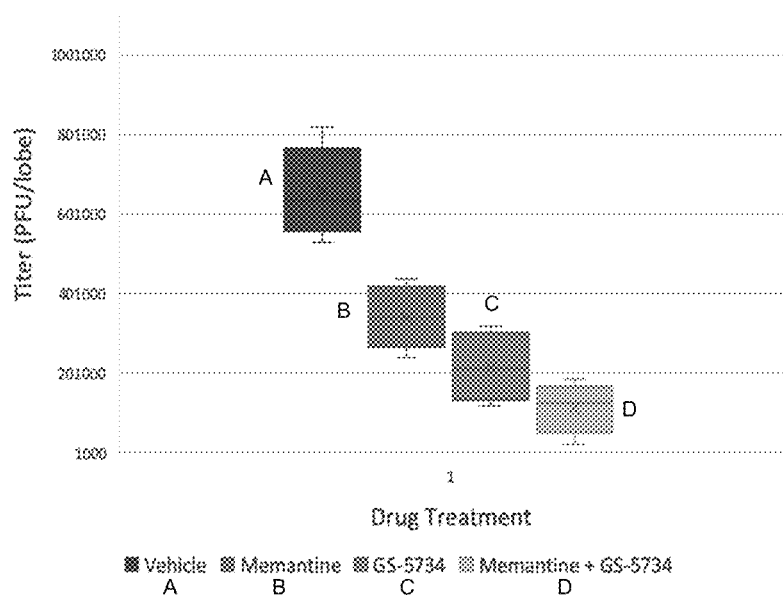

FIG. 50 generally depicts Lung Titers studies of Memantine and GS-5734 (intranasal). SARS-CoV lung titers in mice infected and treated beginning at −1 dpi with either vehicle (n=8) or Memantine (0.15 mg/kg) in Chitosan nanoparticles, GS-5734 (4 mg/kg) in Chitosan nanoparticles, or Memantine (0.15 mg/kg) plus GS-5734 (4 mg/kg) in Chitosan nanoparticles (n=24).

Figure 51:
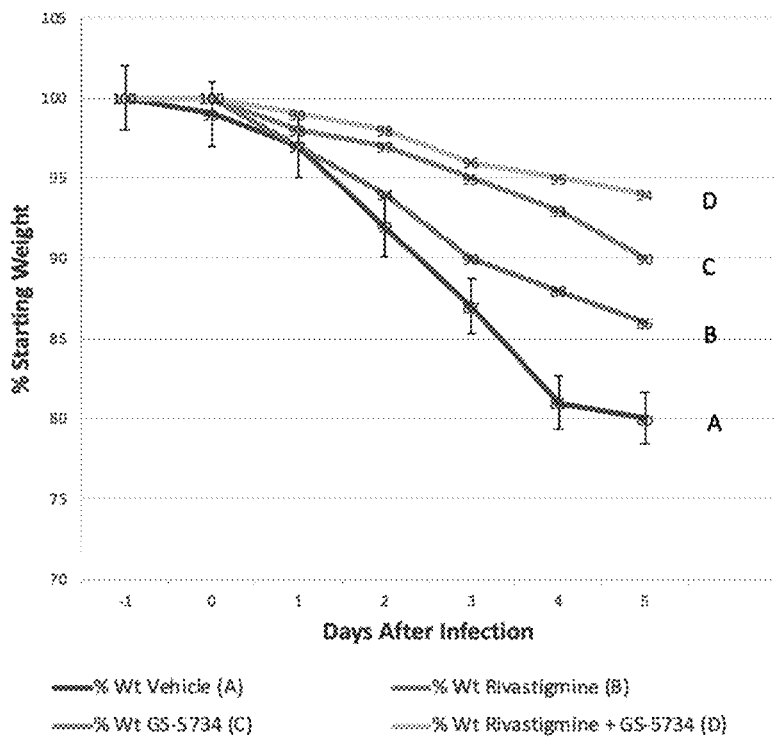

FIG. 51 generally depicts Weight loss studies of Rivastigmine and GS-5734 (Intranasal). Percent starting weight of Ces1c−/− mice infected with 104 PFU SARS-CoV MA15 treated beginning at −1 dpi with either vehicle (n=8) or Rivastigmine (0.01 mg/kg) in Chitosan nanoparticles, GS-5734 (4 mg/kg) in Chitosan nanoparticles, or Rivastigmine (0.4 mg/kg) plus GS-5734 (4 mg/kg) in Chitosan nanoparticles (n=24).

Figure 52:
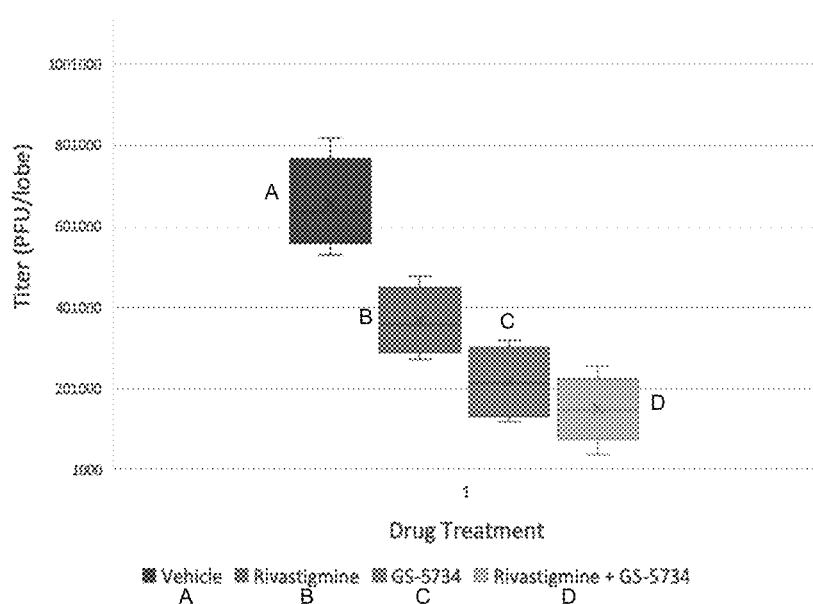

FIG. 52 generally depicts Lung Titers studies of Rivastigmine and GS-5734 (intranasal). SARS-CoV lung titers in mice infected and treated beginning at −1 dpi with either vehicle (n=8) or Rivastigmine (0.01 mg/kg) in Chitosan nanoparticles, GS-5734 (4 mg/kg) in Chitosan nanoparticles, or Rivastigmine (0.01 mg/kg) plus GS-5734 (4 mg/kg) in Chitosan nanoparticles (n=24).

Figure 53:
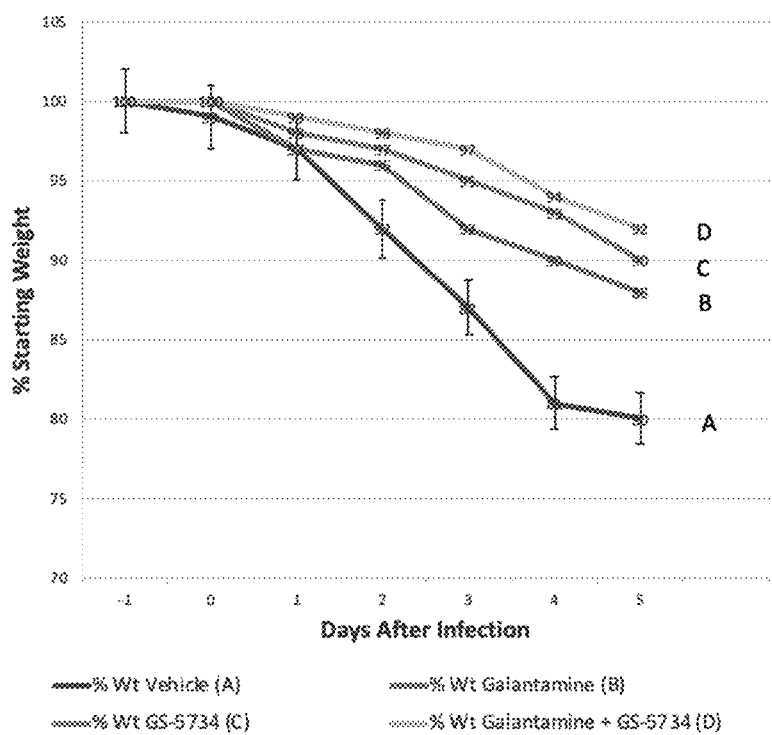

FIG. 53 generally depicts Weight loss studies of Galantamine and GS-5734 (Intranasal). Percent starting weight of Ces1c−/− mice infected with 104 PFU SARS-CoV MA15 treated beginning at −1 dpi with either vehicle (n=8) or Galantamine (0.20 mg/kg) in Chitosan nanoparticles, GS-5734 (4 mg/kg) in Chitosan nanoparticles, or Galantamine (0.20 mg/kg) plus GS-5734 (4 mg/kg) in Chitosan nanoparticles (n=24).

Figure 54:
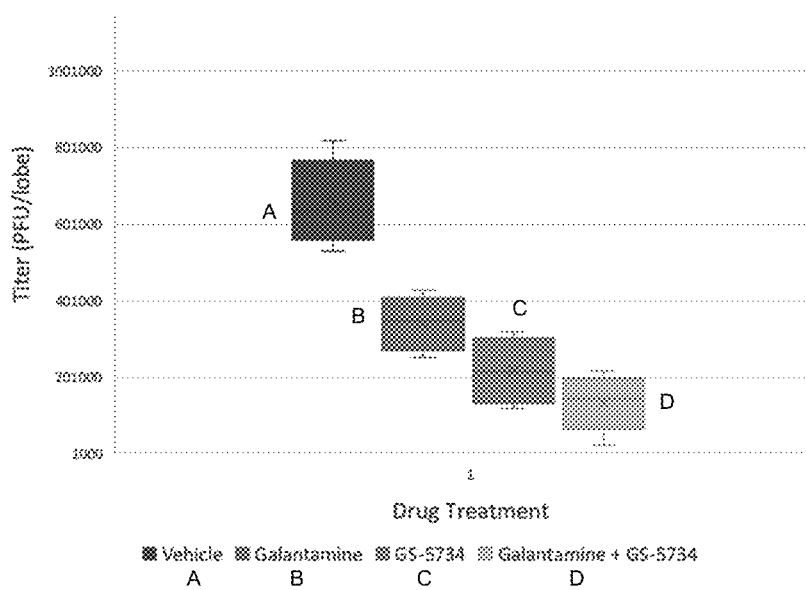

FIG. 54 generally depicts Lung Titers studies of Galantamine and GS-5734 (intranasal). SARS-CoV lung titers in mice infected and treated beginning at −1 dpi with either vehicle (n=8) or Galantamine (0.20 mg/kg) in Chitosan nanoparticles, GS-5734 (4 mg/kg) in Chitosan nanoparticles, or Galantamine (0.01 mg/kg) plus GS-5734 (4 mg/kg) in Chitosan nanoparticles (n=24).

Figure 55:
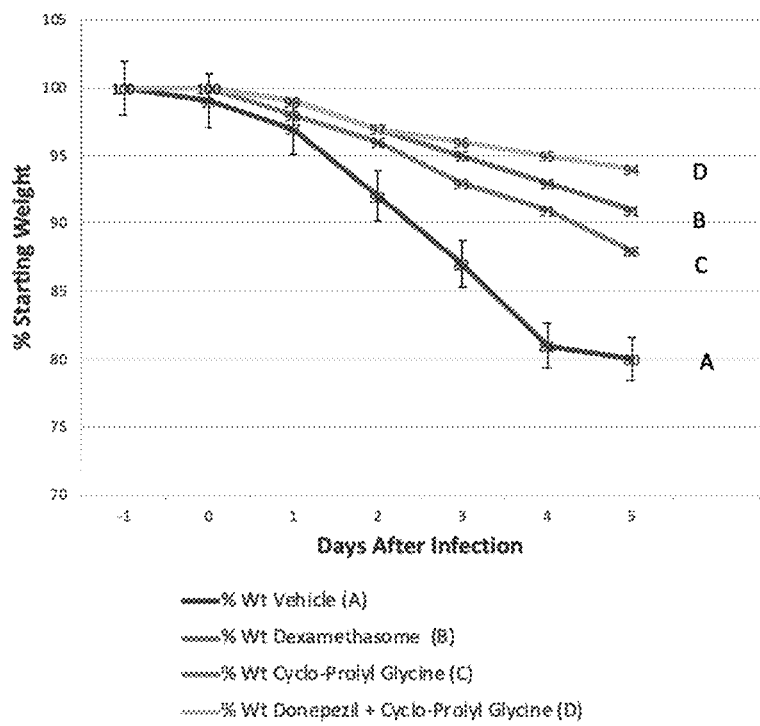

FIG. 55 generally depicts Weight Loss Studies of Dexamethasone and Cyclic Prolyl Glycine-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Cyclic Prolyl Glycine (0.2 mg/kg) in oral powder/suspension, or Dexamethasone (0.10 mg/kg) plus Cyclic Prolyl Glycine (0.2 mg/kg) in oral power/suspension (n=24).

Figure 56:
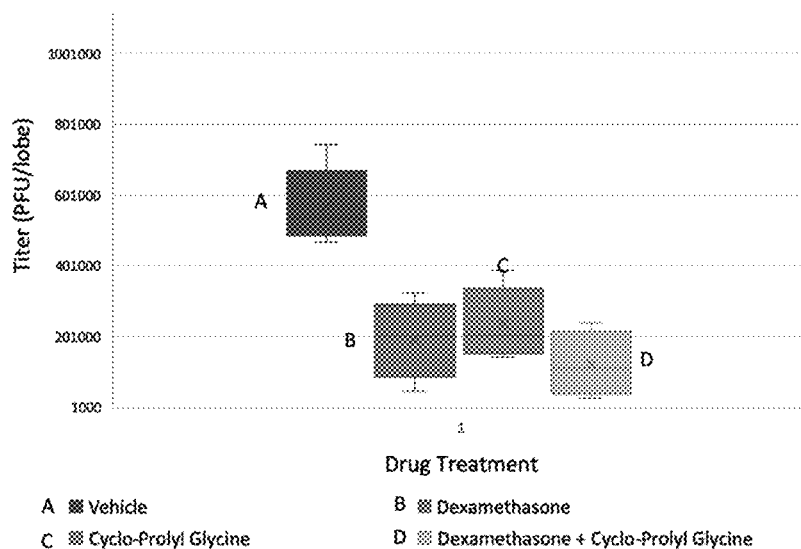

FIG. 56 generally depicts Lung Titers Studies of Dexamethasone and Cyclic Prolyl Glycine-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Cyclic Prolyl Glycine (0.2 mg/kg) in oral powder/suspension, or Dexamethasone (0.10 mg/kg) plus Cyclic Prolyl Glycine (0.2 mg/kg) in oral power/suspension (n=24)

Figure 57:
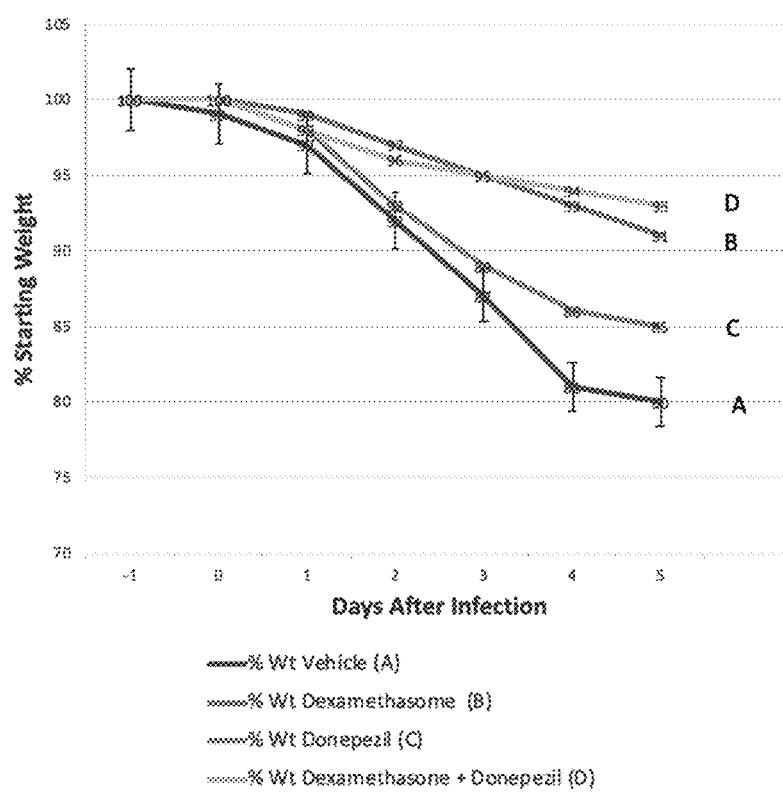

FIG. 57 generally depicts Weight Loss Studies of Dexamethasone and Donepezil-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Donepezil (0.15 mg/kg) in oral powder/suspension, or Dexamethasone (0.10 mg/kg) plus Donepezil (0.15 mg/kg) in oral power/suspension (n=24).

Figure 58:
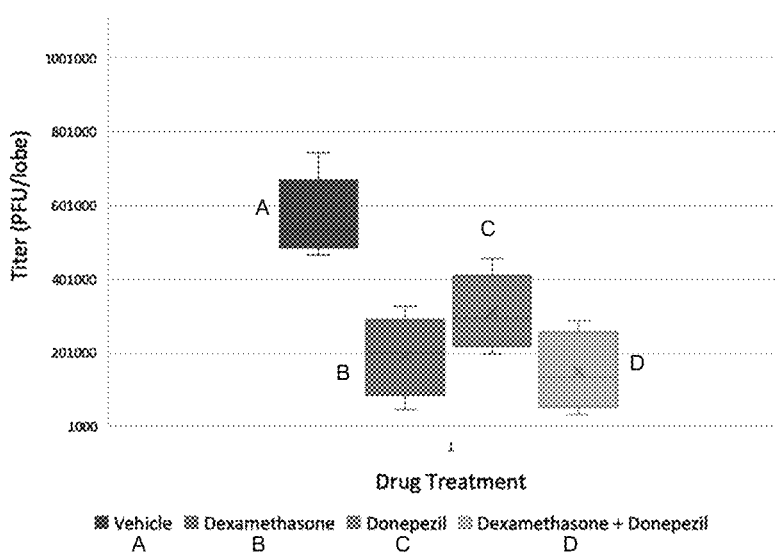

FIG. 58 generally depicts Lung Tier Studies of Dexamethasone and Donepezil-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Donepezil (0.15 mg/kg) in oral powder/suspension, or Dexamethasone (0.10 mg/kg) plus Donepezil (0.15 mg/kg) in oral power/suspension (n=24).

Figure 59:
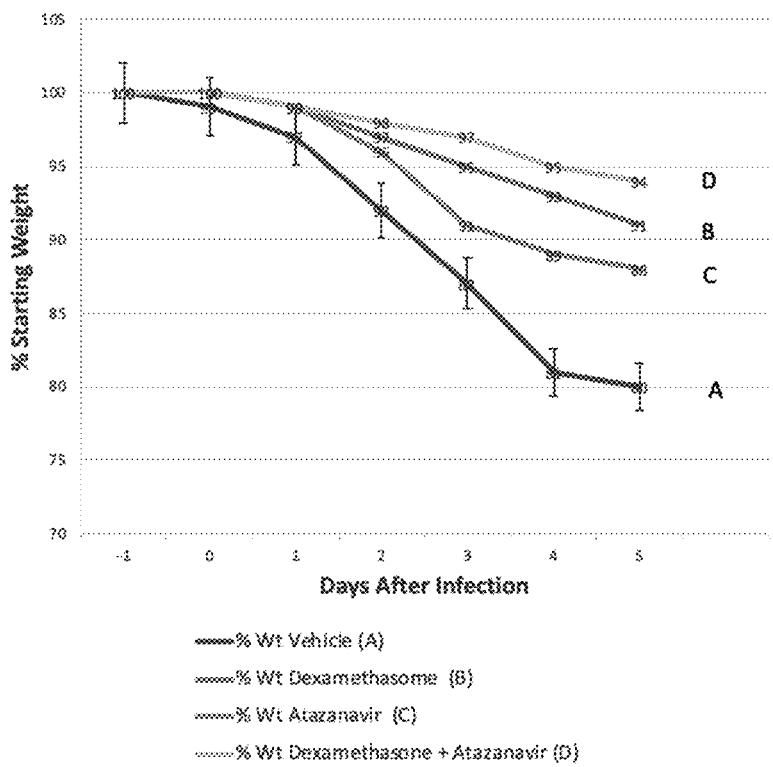

FIG. 59 generally depicts Weight Loss Studies of Dexamethasone and Atazanavir-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Atazanavir (4 mg/kg) in oral powder/suspension, or Dexamethasone (0.10 mg/kg) plus Atazanavir (4 mg/kg) in oral power/suspension (n=24).

Figure 60:
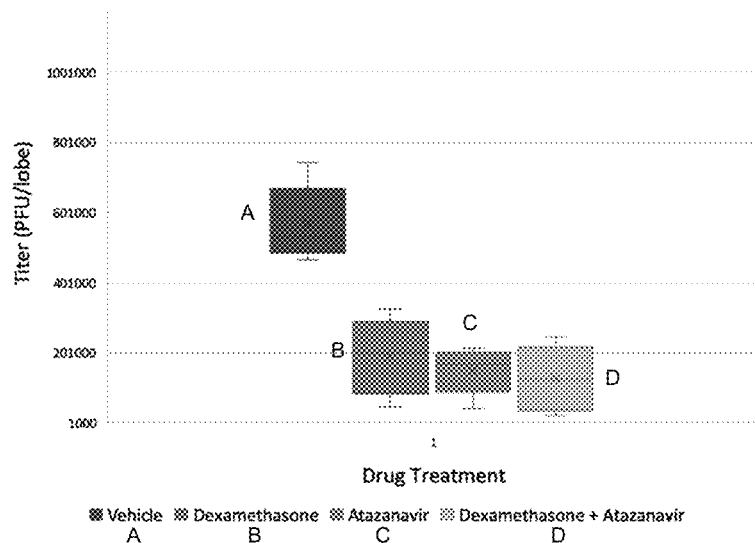

FIG. 60 generally depicts Lung Tier Studies of Dexamethasone and Atazanavir-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Atazanavir (4 mg/kg) in oral powder/suspension, or Dexamethasone (0.10 mg/kg) plus Atazanavir (4 mg/kg) in oral power/suspension (n=24).

Figure 61:
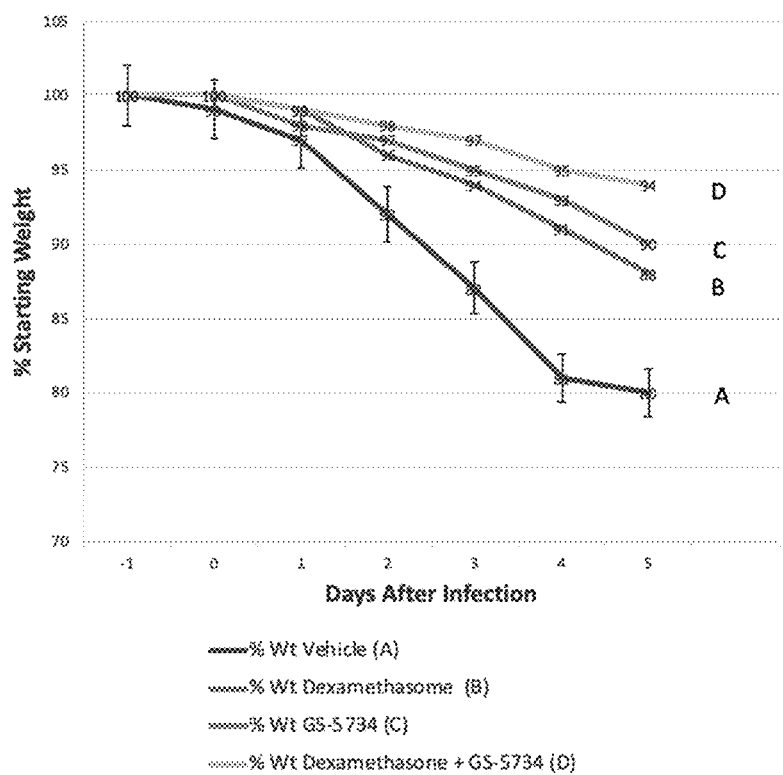

FIG. 61 generally depicts Weight loss studies of Dexamethasone and GS-5734 (Intranasal). Percent starting weight of Ces1c−/− mice infected with 104 PFU SARS-CoV MA15 treated beginning at −1 dpi with either vehicle (n=8) or Dexamethasone (0.10 mg/kg) in Chitosan nanoparticles, GS-5734 (4 mg/kg) in Chitosan nanoparticles, or Dexamethasone (0.10 mg/kg) plus GS-5734 (4 mg/kg) in Chitosan nanoparticles (n=24).

Figure 62:
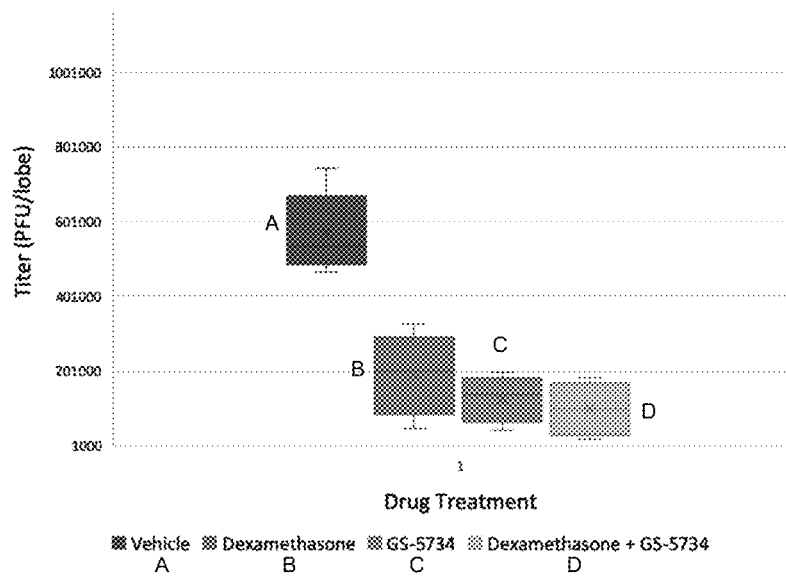

FIG. 62 generally depicts Lung Tiers Studies of Dexamethasone and GS-5734 (Intranasal). Percent starting weight of Ces1c−/− mice infected with 104 PFU SARS-CoV MA15 treated beginning at −1 dpi with either vehicle (n=8) or Dexamethasone (0.10 mg/kg) in Chitosan nanoparticles, GS-5734 (4 mg/kg) in Chitosan nanoparticles, or Dexamethasone (0.10 mg/kg) plus GS-5734 (4 mg/kg) in Chitosan nanoparticles (n=24).

Figure 63:
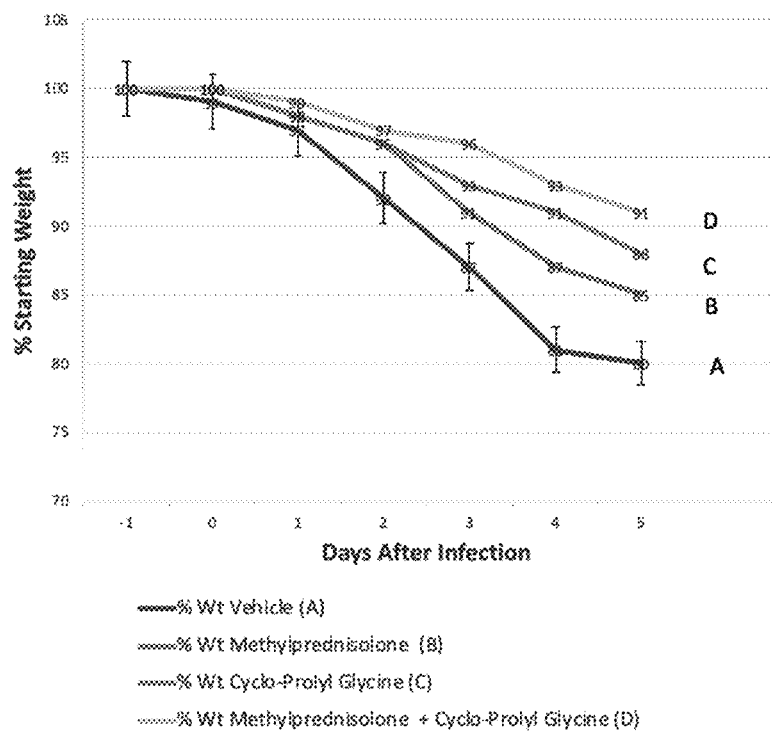

FIG. 63 generally depicts Weight Loss Studies of Cyclic Prolyl Glycine and Methylprednisolone-(Oral). Percent starting weight of Ces1c−/− mice infected with 104 PFU SARS-CoV MA15 treated beginning at −1 dpi with either vehicle (n=8) or Cyclic Prolyl Glycine (0.20 mg/kg) in oral powder/suspension or Methylprednisolone (0.50 mg/kg) in oral powder/suspension, or Cyclic Prolyl Glycine (0.20 mg/kg) plus Methylprednisolone (0.50 mg/kg) in oral power/suspension (n=24).

Figure 64:
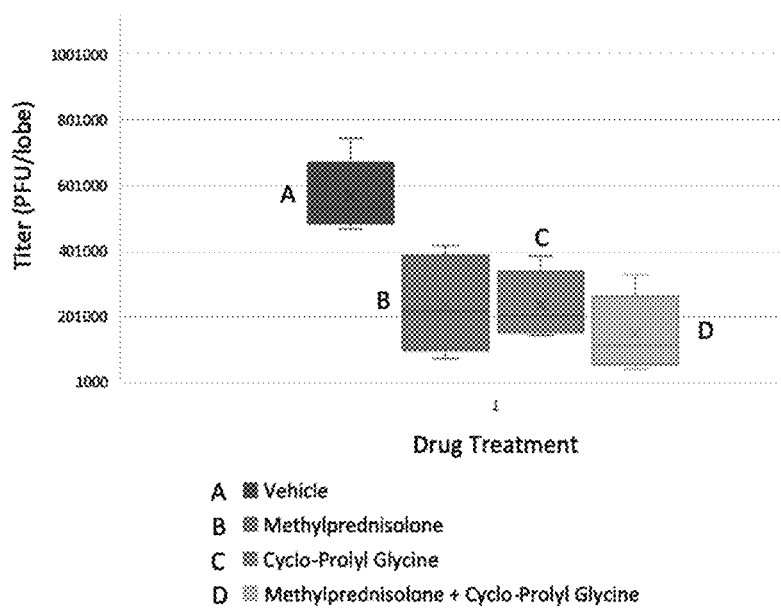

FIG. 64 generally depicts Lung Titers Studies of Cyclic Prolyl Glycine and Methylprednisolone-(Oral). Percent starting weight of Ces1c−/− mice infected with 104 PFU SARS-CoV MA15 treated beginning at −1 dpi with either vehicle (n=8) or Cyclic Prolyl Glycine (0.20 mg/kg) in oral powder/suspension or Methylprednisolone (0.50 mg/kg) in oral powder/suspension, or Cyclic Prolyl Glycine (0.20 mg/kg) plus Methylprednisolone (0.50 mg/kg) in oral power/suspension (n=24).

Figure 65:
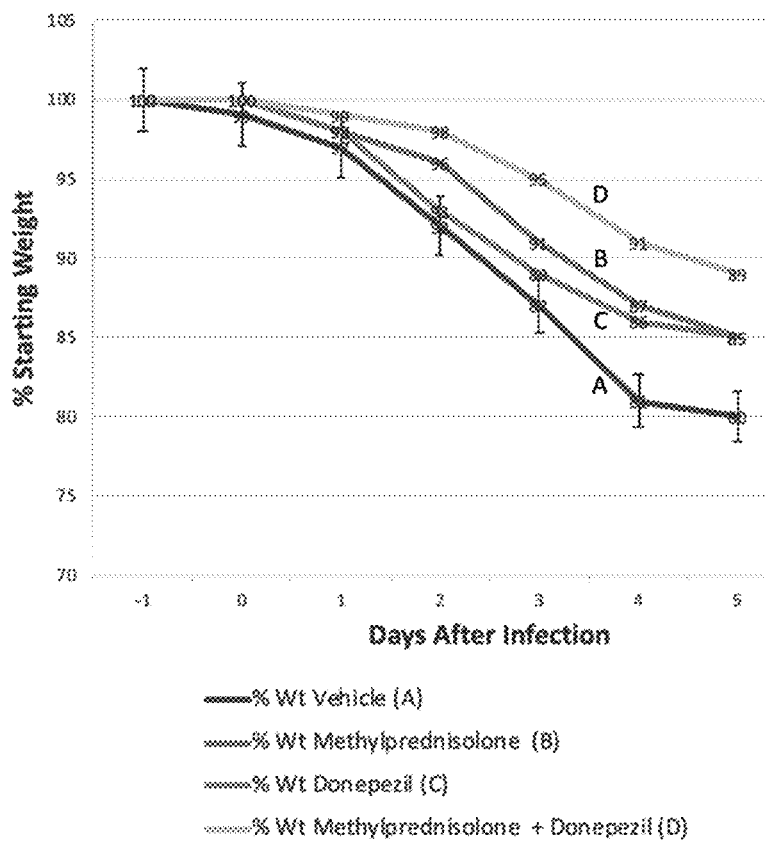

FIG. 65 generally depicts Weight Loss Studies of Donepezil and Methylprednisolone-(Oral). Percent starting weight of Ces1c−/− mice infected with 104 PFU SARS-CoV MA15treated beginning at −1 dpi with either vehicle (n=8) or Donepezil (0.15 mg/kg) in oral powder/suspension or Methylprednisolone (0.50 mg/kg) in oral powder/suspension, or Donepezil (0.15 mg/kg) plus Methylprednisolone (0.50 mg/kg) in oral power/suspension (n=24).

Figure 66:
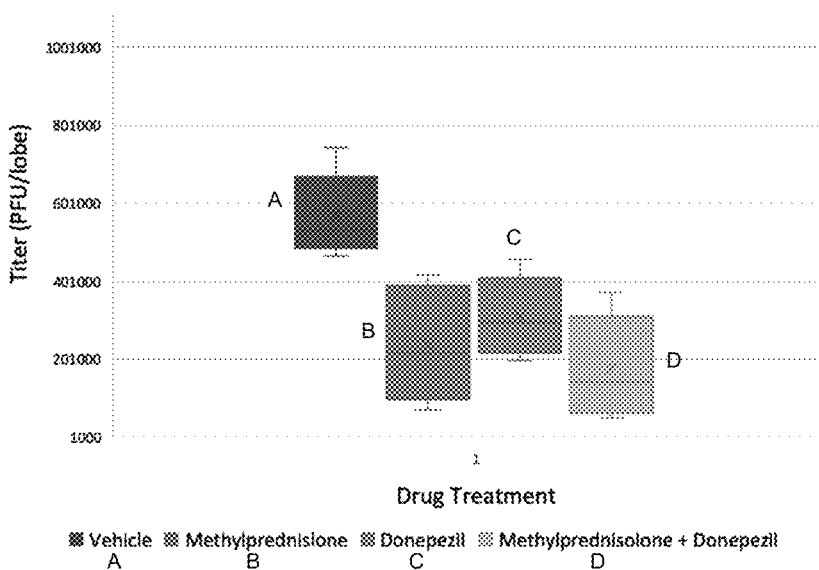

FIG. 66 generally depicts Lung Titers Studies of Donepezil and Methylprednisolone-(Oral). Percent starting weight of Ces1c−/− mice infected with 104 PFU SARS-CoV MA15 treated beginning at −1 dpi with either vehicle (n=8) or Donepezil (0.15 mg/kg) in oral powder/suspension or Methylprednisolone (0.50 mg/kg) in oral powder/suspension, or Donepezil (0.15 mg/kg) plus Methylprednisolone (0.50 mg/kg) in oral power/suspension (n=24).

Figure 67:
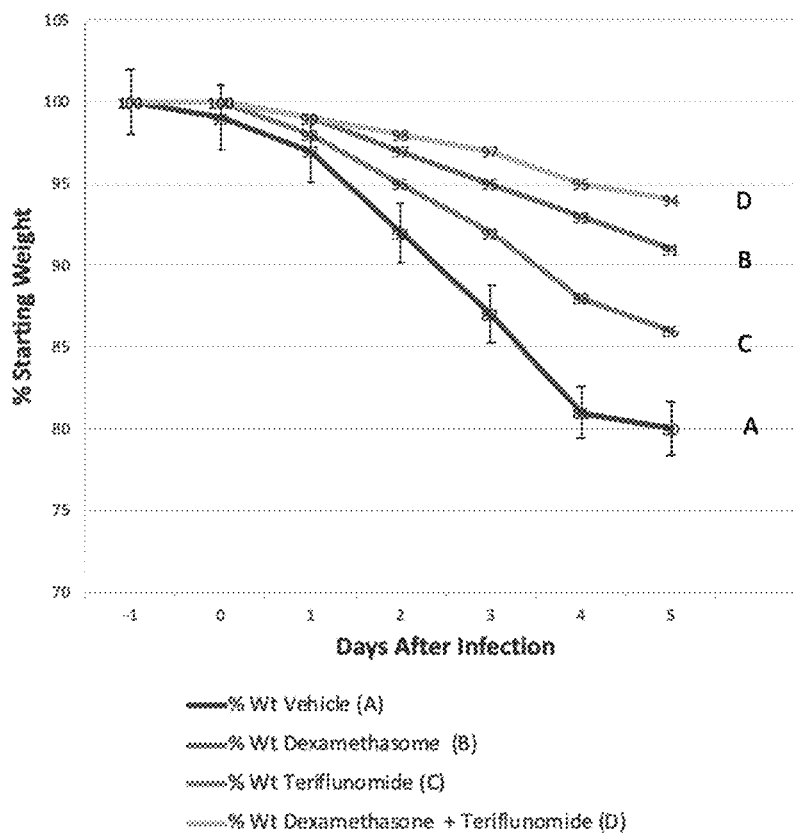

FIG. 67 generally depicts Weight Loss Studies of Dexamethasone and Teriflunomide-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Teriflunomide (0.20 mg/kg) in oral powder/suspension, or Dexamethasone (0.10 mg/kg) plus Teriflunomide (0.20 mg/kg) in oral power/suspension (n=24).

Figure 68:
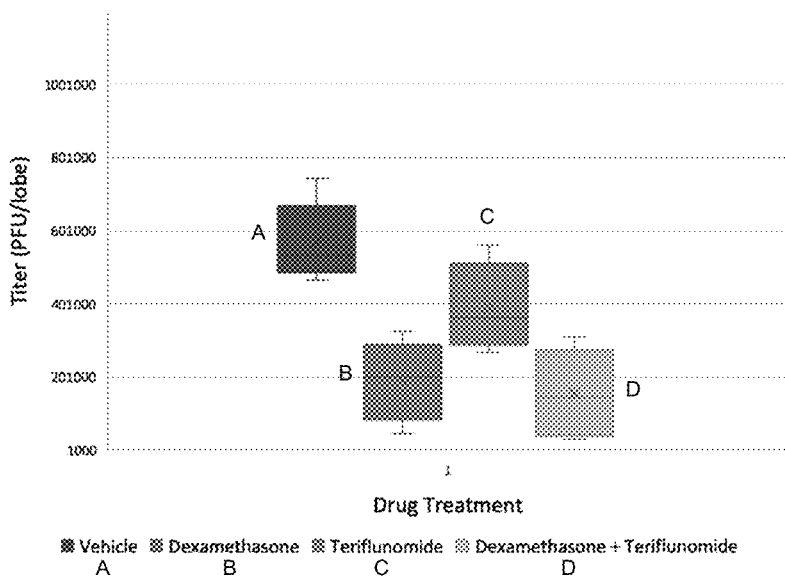

FIG. 68 generally depicts Lung Titers Studies of Dexamethasone and Teriflunomide-(Oral). Percent starting weight of Ces1c−/− mice infected with 104 PFU SARS-CoV MA15 treated beginning at −1 dpi with either vehicle (n=8) or Dexamethasone (0.10 mg/kg) in oral powder/suspension or Teriflunomide (0.20 mg/kg) in oral powder/suspension, or Dexamethasone (0.10 mg/kg) plus Teriflunomide (0.20 mg/kg) in oral power/suspension (n=24).

Figure 69:
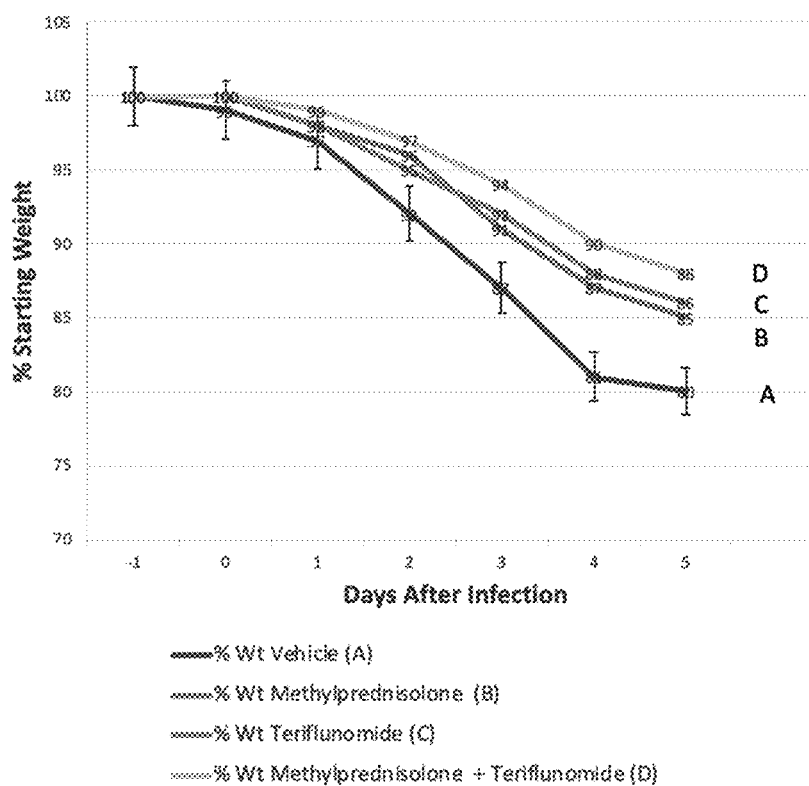

FIG. 69 generally depicts Weight Loss Studies of Methylprednisolone and Teriflunomide—(Oral). Percent starting weight of Ces1c−/− mice infected with 104 PFU SARS-CoV MA15 treated beginning at −1 dpi with either vehicle (n=8) or Methylprednisolone (0.50 mg/kg) in oral powder/suspension or Teriflunomide (0.20 mg/kg) in oral powder/suspension, or Methylprednisolone (0.50 mg/kg) plus Teriflunomide (0.20 mg/kg) in oral power/suspension (n=24).

Figure 70:
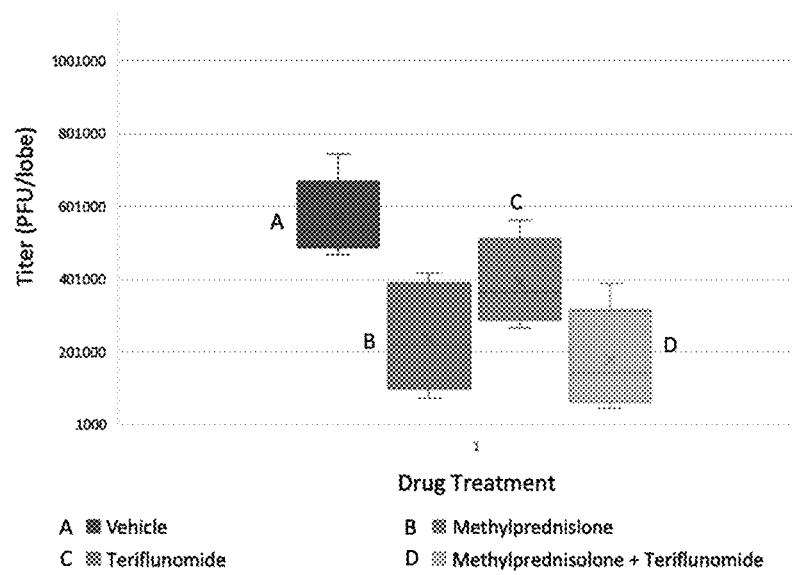

FIG. 70 generally depicts Lung Titers Studies of Methylprednisolone and Teriflunomide in—Oral. Percent starting weight of Ces1c−/− mice infected with 104 PFU SARS-CoV MA15 treated beginning at −1 dpi with either vehicle (n=8) or Methylprednisolone (0.50 mg/kg) in oral powder/suspension or Teriflunomide (0.20 mg/kg) in oral powder/suspension, or Methylprednisolone (0.50 mg/kg) plus Teriflunomide (0.20 mg/kg) in oral power/suspension (n=24).

Figure 71:
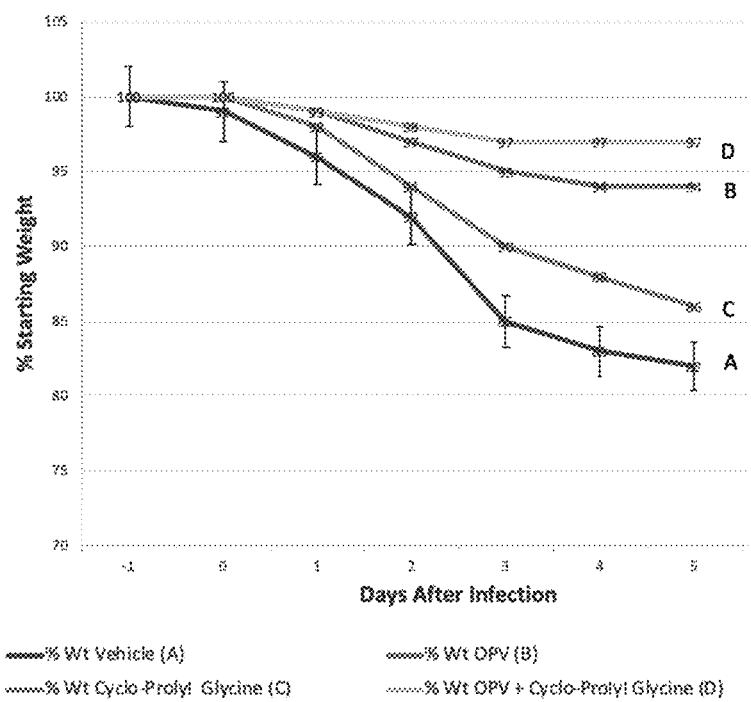

FIG. 71 generally depicts Weight Loss Studies of Cyclic Prolyl Glycine (oral) and Ivermectin (oral). Percent starting weight of Ces1c−/− mice infected with 104 PFU SARS-CoV MA15 treated beginning at −1 dpi with either vehicle (n=8) or Cyclic Prolyl Glycine (0.2 mg/kg) in oral powder/suspension, Ivermectin in oral solution (0.4 mg/kg), or Cyclic Prolyl Glycine (0.2 mg/kg) plus Ivermectin in oral solution (0.4 mg/kg) (n=24).

Figure 72:
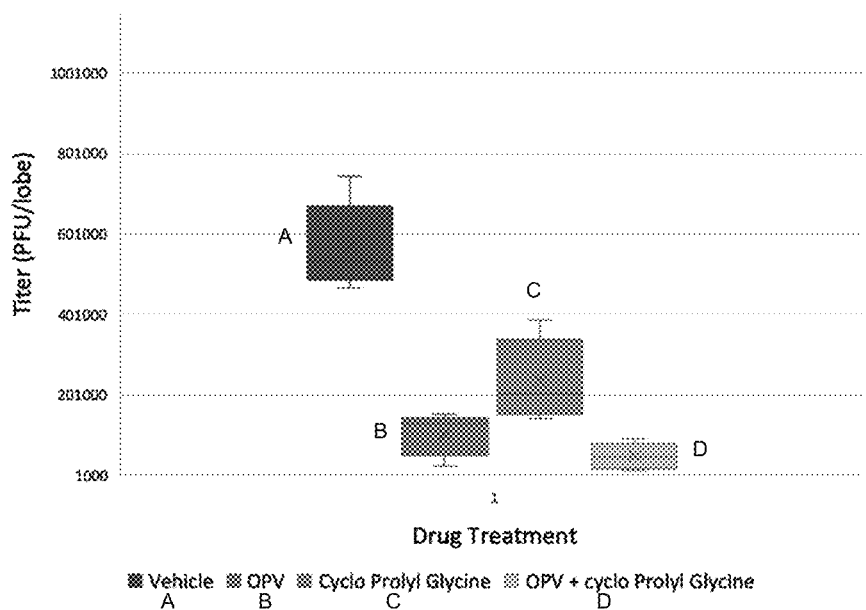

FIG. 72 generally depicts Lung Titers Studies of Cyclic Prolyl Glycine (oral) and Ivermectin (oral). SARS-CoV lung titers in mice infected and treated beginning at −1 dpi with either vehicle (n=8) or Cyclic Prolyl Glycine (0.2 mg/kg) in oral powder/suspension, Ivermectin in oral solution (0.4 mg/kg), or Cyclic Prolyl Glycine (0.2 mg/kg) plus Ivermectin in oral solution (0.4 mg/kg) (n=24).

Figure 73:
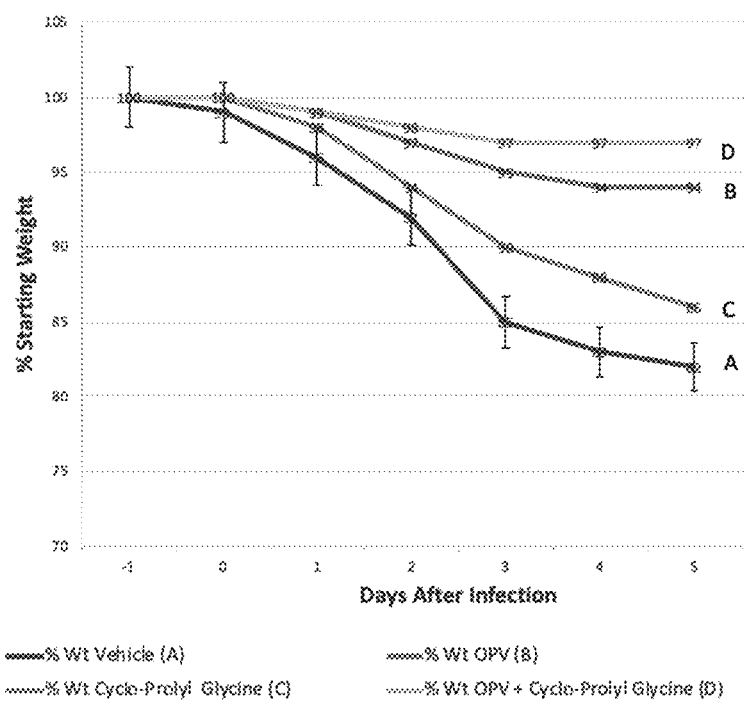

FIG. 73 generally depicts Weight Loss Studies of Cyclic Prolyl Glycine (oral) and Oral Polio Vaccine. Percent starting weight of Ces1c−/− mice infected with 104 PFU SARS-CoV MA15 treated beginning at −1 dpi with either vehicle (n=8) or Cyclic Prolyl Glycine (0.2 mg/kg) in oral powder/suspension, Oral Polio Vaccine 0.45 (log 10 $C_{CID}$50/μl) in oral solution, or Cyclic Prolyl Glycine (0.2 mg/kg) plus Oral Polio Vaccine 0.45 ($log^{10}$ CCID50/μl) in oral solution (n=24).

FIG. 74 generally depicts Lung Titers Studies of Cyclic Prolyl Glycine (oral) and Oral Polio Vaccine. SARS-CoV lung titers in mice infected and treated beginning at −1 dpi with either vehicle (n=8) or Cyclic Prolyl Glycine (0.2 mg/kg) in oral powder/suspension, Oral Polio Vaccine 0.45 ($log^{10}$) $CCID_{50}$/μl) in oral solution, or Cyclic Prolyl Glycine (0.2 mg/kg) plus Oral Polio Vaccine 0.45 ($log^{10}$ $CCID_{50}$/μl) in oral solution (n=24).

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures in cell culture, chemistry, microbiology, molecular biology, cell science and cell culture described below are well known and commonly employed in the art. Conventional methods are used for these procedures, such as those provided in the art and various general references. Where a term is provided in the singular, the plural of that term is contemplated; and where a term is provided in the plural, the singular of that term is contemplated. The nomenclature used herein and the laboratory procedures described below are those well-known and commonly employed in the art. As employed throughout the disclosure, the following terms, unless otherwise indicated, shall be understood to have the following meanings:

"Directly" refers to direct causation of a process that does not require intermediate steps.

"Indirectly" refers to indirect causation that requires intermediate steps.

Other technical terms used herein have their ordinary meaning in the art that they are used, as exemplified by a variety of technical dictionaries.

INTRODUCTION

Figure 5:
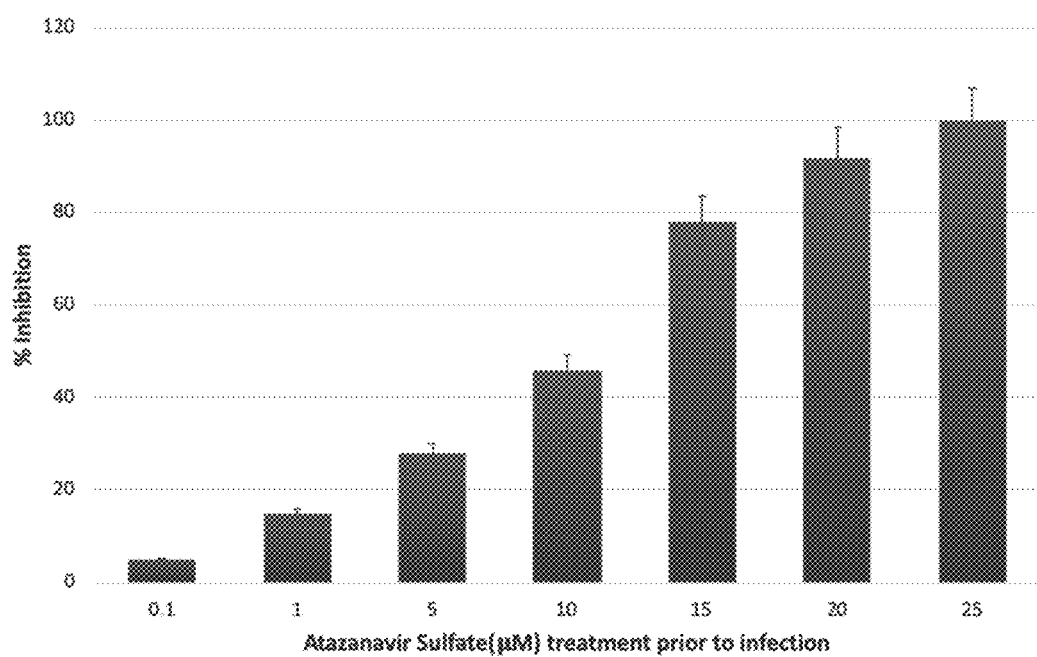
FIG. 5 generally depicts Percentage Inhibition of Atazanavir Sulfate Prior to Infection.

The present invention recognizes that there is a need for the prophylaxis or treatment of COVID and COVID-19.

As a non-limiting introduction to the breath of the present invention, the present invention includes several general and useful aspects, including:

1) a method of prophylaxis or treatment of COVID or COVID-19 using various pharmaceutical compositions;
2) a method of prophylaxis or treatment of COVID or COVID-19 using combinations of antimalarial drugs and antiviral drugs;
3) a method of prophylaxis or treatment of COVID or COVID-19 using nanoparticle formulations that include pharmaceutical compositions;
4) a method of prophylaxis or treatment of COVID or COVID-19 using combinations of various pharmaceutical compositions; and 5) a method of prophylaxis or treatment of COVID or COVID-19 using a polio vaccine and pharmaceutical compositions.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I Methods of Prophylaxis or Treatment of COVID or COVID-19 Using Various Pharmaceutical Compositions The present invention also includes methods of prophylaxis or treatment of COVID or COVID-19 using various pharmaceutical compositions.

A first aspect of the present invention includes methods of prophylaxis or treatment of COVID or COVID-19, including: a) providing a subject in need of said prophylaxis or treatment; b) providing at least one pharmaceutical composition including one or more of the following components: 1) Artemether and Lumefantrine; 2) Atazanavir Sulfate; 3) Efavirenz; 4) Fosamprenavir Calcium; 5) Saquinavir; 6) Remdesivir (GS-5734); 7) Digoxin; 8) Cyclic Prolyl Glycine; 9) Donepezil; 10) Memantine; 11) Rivastigmine; 12) Galantamine; 13) Valsartan; 14) Teriflunomide; 15) Ivermectin and 16) a combination thereof; wherein said components are being provided together or separately; wherein the components are administered together or separately; and wherein the components are provided in a pharmaceutically acceptable diluent, adjuvant and/or excipient; c) administering a pharmaceutically effective amount of the at least one pharmaceutical composition to the subject; wherein the subject is provided prophylaxis or treatment of COVID-19.

Another aspect of the present invention includes wherein the pharmaceutical composition includes Artemether/Lumefantrine in a dose between about 40 mg/240 mg to about 80 mg/480 mg, preferably about twice a day.

A further aspect of the present invention includes wherein the pharmaceutical composition comprises Atazanavir Sulfate in a dose between about 100 mg to about 300 mg, preferably about once a day.

An additional aspect of the present invention includes wherein the pharmaceutical composition includes Efavirenz in a dose of about 600 mg, preferably a day.

Another aspect of the present invention includes wherein the pharmaceutical composition includes Fosamprenavir Calcium in a dose of about 1400 mg, preferably about twice a day.

A further aspect of the present invention includes wherein the pharmaceutical composition includes Saquinavir in a dose of about 500 mg, preferably about twice a day.

An additional aspect of the present invention includes wherein the pharmaceutical composition includes Remdesivir (GS-5734), preferably in an intranasal formulation of about 20 mg to about 100 mg, preferably about twice a day.

Another aspect of the present invention includes wherein the pharmaceutical composition includes Digoxin, preferably in an oral dose of about 10 to about 15 mg/kg.

A further aspect of the present invention includes wherein the pharmaceutical composition includes Cyclic Prolyl Glycine, preferably in an oral dose of about 10 mg to about 50 mg or 0.1 to 1.0 mg/kg, preferably about per day or twice a day.

An additional aspect of the present invention includes wherein the pharmaceutical composition includes Donepezil, preferably in an oral dose of about 0.1 to about 0.50 mg/kg.

Another aspect of the present invention includes wherein the pharmaceutical composition includes Memantine, preferably in an oral dose of about 0.10 to about 0.50 mg/kg.

A further aspect of the present invention includes wherein the pharmaceutical composition includes Rivastigmine, preferably in an oral dose of about 0.01 to about 0.05 mg/kg.

An additional aspect of the present invention includes wherein the pharmaceutical composition includes Galantamine, preferably in an oral dose of about 0.10 to about 0.50 mg/kg.

Another aspect of the present invention includes wherein the pharmaceutical composition includes Valsartan, preferably in an oral dose of about 2.00 to about 5.00 mg/kg.

A further aspect of the present invention includes wherein the pharmaceutical composition includes Teriflunomide, preferably in an oral dose of about 0.20 to about 1.00 mg/kg.

II Methods of Prophylaxis or Treatment of COVID or COVID-19 Using Combinations of Antimalarial Drugs and Antiviral Drugs The present invention also includes methods of prophylaxis or treatment of COVID or COVID-19 using combinations of antimalarial drugs and antiviral drugs.

A second aspect of the present invention includes methods of prophylaxis or treatment of COVID or COVID-19, including: a) providing a subject in need of said prophylaxis or treatment; b) providing at least one pharmaceutical composition including one or more of the following combinations of an antimalarial drug and an antiviral drug that optionally form synergy effects against a coronavirus: 1) Artemether and Atazanavir; 2) Artemether and Efavirenz; 3) Artemether and Fosamprenavir Calcium; 4) Artemether and Saquinavir; 5) Artemether and Remdesivir; 6) Hydroxychloroquine and Atazanavir; 7) Hydroxychloroquine and Efavirenz; 8) Hydroxychloroquine and Fosamprenavir Calcium; 9) Hydroxychloroquine and Saquinavir; 10) Hydroxychloroquine and Remdesivir; 11) said antimalarial drug comprises Artemether, Hydroxychloroquine, or a combination thereof; 12) said antiviral drug comprises Atazanavir, Efavirenz, Fosamprenavir Calcium, Saquinavir, Remdesivir, or a combination thereof; and 13) a combination thereof; wherein the components are provided together or separately; wherein the components are administered together or separately; and wherein the components are provided in a pharmaceutically acceptable diluent, adjuvant and/or excipient; c) administering a pharmaceutically effective amount of the at least one pharmaceutical composition to the subject; wherein the subject is provided prophylaxis or treatment of COVID-19.

Another aspect of the present invention includes wherein the pharmaceutical includes Artemether and Atazanavir.

A further aspect of the present invention includes wherein the pharmaceutical includes Artemether and Efavirenz.

An additional aspect of the present invention includes wherein the pharmaceutical includes Artemether and Fosamprenavir Calcium.

Another aspect of the present invention includes wherein the pharmaceutical includes Artemether and Saquinavir.

A further aspect of the present invention includes wherein the pharmaceutical includes Artemether and Remdesivir.

An additional aspect of the present invention includes wherein the pharmaceutical includes Hydroxychloroquine and Atazanavir.

Another aspect of the present invention includes wherein the pharmaceutical includes Hydroxychloroquine and Efavirenz.

A further aspect of the present invention includes wherein the pharmaceutical includes Hydroxychloroquine and Fosamprenavir Calcium.

An additional aspect of the present invention includes wherein the pharmaceutical includes Hydroxychloroquine and Saquinavir.

Another aspect of the present invention includes wherein the pharmaceutical includes Hydroxychloroquine and Remdesivir.

III Methods of Prophylaxis or Treatment of COVID or COVID-19 Using Nanoparticle Formulations That Include Pharmaceutical Compositions The present invention includes methods of prophylaxis or treatment of COVID or COVID-19 using nanoparticle formulations that include pharmaceutical compositions.

A third aspect of the present invention includes methods of prophylaxis or treatment of COVID or COVID-19, including: a) providing a subject in need of the prophylaxis or treatment; b) providing at least one pharmaceutical composition including a combination of nanoparticle formulations, including one or more of the following components: 1) Artemether; 2) Remdesivir (GS-5734); 3) Valsartan; 4) Atazanavir; 5) Digoxin; 6) Teriflunomide; 7) Cyclic Prolyl Glycine; 8) Donepezil; 9) Memantine; 10) Rivastigmine; 11) Galantamine; and 12) a combination thereof; wherein the components are provided together or separately; wherein the components are administered together or separately; and wherein the components are provided in a pharmaceutically acceptable diluent, adjuvant and/or excipient; c) administering a pharmaceutically effective amount of the at least one pharmaceutical composition to the subject; wherein the subject is provided prophylaxis or treatment of COVID-19.

Another aspect of the present invention includes wherein the pharmaceutical composition preferably includes an intranasal formulation preferably including about 10 mg to about 20 mg of Artemether and about 20 mg to about 100 mg of GS-5734, preferably about once or twice per day.

A further aspect of the present invention includes wherein the pharmaceutical composition preferably includes an intranasal formulation preferably includes about 20 mg to about 100 mg of GS-5734 and about 20 mg to about 40 mg of Valsartan, preferably about once or twice per day.

An additional aspect of the present invention includes wherein the pharmaceutical composition preferably includes an intranasal formulation preferably including about 20 mg to about 100 mg of GS-5734 and 10 mg-20 mg of Atazanavir, preferably about once or twice per day.

Another aspect of the present invention includes wherein the pharmaceutical composition preferably includes an intranasal formulation preferably about 20 mg to about 100 mg of GS-5734 and about 0.005 mg/kg to about 0.04 mg/kg of Digoxin, preferably once or twice per day.

A further aspect of the present invention includes wherein the pharmaceutical composition preferably includes an intranasal formulation preferably including about 20 mg to about 100 mg of GS-5734 and 7 mg-14 mg of Teriflunomide, preferably about once or twice per day.

An additional aspect of the present invention includes wherein the pharmaceutical composition preferably includes an intranasal formulation preferably including about 20 mg to about 100 mg of GS-5734 and about 10 mg to about 50 mg of Cyclic Prolyl Glycine, preferably about once or twice per day.

Another aspect of the present invention includes wherein the pharmaceutical composition preferably includes an intranasal formulation preferably including about 20 mg to about 100 mg of GS-5734 and about 0.15 mg to about 1.0 mg/kg of Donepezil, preferably once or twice a day.

A further aspect of the present invention includes wherein the pharmaceutical composition preferably includes an intranasal formulation preferably about 20 mg to about 100 mg of GS-5734 and about 0.15 mg to about 0.50 mg/kg of Memantine, preferably once or twice a day.

An additional aspect of the present invention includes wherein the pharmaceutical composition preferably includes an intranasal formulation preferably including about 20 mg to about 100 mg of GS-5734 and about 0.01 mg to about 0.4 mg/kg of Rivastigmine, preferably once or twice a day.

Another aspect of the present invention includes wherein the pharmaceutical composition preferably includes an intranasal formulation preferably including about 20 mg to about 100 mg of GS-5734 and about 0.20 mg to about 1.00 mg/kg of Galantamine, preferably once or twice a day.

IV Methods of Prophylaxis or Treatment of COVID or COVID-19 Using Combinations of Various Pharmaceutical Compositions The present invention includes methods of prophylaxis or treatment of COVID or COVID-19 using combinations of various pharmaceutical compositions A fourth aspect of the present invention includes methods of prophylaxis or treatment of COVID or COVID-19, including: a) providing a subject in need of said prophylaxis or treatment; b) providing at least one pharmaceutical composition including a combination formulation, including one or more of the following components: 1) Cyclic Prolyl Glycine; 2) Atazanavir; 3) Teriflunomide; 4) Valsartan; 5) Donepezil; 6) Rivastigmine; 7) Memantine; 8) Galantamine; 9) Dexamethasone; 10) GS-5734; 11) Methylprednisolone; 12) Ivermectin; 13) Polio Vaccine; and 14) a combination thereof; wherein the components are provided together or separately; wherein the components are administered together or separately; and wherein the components are provided in a pharmaceutically acceptable diluent, adjuvant and/or excipient; c) administering a pharmaceutically effective amount of the at least one pharmaceutical composition to the subject; wherein the subject is provided prophylaxis or treatment of COVID-19.

Another aspect of the present invention includes wherein the pharmaceutical composition includes an oral formulation preferably including about 10 mg to about 50 mg of Cyclic Prolyl Glycine and about 10 mg to about 20 mg of Atazanavir, preferably about once or twice per day.

A further aspect of the present invention includes wherein the pharmaceutical composition preferably includes an oral formulation including about 10 mg to about 50 mg of Cyclic Prolyl Glycine and about 7 mg to about 14 mg of Teriflunomide, preferably about once or twice per day.

An additional aspect of the present invention includes wherein the pharmaceutical composition preferably includes an oral formulation preferably including about 10 mg to about 50 mg of Cyclic Prolyl Glycine and 80-160 mg of Valsartan, preferably once or twice per day.

Another aspect of the present invention includes wherein the pharmaceutical composition preferably includes an oral formulation preferably including about 10 mg to about 50 mg of Cyclic Prolyl Glycine and about 0.10 to about 1.00 mg/kg of Donepezil, preferably about once or twice per day.

A further aspect of the present invention includes wherein the pharmaceutical composition preferably includes an oral formulation preferably including about 10 mg to about 50 mg of Cyclic Prolyl Glycine and about 0.01 to about 0.10 mg/kg of Rivastigmine, preferably about once or twice per day.

An additional aspect of the present invention includes wherein the pharmaceutical composition preferably includes an oral formulation preferably including about 10 mg to about 50 mg of Cyclic Prolyl Glycine and about 0.20 mg to about 1.00 mg/kg of Memantine, preferably once or twice per day.

Another aspect of the present invention includes wherein the pharmaceutical composition preferably includes an oral formulation preferably including about 10 mg to about 50 mg of Cyclic Prolyl Glycine and about 0.20 mg to about 1.00 mg/kg of Galantamine, preferably about once or twice per day.

A further aspect of the present invention includes wherein the pharmaceutical composition preferably includes an oral formulation preferably including about 10 mg to about 20 mg of Atazanavir and about 0.10 mg to about 1.00 mg/kg of Donepezil, preferably about once or twice per day.

An additional aspect of the present invention includes wherein the pharmaceutical composition preferably includes an oral formulation preferably including about 10 mg to about 20 mg of Atazanavir and about 0.01 to about 0.10 mg/kg of Rivastigmine, preferably about once or twice per day.

Another aspect of the present invention includes wherein the pharmaceutical composition preferably includes an oral formulation preferably including about 10 mg to about 20 mg of Atazanavir and about 0.20 mg to about 1.00 mg/kg of Memantine, preferably about once or twice per day.

A further aspect of the present invention includes wherein the pharmaceutical composition preferably includes an oral formulation preferably including about 10 mg to about 20 mg of Atazanavir and about 0.20 mg to about 1.00 mg/kg of Galantamine, preferably about once or twice per day.

An additional aspect of the present invention includes wherein the pharmaceutical composition preferably includes an oral formulation preferably including about 10 mg to about 20 mg of Atazanavir and about 80 mg to about 160 mg of Valsartan, preferably about once or twice per day.

Another aspect of the present invention includes wherein the pharmaceutical composition preferably includes an oral formulation preferably including about 10 mg to about 20 mg of Atazanavir and about 7 mg to about 14 mg of Teriflunomide, preferably about once or twice per day.

A further aspect of the present invention includes wherein the pharmaceutical composition preferably includes an oral formulation preferably including about 1 mg to about 6 mg of Dexamethasone and about 10 mg to about 50 mg of Cyclic Prolyl Glycine, preferably about once or twice per day.

An additional aspect of the present invention includes wherein the pharmaceutical composition preferably includes an oral formulation including about 1 mg to about 6 mg of Dexamethasone and about 0.15 mg to about 1.00 mg/kg of Donepezil, preferably about once or twice per day.

Another aspect of the present invention includes wherein the pharmaceutical composition preferably includes an oral formulation preferably including about 1 mg to about 6 mg of Dexamethasone and about 10 mg to about 20 mg of Atazanavir, preferably about once or twice per day.

A further aspect of the present invention includes wherein the pharmaceutical composition preferably includes an oral formulation including about 1 mg to about 6 mg of Dexamethasone and about 20 mg to about 100 mg of GS-5734, preferably about once or twice a day.

An additional aspect of the present invention includes wherein the pharmaceutical composition preferably includes an oral formulation preferably including about 8 mg to about 48 mg of Methylprednisolone and about 10 mg to about 50 mg of Cyclic Prolyl Glycine, preferably once or twice per day.

Another aspect of the present invention includes wherein the pharmaceutical composition preferably includes an oral formulation preferably including about 8 mg to about 48 mg of Methylprednisolone and about 0.15 mg to about 1.00 mg/kg of Donepezil, preferably once or twice per day.

A further aspect of the present invention includes wherein the pharmaceutical composition preferably includes an oral formulation preferably including about 1 to about 6 mg of Dexamethasone and about 7 mg to about 14 mg of Teriflunomide, preferably once or twice per day.

An additional aspect of the present invention includes wherein the pharmaceutical composition preferably includes an oral formulation preferably including about 8 mg to about 48 mg of Methylprednisolone and about 7 mg to about 14 mg of Teriflunomide, preferably about once or twice per day.

Another aspect of the present invention includes wherein the pharmaceutical composition preferably includes an oral formulation preferably including about 10 mg to about 50 mg of Cyclic Prolyl Glycine and about 0.4 mg/kg of Ivermectin, preferably about once or twice per day.

An additional aspect of the present invention includes wherein the pharmaceutical composition preferably includes an oral formulation preferably including about 10 mg to about 50 mg of Cyclic Prolyl Glycine and Polio vaccine of about 0.45 ($\log^{10}$ $CCID_{50}/\mu l$ on Day 1 and on Day 28, preferably about once or twice per day.

V Methods of Prophylaxis or Treatment of COVID or COVID-19 Using a Polio Vaccine and Pharmaceutical Compositions.

The present invention includes method of prophylaxis or treatment of COVID or COVID-19 using a polio vaccine and pharmaceutical compositions.

A fifth aspect of the present invention includes methods of prophylaxis or treatment of COVID or COVID-19, including: a) providing a subject in need of said prophylaxis or treatment; b) providing at least one pharmaceutical composition including a combination formulation, including: 1) Cyclic Prolyl Glycine; and 2) Polio Vaccine, preferably oral polio vaccine; wherein the components are provided together or separately; wherein the components are administered together or separately; and wherein the components are provided in a pharmaceutically acceptable diluent, adjuvant and/or excipient; and c) administering a pharmaceutically effective amount of the at least one pharmaceutical composition to said subject; wherein the subject is provided prophylaxis or treatment of COVID-19.

Another aspect of the present invention includes wherein the pharmaceutical preferably includes an oral formulation including about 10 mg to about 50 mg of Cyclic Prolyl Glycine preferably oral and Oral Polio Vaccine at an average dose of about 0.45 ($\log^{10}$ $CCID_{50}/\mu l$), preferably on about Day 1 and on about Day 28.

A further aspect of the present invention includes wherein a second polio vaccination to be carried on about 28 days after the initial vaccination.

VI Detailed Description of Certain Aspects and Embodiments of the Present Invention The present invention is directed in part towards compounds that are effective in preventing and treating a coronavirus infection, particularly coronaviruses, and preferably the severe acute respiratory syndrome and complications caused by SARS-CoV-2 (also known as COVID-19) and COVID in general.

In one aspect, the present invention provides methods for treating a coronavirus infection. A second aspect of the present invention provides prophylaxis methods to prevent Covid-19 infection. The method includes administering to a subject in need of the treatment an effective amount of one or more of the following compounds (including their pharmaceutically acceptable salts and prodrugs):

1. Antimalarial drugs, such as but not limited to: Chloroquine, Hydroxychloroquine, Artemether, Arteether, Artesunate, and Artelininic acid
2. Antiviral drugs, such as but not limited to: Atazanavir, Efavirenz, Fosamprenavir, Saquinavir, Remdesivir (GS-5734), GS-441524. Digoxin, Tipranavir, Abacavir, Nelfinavir, and Oseltamivir.
3. Anti-hypertensive drugs belong to the class of angiotensin II receptor antagonists such as but not limited to Valsartan, Candesartan, Eprosartan, Irbesartan, Losartan, Olmesartan, and Telmisartan.
4. Immunomodulatory drugs such as but not limited to Interferon beta-la, Interferon beta-1b, Teriflunomide, Natalizumab, Glatiramer, and Fingolimod.
5. Neuroprotective drugs such as but not limited to Donepezil, Rivastigmine, Memantine, Galantamine and an endogenous compound found in the animal and human brain, known as Cyclic Prolyl Glycine, and for the prevention and treatment of Covid-19
6. Anti-inflammatory drugs such as but not limited to betamethasone, prednisone, methylprednisolone and dexamethasone
7. Oral Polio Vaccine: The present invention describes a combination of NA-931 with an oral polio vaccine to enhance the effectiveness of the vaccine, while eliminate potential complications including Vaccine-Associated Paralytic Polio (VAPP) as well as Circulating Vaccine-Derived Polioviruses (cVDPVs).

All of the compounds mentioned above except Remdesivir (GS-5734) and Cyclic Prolyl Glycine are FDA approved generic drugs readily available to the public. Remdesivir (GS-5734) has been approved by the FDA for emergency use for treatment of severe cases of Covid-19. Cyclic Prolyl Glycine is an experimental drug for the treatment and or prevention of neurological disorders including Alzheimer's disease, Parkinson's disease, and Huntington's disease, and as anticonvulsants (L. Tran-U.S. Pat. No. 7,232,798).

The present invention describes that a combination of an antimaterial drug such as Hydroxychloroquine or Artemether with an antiviral drug such as Atazanavir as a combination drug therapeutic treatment for Covid-19.

The present invention describes an optional synergy between an antiviral drug and an antimalarial drug that a co-administration of the two drugs enhances the efficacy of a combined therapy for a proposed treatment targeting Covid-19.

The present invention describes a new combination therapy preferably in a form of a gel capsule comprising of Artemether and Remdesivir (GS-5734), which was used as a prophylaxis and treatment of an early onset of Covid-19.

The present invention describes novel nanoparticles preferably based intranasal delivery system for the above drugs and combination drug therapy.

The present invention describes a new combination therapy comprising of an antimalarial drug such as Artemether and an antiviral drug such as Remdesivir (GS-5734) or Atazanavir or Digoxin, as a prophylaxis and treatment of an early onset of Covid-19.

The present invention describes a new combination therapy comprising of Artemether and Atazanavir which was used as a prophylaxis and treatment of an early onset of Covid-19.

The present invention describes an optional synergy between an antiviral drug and an angiotensin II receptor antagonist that a co-administration of the two drugs enhances the efficacy of a combined therapy for a proposed treatment targeting Covid-19.

The present invention describes a new combination therapy comprising of GS-5734 and Valsartan as a prophylaxis and treatment of an early onset of Covid-19.

The present invention describes a new combination therapy comprising of Atazanavir and Valsartan as a prophylaxis and treatment of an early onset of Covid-19.

The present invention describes an optional synergy between two antiviral drugs co-administration of the two drugs enhances the efficacy of a combined therapy for a proposed treatment targeting Covid-19.

The present invention describes a new combination therapy comprising of GS-5734 and Digoxin or GS-5734 and Atazanavir as a prophylaxis and treatment of an early onset of Covid-19.

The present invention describes an optional synergy between an antiviral drug and an immunomodulating drug that a co-administration of the two drugs enhances the efficacy of a combined therapy for a proposed treatment targeting Covid-19.

The present invention describes a new combination therapy comprising of GS-5734 and Teriflunomide which was used as a prophylaxis and treatment of an early onset of Covid-19.

The present invention describes an optional synergy between an antiviral drug and a neuroprotective drug that a co-administration of the two drugs enhances the efficacy of a combined therapy for a proposed treatment targeting Covid-19.

The present invention describes a new combination therapy comprising of GS-5734 and Cyclic Prolyl Glycine as a prophylaxis and treatment of an early onset of Covid-19.

The present invention describes a new combination therapy comprising of GS-5734 and Donepezil as a prophylaxis and treatment of an early onset of Covid-19.

The present invention describes a new combination comprising of GS-5734 and Memantine as a prophylaxis and treatment of an early onset of Covid-19.

The present invention describes a new combination therapy of GS-5734 and Rivastigmine as a prophylaxis and treatment of an early onset of Covid-19.

The present invention describes a new combination therapy comprising of GS-5734 and Galantamine as a prophylaxis and treatment of an early onset of Covid-19.

The present invention describes a new combination therapy comprising of Atazanavir and Donepezil as a prophylaxis and treatment of an early onset of Covid-19.

The present invention describes a new combination comprising of Atazanavir and Memantine as a prophylaxis and treatment of an early onset of Covid-19.

The present invention describes a new combination therapy of Atazanavir and Rivastigmine as a prophylaxis and treatment of an early onset of Covid-19.

The present invention describes a new combination therapy comprising of Atazanavir and Galantamine as a prophylaxis and treatment of an early onset of Covid-19.

The present invention describes a new combination therapy comprising of Atazanavir and Cyclic Prolyl Glycine which was used as a prophylaxis and treatment of an early onset of Covid-19.

The present invention describes an optional synergy between an immunomodulating drug and a neuroprotective drug that a co-administration of the two drugs enhances the efficacy of a combined therapy for a proposed treatment targeting Covid-19.

The present invention describes a new combination therapy comprising of Teriflunomide and Cyclic Prolyl Glycine which was used as a prophylaxis and treatment of an early onset of Covid-19.

The present invention describes an optional synergy between an anti-inflammatory drug and a neuroprotective drug that a co-administration of the two drugs enhances the efficacy of a combined therapy for a proposed treatment targeting Covid-19.

The present invention describes a new combination therapy comprising of Dexamethasone and Cyclic Prolyl Glycine which was used as a prophylaxis and treatment of an early onset of Covid-19.

The present invention describes a new combination therapy comprising of Dexamethasone and Donepezil which was used as a prophylaxis and treatment of an early onset of Covid-19.

The present invention describes a new combination therapy comprising of Methylprednisolone and Cyclic Prolyl Glycine which was used as a prophylaxis and treatment of an early onset of Covid-19.

The present invention describes a new combination therapy comprising of Methylprednisolone and Donepezil which was used as a prophylaxis and treatment of an early onset of Covid-19.

The present invention describes an optional synergy between an anti-inflammatory drug and an anti-viral drug that a co-administration of the two drugs enhances the efficacy of a combined therapy for a proposed treatment targeting Covid-19.

The present invention describes a new combination therapy comprising of Dexamethasone and Atazanavir which was used as a prophylaxis and treatment of an early onset of Covid-19.

The present invention describes a new combination therapy comprising of Dexamethasone and Remdesivir which was used as a prophylaxis and treatment of an early onset of Covid-19.

The present invention describes an optional synergy between an anti-inflammatory drug and an immunomodulating drug that a co-administration of the two drugs enhances the efficacy of a combined therapy for a proposed treatment targeting Covid-19.

The present invention describes a new combination therapy comprising of Dexamethasone and Teriflunomide, which was used as a prophylaxis and treatment of an early onset of Covid-19.

The present invention describes a new combination therapy comprising of Methylprednisolone and Teriflunomide, which was used as a prophylaxis and treatment of an early onset of Covid-19.

The present invention relates to use of one or more compounds mentioned in the summary section above for treating coronavirus infection such as severe acute respiratory syndrome virus infection.

1. Antimalarial Drugs

Chloroquine is a well-known lysosomotropic agent, currently attracting many hopes in terms of antiviral therapy as well as in antitumoral effect because of its pH-dependent inhibiting action on the degradation of cargo delivered to the lysosome, thus effectively disabling this final step of the autophagy pathway.

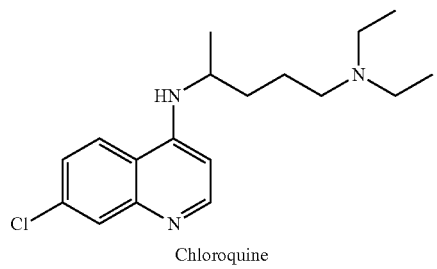 [SMILES: CCN(CC)CCCC(C)Nc1ccnc2cc(Cl)ccc12]

Chloroquine

Chloroquine has been shown to inhibit the replication of SARS-CoV in Vero E6 cells. Since immunopathological factors may play a significant role in SARS-CoV, it will be of interest to further study whether artemether is also effective in terms of modulation of inflammatory responses to SARS-CoV infections.

Hydroxychloroquine is a chemical derivative of chloroquine which features a hydroxylethyl group instead of an ethyl group. It has been suggested that hydroxychloroquine was one-half to two-thirds as effective as chloroquine in treating rheumatologic diseases and one-half as toxic.

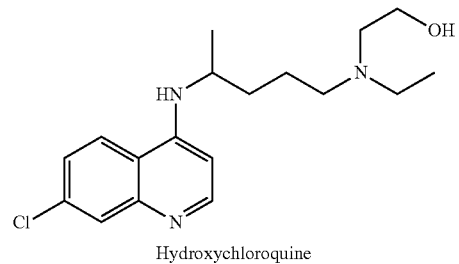 [SMILES: CCN(CCO)CCCC(C)Nc1ccnc2cc(Cl)ccc12]

Hydroxychloroquine

Hydroxychloroquine has been used for over half a century for treating malaria and certain autoimmune disorders such as systemic lupus erythematosus as well as rheumatoid arthritis and Sjogren's Syndrome.

Artemether is a semi-synthetic anti-malarial drugs, a sesquiterpene lactone-bearing 1,2,4-trioxane ring system as the peroxide functional moiety (endoperoxide) within the ring system of a whole molecule. Artemether is derived from the natural product artemisinin, extracted from the plant *Artemisia annua*. It is used for the treatment of erythrocytic stages of chloroquine-resistant *Plasmodium falciparum* and cerebral malaria.

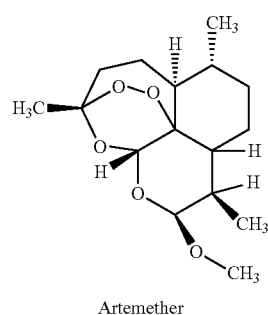

Artemether

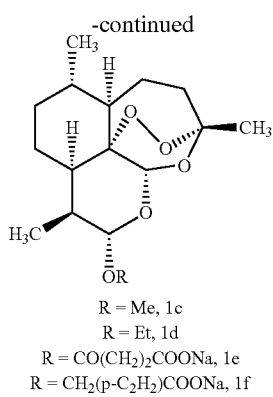

R = Me, 1c
R = Et, 1d
R = CO(CH$_2$)$_2$COONa, 1e
R = CH$_2$(p-C$_2$H$_2$)COONa, 1f

Other derivative drugs of Artemether include arteether (1d), artesunate (1e) and artelininic acid (1f). They are collectively known as the first-generation derivatives of Artemether.

The mechanism of action of artemether and its derivative are believed to be related to endoperoxide bridge in its structure (De Vries P and Dien T. Clinical pharmacology and therapeutic potential of artemisinin and its derivates in the treatment of malaria. Drugs (1996) 52: 818-836).

In the presence of iron, artemisinin and its derivatives are believed to be activated, produce free radicals and cause cell death. Artemisinin and its derivatives have cytotoxic effects against some cancer cell lines such as leukemia, colon cancer, melanoma and breast cancer. Endoperoxide ring is believed to be reductively activated on interaction with heme (Fe(II)) released during parasite Hb digestion, which leads to homolytic cleavage of the peroxide (O—O) bond of trioxanes generating stable cytotoxic species, called carbon-centered free radicals (carbocations) (Parisa Ebrahimisadr, Fatemeh Ghaffarifar, and Zuhair Mohammad Hassan-In-vitro Evaluation of Antileishmanial Activity and Toxicity of Artemether with Focus on its Apoptotic Effect-Iranian Journal of Pharmaceutical Research (2013), 12 (4): 903-909) (Meshnick S R, Yang Y Z, Lima V, Kuypers F, Kamchonwongpaisan S, Yuthavong Y. Iron-dependent free radical generation and the antimalarial artemisinin (qinghaosu). Antimicrob Agents Chemother. 1993; 37(5): 1108-1114).

In the structure of the SARS-CoV-2, the spike (S) glycoprotein responsible for host cell attachment and mediating host cell membrane and viral membrane fusion during infection, is key to the viral life cycle and a major target for antiviral drugs and vaccines. The coronavirus S glycoprotein is synthesized as a precursor protein consisting of ~1,300 amino acids that is then cleaved into an amino (N)-terminal S1 subunit (~700 amino acids) and a carboxyl (C)-terminal S2 subunit (~600 amino acids). Three S1/S2 heterodimers assemble to form a trimer spike protruding from the viral envelope. The S1 subunit contains a receptor-binding domain (RBD), while the S2 subunit contains a hydrophobic fusion peptide and two heptad repeat regions (Li F. Structure, Function, and Evolution of Coronavirus Spike Proteins. Annual review of virology. 2016 08/25; 3(1):237-61. PubMed PMID: PMC5457962. https://doi.org/10.1146/annurev-virology-110615-042301 PMID: 27578435).

The S1/S2 cleavage site of the SARS-CoV S glycoprotein is located after residue 667 of the precursor protein, whereas the S2' cleavage site of the SARSCOV S glycoprotein is on the S2 subunit and is 130 amino acids from the N terminus of the S2 subunit. Cleavage of the S2' site by host cell proteases is required for successful infection by SARS-CoV (Belouzard S, Chu V C, Whittaker G R. Activation of the SARS coronavirus spike protein via sequential proteolytic cleavage at two distinct sites. Proceedings of the National Academy of Sciences of the United States of America. 2009 03/24. 09/26/received; 106(14):5871-6. PubMed PMID: PMC2660061. https://doi.org/10.1073/pnas.0809524106 PMID: 19321428).

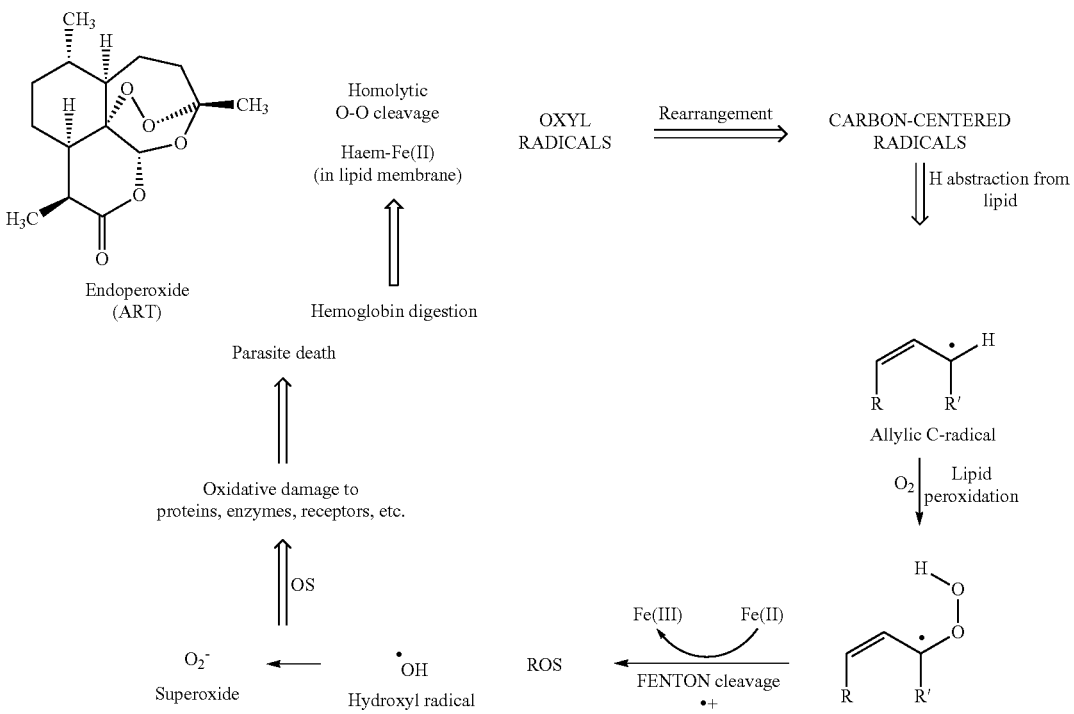

The present invention hypothesizes that the reactive species of Artemether cause membrane damage, alkylation, oxidation of proteins and fats, inhibition of protein and nucleic acid synthesis and interaction with cytochrome oxidase and the glutamine transport system. The free radicals block the activation of toll-like receptors on plasmacytoid dendritic cells (PDCs) on the outer layer of the SARS-CoV-2, thus Artemether plays an important role in stopping the viral life cycle of SARS-CoV-2. However, the present invention is not limited by any mechanism, and any mechanisms presented herein are proposed for illustrative purposes only and not considered binding.

2. Antiviral Drugs

In an effort to fight against Covid-19, an international clinical trial effort has been focused on using antiviral drugs for the treatment of HIV-1 infections. Drug combination such as kglopinavir (LPV)/ritonavir (RTV), in combination or not with interferon-(IFN-), chloroquine (CQ) and remdesivir are under clinical testing for COVID-199. LPV, RTV and remdesivir target viral enzymes, while the actions of CQ and IFN-target host cells. It has been suggested that the most successful antiviral drugs often directly target viral enzymes (Organization, W. H. WHO R&D Blueprint: informal consultation on prioritization of candidate therapeutic agents for use in novel coronavirus 2019 infection, Geneva, Switzerland, 24 Jan. 2020. (2020)).

For coronavirus (CoV), its major protease (Mpro) has been a drug target for almost two decades, starting with early studies on 2002 SARS-CoV that showed this enzyme to be inhibited by LPV/RTV, inhibitors of HIV protease. Mpro is required during the CoV replication cycle to process viral polyprotein (Fehr, A. R. & Perlman, S. Coronaviruses: an overview of their replication and pathogenesis. Methods Mol. Biol. Clifton N J 1282, 1-23 (2015)).

In a combined therapy of LPV with RTV, LPV is included as the principle antiviral compound and RTV as an inhibitor cytochrome p450. However, in an open-label clinical trial using LPV/RTV against COVID-19, their combination showed a limited benefit for treated patients. In the early 2000s, an antiretroviral protease inhibitor, atazanavir (ATV), was suggested to be a possible replacement for rLPV/RTV due to fewer side effects for the patients. ATV has been described to reach the lungs after intravenous administration. Moreover, a proposed secondary use of ATV to treat pulmonary fibrosis suggested that this drug could functionally reach the lungs (Gibert, C. L. Treatment Guidelines for the Use of Antiretroviral Agents in HIV-Infected Adults and Adolescents: An Update. Fed. Pract. 33, 31S-36S (2016)) (Song, S. et al. Protective Effect of Atazanavir Sulphate Against Pulmonary Fibrosis In Vivo and In Vitro. Basic Clin. Pharmacol. Toxicol. 122, 199-207 (2018)).

Atazanavir is an antiretroviral medication used to treat and prevent HIV/AIDS. Atazanavir is a highly active azapeptide inhibitor of the HIV protease. It was the first protease inhibitor designed to be applied once daily (q.d.) and is expected to overcome the problems of earlier agents of this class of drugs, such as unfavorable adverse events like hyperlipidemia, diarrhea and lipodystrophy. Atazanavir can be dosed either at 400 mg q.d. without a pharmacoenhancer as first-line HIV therapy or combined with ritonavir as atazanavir/ritonavir 300/100 mg q.d. for therapy-experienced patients.

Atazanavir sulfate drug information is from the US National Library of Medicine: https://pubchem.ncbi.nlm.nih.gov/compound/Atazanavir-sulfate.

Atazanavir binds to the active site HIV protease and prevents it from cleaving the pro-form of viral proteins into the working machinery of the virus. If the HIV protease enzyme does not work, the virus is not infectious, and no mature virions are made. The azapeptide drug was designed as an analog of the peptide chain substrate that HIV protease would cleave normally into active viral proteins (Lv, Z; Chu, Y; Wang, Y (2015)." HIV protease inhibitors: a review of molecular selectivity and toxicity.". HIV/AIDS-Research and Palliative Care. 7: 95-104. doi: 10.2147/HIV.S79956. PMC 4396582. PMID 25897264]).

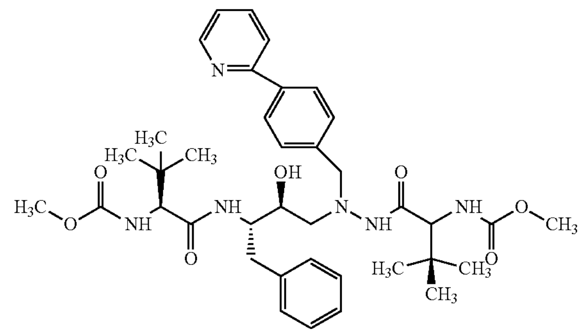

Atazanavir

More specifically, atazanavir is a structural analog of the transition state during which the bond between a phenylalanine and proline is broken. Since humans do not have any enzymes that break bonds between phenylalanine and proline, so this drug will not target human enzymes.

Efavirenz is another antiviral drug that is suitable to be co-administered with an antimalarial drug is Efavirenz. Efavirenz is an antiretroviral medication used to treat and prevent HIV/AIDS. It is generally recommended for use with other antiretrovirals. It may be used for prevention after a needlestick injury or other potential exposure. It is sold both by itself and in combination as efavirenz/emtricitabine/tenofovir. It is taken by mouth once a day.

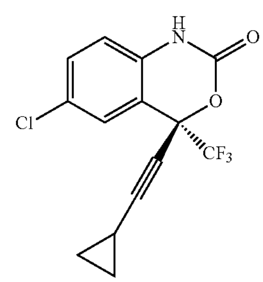

Efavirenz

Efavirenz is also used in combination with other antiretroviral agents as part of an expanded post-exposure prophylaxis regimen to reduce the risk of HIV infection in people exposed to a significant risk (Efavirenz drug information is from the US National Library of Medicine: https://pubchem.ncbi.nlm.nih.gov/compound/64139).

Fosamprenavir is a pro-drug of the protease inhibitor and antiretroviral drug amprenavir. The human body metabolizes Fosamprenavir in order to form amprenavir, which is the active ingredient. That metabolization increases the duration that amprenavir is available, making Fosamprenavir a slow-release version of amprenavir and thus reducing the number of pills required versus standard amprenavir.

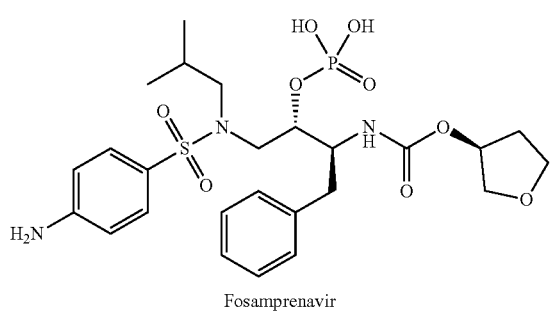 [SMILES: CC(C)CN(C[C@H](OP(=O)(O)O)[C@H](Cc1ccccc1)NC(=O)O[C@H]1CCOC1)S(=O)(=O)c1ccc(N)cc1]

Fosamprenavir

Fosamprenavir is used for the treatment of HIV-1 infections, typically but not necessarily in combination with low-dose ritonavir or other antiviral drugs. Fosamprenavir drug information is from the US National Library of Medicine: https://pubchem.ncbi.nlm.nih.gov/compound/131536

Saquinavir is an antiretroviral drug used together with other medications to treat or prevent HIV/AIDS.

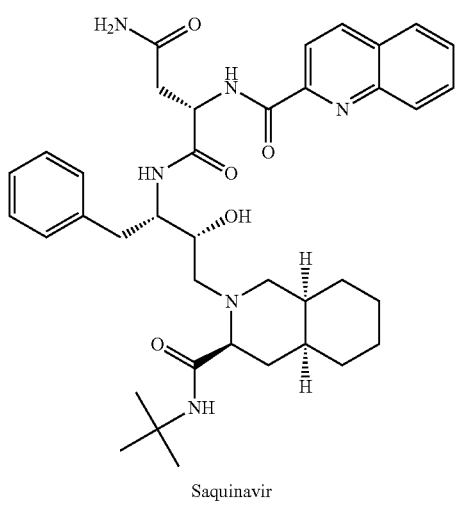 [SMILES: CC(C)(C)NC(=O)[C@@H]1C[C@@H]2CCCC[C@@H]2CN1C[C@@H](O)[C@H](Cc1ccccc1)NC(=O)[C@H](CC(N)=O)NC(=O)c1ccc2ccccc2n1]

Saquinavir

Saquinavir a protease inhibitor. Proteases are enzymes that cleave protein molecules into smaller fragments. HIV protease is vital for both viral replication within the cell and release of mature viral particles from an infected cell. Saquinavir binds to the active site of the viral protease and prevents cleavage of viral polyproteins, preventing maturation of the virus. Saquinavir drug information is from the US National Library of Medicine: https://pubchem.ncbi.nlm.nih.gov/compound/441243

Digoxin cell by endocytosis. Once the viral components are in the intracellular environment and the genome is transcribed, the viral proteins are synthesized using the host cell translational machinery, and the new viral particles are transported to the surface to be released and infect other cells. Targeting host cell components such as Na,K-ATPase is a very promising antiviral strategy in order to minimize the resistance to antiviral drugs, and has been shown to be effective in a broad spectrum of viral species.

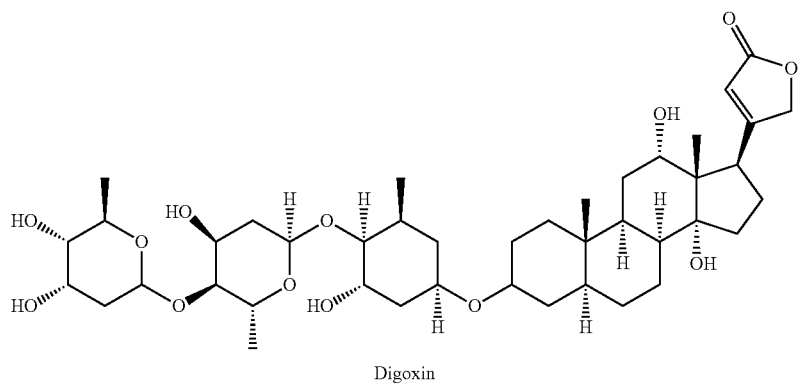

Digoxin

Digoxin drug information is from the US National Library of Medicine: https://pubchem.ncbi.nlm.nih.gov/compound/2724385.

Remdesivir (GS-5734) is a broad-spectrum antiviral drug, specifically an adenosine analog, which inserts into viral RNA chains, interfering with viral replication by causing their premature termination.

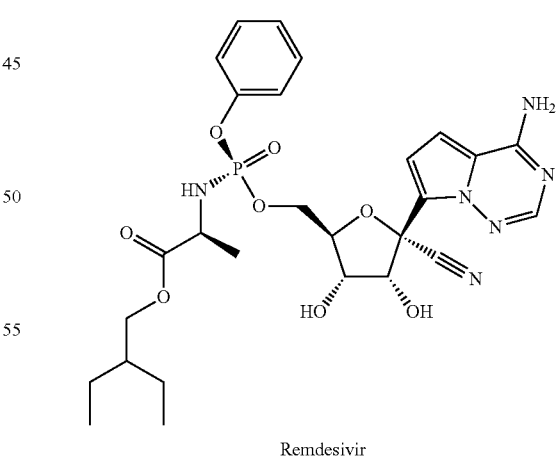

Remdesivir

Remdesivir was originally developed to treat Ebola virus disease and Marburg virus disease but was ineffective for these viral infections.

Remdesivir drug information is from the US National Library of Medicine: https://pubchem.ncbi.nlm.nih.gov/compound/121304016

Early studies demonstrated remdesivir's antiviral activity against several RNA viruses including SARS coronavirus and Middle East respiratory syndrome-related coronavirus, among others. It is administered intravenously (Mehta N, Mazer-Amirshahi M, Alkindi N (April 2020). "Pharmacotherapy in COVID-19; A narrative review for emergency providers". The American Journal of Emergency Medicine: S0735-6757(20)30263-1. doi:10.1016/j.ajem.2020.04.035. PMC 7158837. PMID 32336586) (EP3595672-Methods Of Treating Feline Coronavirus Infections-Application number: 18715335.8, filled on Mar. 13, 2018) (U.S. Pat. No. 10,370, 342-Toll Like Receptor Modulator).

A randomized, double-blind, placebo-controlled, multicenter trial conducted at ten hospitals in Hubei, China between February 6 and March 12 with 237 patients enrolled. This trial is registered with ClinicalTrials.gov, NCT04257656. Remdesivir was stopped early because of adverse events in 18 (12%) patients versus four (5%) patients who stopped placebo early. In this study of adult patients admitted to hospital for severe COVID-19, remdesivir was not associated with statistically significant clinical benefits (Yeming Wang et al. Remdesivir in adults with severe COVID-19: a randomized, double-blind, placebo-controlled, multicenter trial, The Lancet-Published online Apr. 29, 2020 https://doi.org/10.1016/S0140-6736(20)31022-9).

However, a preliminary data analysis from a randomized, controlled trial involving 1063 patients, which began on Feb. 2 2020 showed more positive results. The trial (known as the Adaptive COVID-19 Treatment Trial) (Adaptive COVID-19 Treatment Trial (ACTT)-ClinicalTrials.gov Identifier: NCT04280705-https://clinicaltrials.gov/ct2/show/NCT04280705?term=remdesivir&cond=covid-19&draw=2&rank=9).

Preliminary results indicate that patients who received remdesivir had a 31% faster time to recovery than those who received placebo (p<0.001). Specifically, the median time to recovery was 11 days for patients treated with remdesivir compared with 15 days for those who received placebo. Results also suggested a survival benefit, with a mortality rate of 8.0% for the group receiving remdesivir versus 11.6% for the placebo group (p=0.059) (https://www.niaid.nih.gov/news-events/nih-clinical-trial-shows-remdesivir-accelerates-recovery-advanced-covid-19).

It was observed during the in-vitro experiments that maximal inhibition when the Artemether and Atazanavir were added between 3 hours pre-infection and 3 hours after infection. Less inhibition was detected when the drug was added after 12 hours post-infection (Our observation was consistent with the report by Agostini et al regarding GS-5734 (remdesivir) (Agostini M L, Andres E L, Sims A C, Graham R L, Sheahan T P, Lu X, Smith E C, Case J B, Feng J Y, Jordan R, Ray AS, Cihlar T, Siegel D, Mackman R L, Clarke M O, Baric R S, Denison M R. 2018. Coronavirus susceptibility to the antiviral remdesivir (GS-5734) is mediated by the viral polymerase and the proofreading exoribonuclease. mBio 9:e00221-18. https://doi.org/10.1128/mBio.00221-18.).

GS-441524 is an adenosine nucleotide analog antiviral, similar to remdesivir. GS-441524 continues to be studied in the treatment of Feline Infectious Peritonitis Virus, a coronavirus that only infects cats.

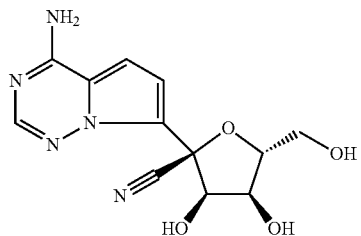

GS-441524

Chemical name: (2R,3R,4S,5R)-2-(4-aminopyrrolo[2,1-f][1,2,4]triazin-7-yl)-3,4-dihydroxy-5-(hydroxymethyl)oxolane-2-carbonitrile GS-441524 drug information is from the US National Library of Medicine: https://pubchem.ncbi.nlm.nih.gov/compound/44468216

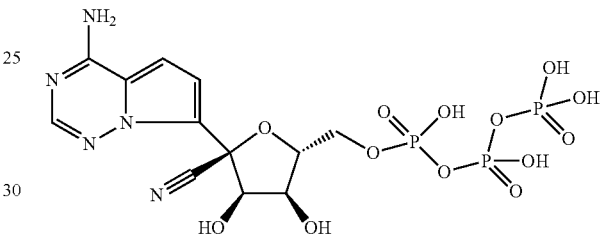

GS-443902

GS-443902 is an organic triphosphate of GS-441524 in which the 5'-hydroxy group has been replaced by a triphosphate group. It is the active metabolite of remdesivir. It has a role as a drug metabolite, an antiviral drug and an anti-coronaviral agent.

Chemical name: [[(2R,3S,4R,5R)-5-(4-aminopyrrolo[2, 1-f][1,2,4]triazin-7-yl)-5-cyano-3,4-dihydroxyoxolan-2-yl] methoxy-hydroxyphosphoryl] phosphono hydrogen phosphate GS-443902 drug information is from the US National Library of Medicine: https://pubchem.ncbi.nlm.nih.gov/compound/56832906

These results demonstrate that the above-mentioned antiviral drugs inhibit Covid-19 at early stage during the infection. Because viral RNA is synthesized early in infection and the drug is implicated in inhibiting viral RNA synthesis (Fehr A R, Perlman S. 2015. Coronaviruses: an overview of their replication and pathogenesis. Methods Mol Biol 1282: 1-23. https://doi.org/10.1007/978-1-4939-2438-7_1).

As a result of our experiments, we postulate that in therapeutic treatment protocol, the above mentioned drugs should be administered in the early onset of the disease preferable within 12 hours from the appearance of the symptoms. This explains why the clinical trials of remdesivir for patients suffered from Covid-19 with severe acute respiratory syndrome in the hospital setting after having the symptoms over 5 days were not effective.

Consequently, a preferred time frame for the treatment of Covid-19 is in the early onset of the disease within 24 hours after the symptoms are observed.

In addition, a prophylaxis method is proposed for first responders, healthcare providers in frequent contact with patients or anyone belong to at risk population should take the medication in a daily basis as prescribed by a physician.

Ivermectin is an orally bioavailable macrocyclic lactone derived from *Streptomyces avermitilis*, with antiparasitic and potential anti-viral activities. Upon administration, ivermectin exerts its anthelmintic effect through binding and activating glutamate-gated chloride channels (GluCls) expressed on nematode neurons and pharyngeal muscle cells. This causes increased permeability of chloride ions, causing a state of hyperpolarization and results in the paralysis and death of the parasite.

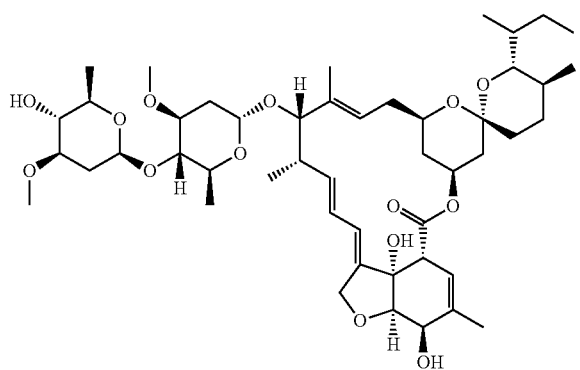 [SMILES: CCC(C)[C@H]1O[C@]2(CC[C@@H]1C)C[C@@H]1C[C@@H](C/C=C(\C)[C@@H](O[C@H]3C[C@H](OC)[C@@H](O[C@H]4C[C@@H](OC)[C@H](O)[C@@H](C)O4)[C@H](C)O3)[C@@H](C)/C=C/C=C3\CO[C@@H]4[C@H](O)C(C)=C[C@@H](C(=O)O1)[C@]34O)O2]

Ivermectin may exert its antiviral effect, including its potential activity against severe acute respiratory syndrome coronavirus-2 (SARS-CoV-2), by binding to the importin (IMP) alpha/beta1 heterodimer, which is responsible for the nuclear import of viral proteins such as the integrase (IN) protein. This inhibits nuclear import of host and viral proteins and may inhibit viral replication.

With the advent of 2020 and the COVID-19 pandemic, ivermectin began garnering attention due to its off-label use for the prophylaxis and treatment of COVID-19. Ivermectin can be used alone or in combination with other compounds and the like in any aspect of the present invention.

3. Angiotensin II Receptor Blockers

Angiotensin II receptor blockers (ARBs), also known AT1 receptor antagonists, are a group of pharmaceuticals that bind to and inhibit the angiotensin II type 1 receptor (AT1) and thereby block the arteriolar contraction and sodium retention effects of renin-angiotensin system. Their main uses are in the treatment of hypertension (high blood pressure), diabetic nephropathy (kidney damage due to diabetes) and congestive heart failure. They selectively block the activation of AT1 receptors, preventing the binding of angiotensin II compared to ACE inhibitors. ARBs and the similar-attributed ACE inhibitors are both indicated as the first-line antihypertensives in patients developing hypertension along with left-sided heart failure. However, ARBs appear to produce less adverse effects compared to ACE inhibitors.

SARS-CoV-2 uses the membrane protein Angiotensin I converting enzyme 2(ACE2) as a cell entry receptor. It was reported that the balance of Renin-Angiotensin System (RAS), regulated by both ACE and ACE2, was altered in COVID-19 patients. It is controversial, whether commonly used anti-hypertensive drugs Angiotensin I converting enzyme inhibitor (ACEI) and Angiotensin II receptor blocker (ARB) can be used in confirmed COVID-19 patients (World Health Organization-Commentaries-May 7, 2020-"COVID-19 and the use of angiotensin-converting enzyme inhibitors and receptor blockers" https://www.who.int/news-room/commentaries/detail/covid-19-and-the-use-of-angiotensin-converting-enzyme-inhibitors-and-receptor-blockers).

The present invention describes the benefits of administering a common anti-hypertensive drug, Valsartan in combination therapy with an antiviral drug (such as Remdesivir) for a potential prevention and treatment of Covid-19.

Valsartan is an orally active nonpeptide triazole-derived antagonist of angiotensin (AT) II with antihypertensive properties. Valsartan selectively and competitively blocks the binding of angiotensin II to the AT1 subtype receptor in vascular smooth muscle and the adrenal gland, preventing AT II-mediated vasoconstriction, aldosterone synthesis and secretion, and renal reabsorption of sodium, and resulting in vasodilation, increased excretion of sodium and water, a reduction in plasma volume, and a reduction in blood pressure.

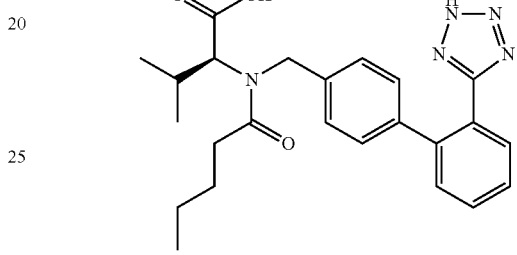

Valsartan

Drug information is from the US National Library of Medicine https://pubchem.ncbi.nlm.nih.gov/compound/60846

4. Immunomodulatory Drugs

Many antiviral drugs are designed to directly limit viral replication. The use of immunomodulating agents might have benefits by controlling the pathological immune response to the virus.

The present invention describes a potential application of IL-6 inhibition and other immunomodulatory agents in the prevention and treatment of Covid-19. We have observed that severe case patients with Covid-19 can develop a syndrome of dysregulated and systemic immune overactivation known as a cytokine storm or hyperinflammatory syndrome that worsens acute respiratory distress syndrome and can lead to multisystem organ failure. There is a lack of preclinical data and clinical data that can establish an association between immunomodulating drugs for the treatment of Covid-19 (Chen G, Wu D, Guo W, et al. Clinical and immunologic features in severe and moderate coronavirus disease 2019. J Clin Invest 2020; published online April 13. DOI:10.1172/JCI137244) (Siddiqi H K, Mehra M R. COVID-19 illness in native and immunosuppressed states: a clinical-therapeutic staging proposal. J Heart Lung Transplant 2020; published online March 20. DOI: 10.1016/j.healun.2020.03.012.).

Teriflunomide is an immunomodulatory drug inhibiting pyrimidine de novo synthesis by blocking the enzyme dihydroorotate dehydrogenase. Teriflunomide may decrease the risk of infections compared to chemotherapy-like drugs because of its more-limited effects on the immune system.

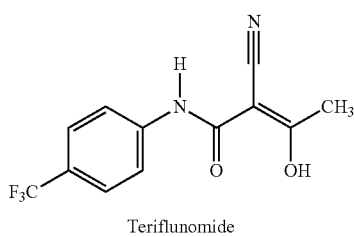 [SMILES: C/C(O)=C(\C#N)C(=O)Nc1ccc(C(F)(F)F)cc1]

Teriflunomide

The present invention describes the usage of Teriflunomide in combinat therapy with an antiviral drug (such as Remdesivir) and a neuroprotect drug for a potential treatment of Covid-19.

Teriflunomide drug information is from the US National Library Medicine: https://pubchem.ncbi.nlm.nih.gov/compound/54684141

5. Neuroprotective Drugs

The SARS-CoV-2 or (Covid-19) virus causes acute, highly lethal pneumonia coronavirus disease with clinical symptoms similar to those reported for SARS-CoV and MERS-CoV. Many patients with COVID-19 also showed neurologic signs, such as headache, nausea, and vomiting. Increasing evidence shows that coronaviruses are not always confined to the respiratory tract and that they may also invade the central nervous system inducing neurological diseases.

A first evidence that SARS-CoV-2 has directly invaded the nervous system was reported by Zhou L. et al. Gene sequencing confirmed the presence of SARS-CoV-2 in the cerebrospinal fluid of a 56-year-old patient with in Beijing Ditan Hospital on Mar. 4, 2020. The patient was diagnosed with viral encephalitis, and the patient's central nervous system was attacked by SARS-CoV-2. This indicates that SARS-CoV-2 can directly invade the nervous system of patients, instead of injuring the nervous system through the immune response to SARS-CoV-2 (Zhou L, Zhang M, Wang J, Gao J. Sars-Cov-2: underestimated damage to nervous system. Travel Med Infect Dis. 2020; 101642.).

A growing body of evidence shows that neurotropism is one common feature of CoVs (Wang D, Hu B, Hu C, et al. Clinical characteristics of 138 hospitalized patients with 2019 novel coronavirus-infected pneumonia in Wuhan China. JAMA. 2020. https://doi.org/10.1001/jama.2020.1585).

Such neuroinvasive propensity of CoVs has been documented almost for all the βCoVs, including SARS-CoV, MERS—CoV, HCoV-229E, and HCoV-OC43 (Talbot P J, Ekandé S, Cashman N R, Mounir S, Stewart J N. Neurotropism of human coronavirus 229E. Adv Exp Med Biol. 1993; 342: 339-346) (Li Y C, Bai W Z, Hirano N, et al. Neurotropic virus tracing suggests a membranous-coating-mediated mechanism for transsynaptic communication. J Comp Neurol. 2013; 521: 203-212).

Early in 2002 and 2003, studies on the samples from patients with SARS have demonstrated the presence of SARS-CoV particles in the brain, where they were located almost exclusively in the neurons (Xu J, Zhong S, Liu J, et al. Detection of severe acute respiratory syndrome coronavirus in the brain: potential role of the chemokine in pathogenesis. Clin Infect Dis. 2005; 41: 1089-1096.) (Netland J, Meyerholz D K, Moore S, Cassell M, Perlman S. Severe acute respiratory syndrome coronavirus infection causes neuronal death in the absence of encephalitis in mice transgenic for human ACE2. J Virol. 2008; 82: 7264-7275.).

Experimental studies using transgenic mice further revealed that either SARS-CoV or MERS-CoV, when given intranasally, could enter the brain, possibly via the olfactory nerves, and thereafter rapidly spread to some specific brain areas including thalamus and brainstem. Among the involved brain areas, the brainstem has been demonstrated to be heavily infected by SARS-CoV or MERS-CoV. Increasing evidence shows that CoVs may first invade peripheral nerve terminals, and then gain access to the CNS via a synapse-connected route (Matsuda K, Park C H, Sunden Y, et al. The vagus nerve is one route of transneural invasion for intranasally inoculated influenza a virus in mice. Vet Pathol. 2004; 41: 101-107.).

There are at least four possible pathogenic mechanisms that may account for the detrimental effect of COVID-19 on the CNS: (1) direct viral encephalitis, (2) systemic inflammation, (3) peripheral organ dysfunction (liver, kidney, lung), and (4) cerebrovascular changes. In most cases, however, neurological manifestations of COVID-19 may arise from a combination of the above.

Based on an epidemiological survey on COVID-19, the median time from the first symptom to dyspnea was 5.0 days, to hospital admission was 7.0 days, and to the intensive care was 8.0 days. Therefore, the latency period may be enough for the virus to enter and destroy the medullary neurons. SARS-CoV-2 may infect nervous system and skeletal muscle as well as the respiratory tract. In a case series of 214 patients with coronavirus disease 2019, neurologic symptoms were seen in 36.4% of patients and were more common in patients with severe infection (45.5%) according to their respiratory status, which included acute cerebrovascular events, impaired consciousness, and muscle injury. In patients with severe COVID-19, rapid clinical deterioration or worsening could be associated with a neurologic event such as stroke, which would contribute to its high mortality rate (Mao L, Wang M, Chen S, He Q, Chang J, Hong C, Zhou Y, Wang D, Li Y, Jin H, Hu B. Neurological Manifestations of Hospitalized Patients with COVID-19 in Wuhan, China: a retrospective case series study. MedRxiv. https://doi.org/10.1101/2020.02.22.20026500) (Mao L, Jin H, Wang M, Hu Y, Chen S, He Q, et al. Neurologic manifestations of hospitalized patients with coronavirus disease 2019 in Wuhan, China. JAMA Neurol. 2020: e201127).

Any one or a combination of these mechanisms put Covid-19 survivors at risk for developing long-term neurological consequences, either by aggravating a preexisting neurological disorder or by initiating a new disorder. This concern is supported by findings that show that one third of patients at the time of discharge have evidence of cognitive impairment and motor deficits (Helms J, Kremer S, Merdji H, Clere-Jehl R, Schenck M, Kummerlen C, et al.Neurologic features in severe SARS-CoV-2 infection. N Engl J Med. 2020:NEJMc2008597)

Heneka et al suggests that patients surviving COVID-19 are at high risk for subsequent development of neurological disease and in particular Alzheimer's disease (Heneka et al. Alzheimer's Research & Therapy (2020) 12:69).

One objective of the present invention is to develop neuroprotective interventions during the severe acute respiratory syndrome, and provide appropriate rehabilitation measures afterwards. These include early identification of patients at risk; diagnosis of Covid-19-associated encephalopathy which has been underestimated in patients recovered from Covid-19 infection.

The present invention describes the usage of a neuroprotective drug in combination therapy with an antiviral drug such as Remdesivir or Atazanavir for a potential prevention and treatment of Covid-19.

Cyclic Prolyl Glycine and analogs and mimetics thereof has been studied as neuroprotective agents for the treatment and or prevention of neurological disorders including Alzheimer's disease, Parkinson's disease, and Huntington's disease, and as anticonvulsants. (L. Tran-U.S. Pat. No. 7,232,798).

The present invention relates to the use of Cyclic Prolyl Glycine("cyclic GP" or "cPG") and cPG analogues and cPG compounds (showed below), in the treatment and prevention of Covid-19. The present invention also generally relates to materials and methods of regenerating neurons and glial cells or a method of repairing damaged neurons and glial cells caused by Covid-19 infection.

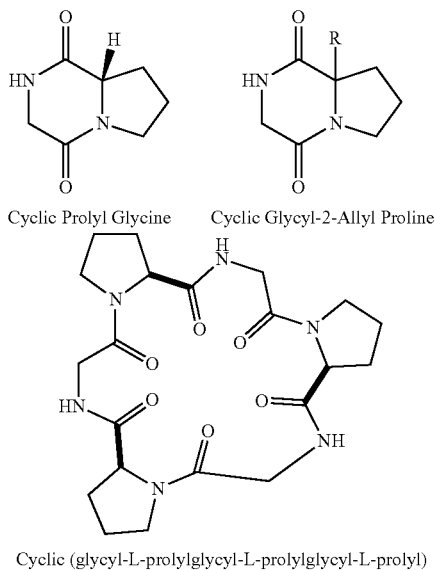

Cyclic Prolyl Glycine     Cyclic Glycyl-2-Allyl Proline

Cyclic (glycyl-L-prolylglycyl-L-prolylglycyl-L-prolyl)

The present invention describes the use a neuroprotective drug such as but not limited to four FDA approved drugs for Alzheimer's disease symptoms modifying drugs: Donepezil, Rivastigmine, Memantine, and Galantamine in the prevention and treatment of Covid-19.

These drugs may help reduce some symptoms and help control some behavioral symptoms.

Donepezil is indicated for the management of mild to moderate Alzheimer's disease.

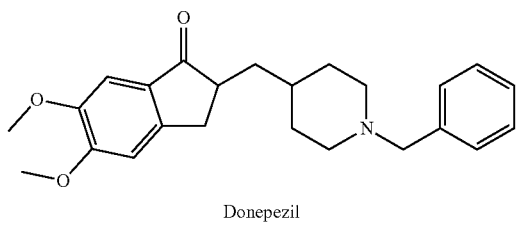 [SMILES: COc1cc2c(cc1OC)C(=O)C(CC1CCN(Cc3ccccc3)CC1)C2]

Donepezil

Donepezil is the hydrochloride salt of a piperidine derivative with neurocognitive-enhancing activity. https://pubchem.ncbi.nlm.nih.gov/compound/3152

Memantine is used to manage moderate to severe Alzheimer's dementia.

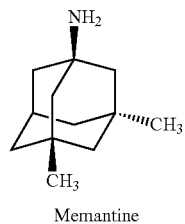

Memantine

A more recent systemic review and meta-analysis indicates that memantine is beneficial as a first line drug for the treatment of Alzheimer's dementia. https://pubchem.ncbi.nlm.nih.gov/compound/4054

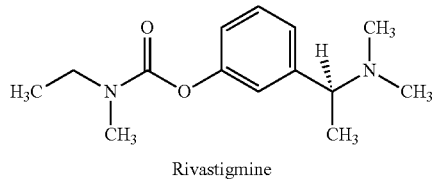 [SMILES: CCN(C)C(=O)Oc1cccc([C@H](C)N(C)C)c1]

Rivastigmine

Rivastigmine is an oral acetylcholinesterase inhibitor used for therapy of Alzheimer disease serum enzyme elevations during therapy and is a rare cause of clinically apparent liver injury. https://pubchem.ncbi.nlm.nih.gov/compound/77991

Galantamine is an oral acetylcholinesterase inhibitor used for therapy of Alzheimer disease

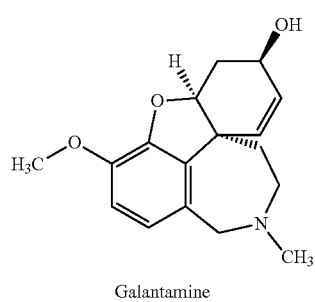

Galantamine

Galantamine is associated with a minimal rate of serum enzyme elevations during therapy and has not been implicated as a cause of clinically apparent liver injury. https://pubchem.ncbi.nlm.nih.gov/compound/9651

The common mechanism of action of the above Alzheimer's drugs are centered on enhancing neurotransmission. Nerve cells communicate with one another using signaling molecules called neurotransmitters; as these molecules are released from nerve cells they diffuse to neighboring cells, stimulating a response upon arrival. One such signaling molecule is acetylcholine, released by nerve cells via synapses to make possible communication between neurons. A fundamental hallmark of neurodegenerative diseases is the deterioration and impairment of the neurotransmission in the neuronal process.

It has been known that systemic inflammation has been shown to cause cognitive decline and neurodegenerative disease makes it likely that COVID-19 survivors will experience neurodegeneration in the following years (Widmann C N, Heneka M T. Long-term cerebral consequences of sepsis. Lancet Neurol. 2014; 13(6):630-6).

The present invention also generally relates to materials and methods of repairing and restoring damaged neurons and the central nervous system for patients recovering from the Covid-19 infection.

6. Anti-Inflammatory Drugs

Anti-inflammatory drugs are synthetic corticosteroids including the following FDA approved generic drugs: betamethasone, prednisone, methylprednisolone and dexamethasone Corticosteroids are naturally-occurring chemicals produced by the adrenal glands located adjacent to the kidneys. Corticosteroids affect metabolism in various ways and modify the immune system. Corticosteroids also block inflammation and are used in a wide variety of inflammatory diseases affecting many organs.

The present invention focuses on dexamethasone as a representative drug of the class of anti-inflammatory drugs.

Dexamethasone is a glucocorticoid agonist. It is used for its anti-inflammatory or immunosuppressive properties and ability to penetrate the CNS, dexamethasone is used alone to manage cerebral edema and with tobramycin to treat corticosteroid-responsive inflammatory ocular conditions.

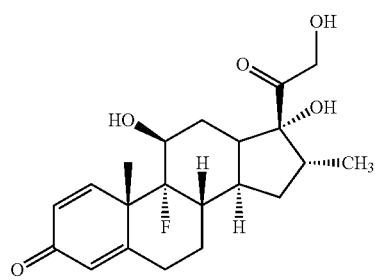

The anti-inflammatory actions of dexamethasone are thought to involve phospholipase A2 inhibitory proteins, lipocortins, which control the biosynthesis of potent mediators of inflammation such as prostaglandins and leukotrienes. Dexamethasone has been shown to exhibit anesthetic, anti-Dexamethasone microbial, appetite stimulant, muscle building and sedative functions. https://pubchem.ncbi.nlm.nih.gov/compound/5743

Among steroids, dexamethasone is also known for its speed of action, greater potency compared to other steroids, as well as length and duration of clinical effects. Its potency is about 20-30 times that of hydrocortisone and 4-5 times of prednisone.

Recommended dosage of Dexamethasone: 0.5, 0.75, 1, 1.5, 2, 4, and 6 mg in tablet form.

Methylprednisolone was approved by the FDA approved methylprednisolone in October 1955.

Like most adrenocortical steroids, methylprednisolone is typically used for its anti-inflammatory effects.

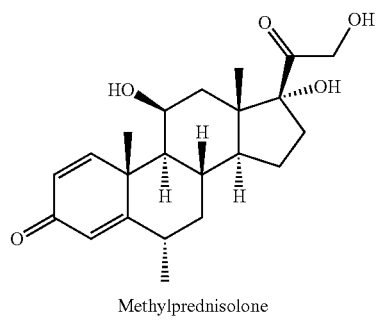

Methylprednisolone

However, glucocorticoids have a wide range of effects, including changes to metabolism and immune responses. Common uses include arthritis therapy and short-term treatment of bronchial inflammation or acute bronchitis due to various respiratory diseases. It is used both in the treatment of acute periods and long-term management of autoimmune diseases, most notably systemic lupus erythematosus.

The initial dosage of Methylprednisolone tablets may vary from 4 mg to 48 mg of methylprednisolone per day depending on the specific disease entity being treated https://pubchem.ncbi.nlm.nih.gov/compound/6741

7. Polio Vaccine:

Three serotypes exist for poliovirus: Wild-type (WT) 1 (WPV1), WT 2 (WPV2) and WT 3 (WPV3) are considered eradicated, but WPV1 still circulates, causing disease in Afghanistan, Pakistan, and Nigeria. (Polio Global Eradication Initiative, 2020). The two Polio vaccines, live attenuated oral poliovirus vaccine (OPV) and inactivated poliovirus vaccine (IPV), are used to protect against polio. The oral poliovirus vaccine (OPV) developed by Albert Sabin in the 1950s have many advantages for use in polio eradication.

In most countries, a combination of bivalent OPV (type 1 and type 3) and IPV is used. OPV is cheaper than IPV. It replicates in the recipient's gut, eliciting superior primary intestinal immunity, compared with IPV, and thus is more effective to prevent transmission of wild viruses. OPV confers contact immunity through indirect immunization of unvaccinated persons from viruses shed by vaccinees and it is administered in oral drops, which makes it easier to administer, store, and transport than IPV injections (Burns, C. C., Diop, O. M., Sutter, R. W., and Kew, O. M. (2014). Vaccine-derived polioviruses. J. Infect. Dis. 210 (Suppl 1), S283-S293).

Early clinical studies showed that besides protecting against poliomyelitis, OPV reduced the number of other viruses that could be isolated from immunized children, compared with placebo recipients.

Both poliovirus and coronavirus are positive-strand RNA viruses; therefore, it is likely that they may induce and be affected by common innate immunity mechanisms. Recent reports indicate that COVID-19 may result in suppressed innate immune responses.

Cytotoxic lymphocytes such as cytotoxic T lymphocytes (CTLs) and natural killer (NK) cells are necessary for the control of viral infection, and the functional exhaustion of cytotoxic lymphocytes is correlated with disease progression. Zheng et al showed that the total number of NK and CD8+ T cells was decreased markedly in patients with SARS-CoV-2 infection. The function of NK and CD8+ T cells was exhausted with the increased expression of NKG2A in COVID-19 patients. Importantly, in patients convalescing after therapy, the number of NK and CD8+ T cells was restored with reduced expression of NKG2A. These results suggest that the functional exhaustion of cytotoxic lymphocytes is associated with SRAS-CoV-2 infection. Hence, SARS-CoV-2 infection may break down antiviral immunity at an early stage (M. Zheng et al-Functional exhaustion of antiviral lymphocytes in COVID-19 patients Cellular & Molecular Immunology (2020) 17:533-535; https://doi.org/10.1038/s41423-020-0402-2).

Therefore, stimulation by live attenuated vaccines could increase resistance to infection by the causal virus, severe acute respiratory syndrome-coronavirus 2 (SARSCoV-2).

Despite its many advantages, use of OPV carries certain liabilities. The first, the rare occurrence of cases of vaccine-associated paralytic poliomyelitis (VAPP) among OPV recipients and their contacts, was recognized soon after licensure and widespread use of OPV in the early 1960s (Henderson D. A, Witte J. J., Morris L., Langmuir A. D. Paralytic disease associated with oral polio vaccines. J. Am Med Assoc 1964; 190:41-8.) (Cochi S. L., Jafai H. S., Armstrong G. L., et al .A world without polio .J. Infect Dis 2014; 210(suppl 1):S1-11.).

In regions with low vaccine coverage, poliomyelitis outbreaks associated with circulating vaccine-derived polioviruses (cVDPVs) have been reported over the past two decades (Stern, A., Yeh, M. T., Zinger, T., Smith, M., Wright, C., Ling, G., Nielsen, R., Macadam, A., and Andino, R. (2017). The Evolutionary Pathway to Virulence of an RNA Virus. Cell 169, 35-46.e19).

Furthermore, virulent cVDPVs circulate and persist for years in the environment and the community, often subclinically, providing a dangerous, "silent" reservoir of virus (Thompson, K. M., and Kalkowska, D. A. (2019). Logistical challenges and assumptions for modeling the failure of global cessation of oral poliovirus vaccine (OPV). Expert Rev. Vaccines 18, 725-736.).

Trends in VAPP epidemiology varied by country income level. In the low-income country, the majority of cases occurred in individuals who had received >3 doses of OPV (63%), whereas in middle and high-income countries, most cases occurred in recipients after their first OPV dose or unvaccinated contacts (81%). Using all risk estimates, VAPP risk was 4.7 cases per million births (range, 2.4-9.7) (Platt, L. R., Estivariz, C. F., and Sutter, R. W. (2014). Vaccine-associated paralytic poliomyelitis: a review of the epidemiology and estimation of the global burden. J. Infect. Dis. 210 (Suppl 1), S380-S389.).

Circulation of cVDPV2 constitutes a significant challenge and a major risk for global health, and has appropriately been designated as a Public Health Emergency of International Concern (Polio Global Eradication Initiative, 2020). On the other hand, IPV, an excellent tool to prevent paralytic poliomyelitis in vaccine recipients, is ineffective in preventing poliovirus transmission and combating epidemics in settings of poor hygiene and sanitation because it induces minimal intestinal mucosal immunity (Bandyopadhyay, A. S., Garon, J., Seib, K., and Orenstein, W. A. (2015). Polio vaccination: past, present and future. Future Microbiol. 10, 791-808.).

When wild polio virus (PV) transmission has been interrupted, the World Health Organization proposes ending the global routine OPV to prevent the risk for vaccine-associated paralyticpoliomyelitis, chronic infection of immunodeficient per-sons, and the reestablishment of poliomyelitis through circulating vaccine-derived polio virus. The conclusion of the WHO was that it would be appropriate, and possibly essential, to develop a drug therapeutic drugs for polio virus infection, as an additional tool to address the problems that might arise in the "postpolio" era. The therapeutic agents do not confer immunity but could be used prophylactically as well as therapeutically. They could protect inactivated polio vaccine (IPV) recipients from PV infection, limit spread until immunity can be ensured and help clear vaccine-derived PV from persistently infected persons (Aylward R B, Sutter R W, Heymann D L. Policy. OPV cessation—the final step to a "polio-free" world. Science. 2005; 310:625-6.).

One aspect of the present invention is the combination of NA-831 in combination with of an oral polio vaccine or an inactivated Polio vaccine thereof to enhance the effectiveness of the vaccine, while eliminate the potential risks caused by VAPP and cVDPVs for the prevention and treatment COVID-19.

The strategy of using OPV inducing nonspecific protection may even have an advantage over a SARS-CoV-2-specific vaccine if SARS-CoV-2 undergoes mutation that leads to antigenic drift (and loss of vaccine efficacy), similar to seasonal influenza viruses. If proven to be effective against COVID-19 in the clinical trials, emergency immunization with live attenuated vaccines could be used for protection against other unrelated emerging pathogens.

8. Combination Therapy

Since coronaviruses constantly mutate, the effectiveness of existing antiviral drugs that target viral proteins, will be severely undermined by the global rise of drug-resistant isolates. Most antiviral therapies have focused on inhibition of viral replication, but do not address bacterial pneumonia and/or hypercytokinemia. Therefore, combination therapy consisting of antiviral drugs with antimalarial agents may improve clinical outcomes in some high-risk patient populations.

One antiviral-drug candidate against Covid-19 is a combination of the HIV protease inhibitors lopinavir and ritonavir. Lopinavir together with another antiviral drug, ritonavir, which increases drug bioavailability, was in clinical trials, along with the immunomodulator interferon beta-1b, for the treatment of Middle East respiratory syndrome (MERS). The two antiviral drugs, lopinavir-ritonavir is particularly attractive because they are is widely available and manufacturable to scale and that it could be prescribed. Unfortunately, lopinavir-ritonavir was not effective for Covid-19 (Cao B et al. Lopinavir-ritonavir in adults hospitalized with severe Covid-19. N Engl J Med 2020 Mar. 18; (e-pub). (https://doi.org/10.1056/NEJMoa2001282)).

The present invention provides an optional synergic between an antiviral drug and an antimalarial drug that a co-administration of the two drugs enhances the efficacy of a proposed treatment targeting Covid-19.

The present invention provides an optional synergic between an antiviral drug and a neuroprotective drug that a co-administration of the two drugs enhances the efficacy of a proposed treatment targeting Covid-19.

The present invention provides an optional synergy between an antiviral drug and an angiotensin II receptor antagonist that a co-administration of the two drugs enhances the efficacy of a combined therapy for a proposed treatment targeting Covid-19.

The present invention provides an optional synergy between two antiviral drugs co-administration of the two drugs enhances the efficacy of a combined therapy for a proposed treatment targeting Covid-19.

The present invention provides an optional synergy between an antiviral drug and an immunomodulating drug that a co-administration of the two drugs enhances the efficacy of a combined therapy for a proposed treatment targeting Covid-19.

9. Optional Synergy of Co-Administration of an Antimalarial Drug and an Antiviral Drug According to an aspect of some embodiments of the present invention there is provided a use of a therapeutically effective amount of an antimalarial drug such as but not limited to artemether in combination with an antiviral drug, such as but not limited to atazanavir sulfate or a pharmaceutically acceptable salt thereof that can be used in the manufacture of a medicament for treating severe acute respiratory syndrome (SARS) related disease particularly COVID-19.

Chloroquine has been commonly used as an antimalarial drug due to its rapid onset of action, easy use, and low cost. However, the resistance to chloroquine developed by the malaria parasite Plasmodium falciparum has significantly reduced the efficacy of the drug. Human immunodeficiency virus protease inhibitors (HIV PIs) can directly inhibit the growth of P. falciparum in vitro at or below the concentrations found in human plasma after oral drug administration (Andrews, K. T., D. P. Fairlie, P. K. Madala, J. Ray, D. M. Wyatt, P. M. Hilton, L. A. Melville, L. Beattie, D. L. Gardiner, R. C. Reid, M. J. Stoermer, T. Skinner-Adams, C. Berry, and J. S. McCarthy. 2006. Potencies of human immunodeficiency virus protease inhibitors in vitro against Plasmodium falciparum and in vivo against murine malaria. Antimicrob. Agents Chemother. 50:639-648).

The optional synergy of the activities between antimalarial drugs and various human immunodeficiency virus protease inhibitors in chloroquine-resistant and sensitive malaria parasites were reported (Zhengxiang He, Li Qin, Lili Chen, Nanzheng Peng, Jianlan You, and Xiaoping Chen-Synergy of Human Immunodeficiency Virus Protease Inhibitors with Chloroquine against Plasmodium falciparum In Vitro and Plasmodium chabaudi In Vivo. Antimicrobial Agents And Chemotherapy, July 2008, p. 2653-2656 Vol. 52, No. 7 0066-4804 doi: 10.1128/AAC.01329-07).

As of Apr. 14, 2020, chloroquine, hydroxychloroquine and azithromycin are being used to treat and prevent COVID-19 despite weak evidence for effectiveness. However, a review published by the Canadian Medical Association Journal on Apr. 8, 2002 warned physicians and patients should be aware of the drugs' potentially serious adverse events.

Potential adverse effects include, cardiac arrhythmias, hypoglycemia, neuropsychiatric effects, such as agitation, confusion, hallucinations and paranoia, interactions with other drugs, metabolic variability, overdose (chloroquine and hydroxychloroquine are highly toxic in overdose and can cause seizures, coma and cardiac arrest) (David N. Juurlink-Safety considerations with chloroquine, hydroxychloroquine and azithromycin in the management of SARS-CoV-2 infection CMAJ 2020. doi: 10.1503/cmaj.200528; early-released Apr. 8, 2020).

Because HIV PIs have relatively short half-lives, it might be beneficial to use these PIs with an antimalarial drug to prevent recrudescence. Therefore, co-administration of a HIV PI and an antimalarial drug may enhance the efficacies of the two groups of drugs in patients.

Herein, the term "antiviral agent" encompasses any active compound or mixture of active compounds which is active against viruses, in particular HCV, and includes, but is not limited to, atazanavir sulfate and derivatives, ribavirin and derivatives and prodrugs thereof (for example, viramidine); interferons (for example, interferon-. alpha.); viral protease inhibitors (for example, boceprevir, SCH 503034, telaprevir, ITMN B, BILN 2061, SCH 6); NS4A inhibitors (for example, GS-9132); NS5A inhibitors; viral polymerase inhibitors, including nucleoside and non-nucleoside polymerase inhibitors (for example, NM-107 and its prodrug valopicitabine (NM-283), R1626/R1479, HCV-796, BILB 1941, R7128/PSI6130, GSK625433, A-848837, BCX-4678, GL59728, GL60667, NV-008, HCV-086, R803, JTK 003, XTL-2125); cyclophilin B inhibitors (for example, alisporivir (DEBIO-025), NIM811); helicase inhibitors (for example, QU665); glycosylation inhibitors (for example, celgosivir (MX-3253)); an antiphospholipid antibody (for example bavituximab); and any combination thereof.

10. Antiviral Drugs Working in Optional Synergy with Antimalarial Drugs Used in the Present Invention Entry/fusion inhibitors:
    gp41 (Enfuvirtide (ENF, T-20)), CCR5 (Maraviroc (MVC), Vicriviroc, Cenicriviroc, Ibalizumab, Fostemsavir Reverse-transcriptase inhibitors (RTIs):
    Nucleoside reverse-transcriptase inhibitors (NNRTI):
        Abacavir, Didanosine, Emtricitabine, Lamivudine, Stavudine, Zidovudine, Amdoxovir, Apricitabine, Censavudine, Elvucitabine, Islatravir, Racivir, Stampidine, Zalcitabine, Tenofovir disoproxil, Tenofovir alafenamide Non-nucleoside reverse-transcriptase inhibitors (NNRTI):
    1 st generation: Efavirenz, Nevirapine, Delavirdine;
    2nd generation: diarylpyrimidines, Etravirine, Rilpivirine, Doravirine Integrase inhibitors:
    Dolutegravir, Elvitegravir, Raltegravir, BI 224436, Cabotegravir, Bictegravir, MK-2048

Maturation inhibitors:
    Bevirimat, BMS-955176

Protease Inhibitors:
    1st generation: Amprenavir, Fosamprenavir, Indinavir, Lopinavir, Nelfinavir, Ritonavir, Saquinavir,
    2nd generation: Atazanavir, Darunavir, Tipranavir, TMC-310911

11. Manufacturing Method of a combined Artemether/Lumefantrine and Remdesivir

The present invention describes a new combination therapy in a form of a gel capsule comprising of 20 mg of Artemether and 100 mg of Remdesivir, which was used as a prophylaxis and treatment of an early onset of Covid-19.

Artemether has been approved by the FDA and is available in a tablet form with Lumefantrine (20 mg artemether and 120 mg lumefantrine). As Artemether is sparingly soluble in water and as Lumefantrine is insoluble in water, the medicament does not dissolve in body fluid easily and efficaciously.

An obvious advantage of formulating the medications in a solid table form is low cost. However, one of the major problems of solid dosage form for Artemether/Lumefantrine is the lack of desired bioavailability of the medicament in the plasma of the blood. In addition, the binding agents in the tablet tend to bind the medicament powder strongly, and the disintegration of the tablet in body fluids is complicated and difficult with the ageing of the tablet.

Remdesivir is only available in the intravenous formulation and for late stage Covid-19 severe acute respiratory syndrome. It is highly desirable to have remdesivir in an oral dosage form for prophylaxis and treatment of early onset of the disease at home or in alternative care setting. Remdesivir is sparingly soluble in water, and its solubility in water is 0.33 mg/ml.

Brief Description Of The Artemether/Lumefantrine-Remdesivir Capsule

The present invention proposes a general method of manufacturing arteether/lumefantrine and remdesivir in soft gelatin capsules. Soft gelatin capsules are hermetically sealed one piece capsule with a liquid or semisolid fill of the medicaments within it. They consist of two major components, the gelatin shell and the medicament which is filled within it. A medicament which is filled within the soft gelatin capsule is in a liquid form.

The present invention can utilize the method described in the Patent Application WO2011141935A2 "Soft capsular preparation of artemether and lumefantrine and process to manufacture same", except the present invention summarizes the process of manufacturing a gel capsule of three active drug ingredients: Artemether, Lumefantrine, Remdesivir.

The soft gel capsule of Artemether and Lumefantrine is comprised: Artemether 4 to 5% w/w, Lumefantrine 20-24% w/w, Remdesivir 18-20%, non-aqueous vehicle 15-20% w/w, preservative less than 1% w/w, viscosity imparting agent 15-20% w/w, suspending agent 1 to 5% w/w and emulsifying agent 1 to 3% w/w and a process to manufacture the said preparation comprising of the following steps as given in the above Patent.

(a) Preservatives and Solid Suspending Agents were milled and sifted.

(b) Non-aqueous vehicle, viscosity imparting agent and liquid suspending agents were filtered to remove the foreign particles (c) Additional steps for mixing preservatives and suspending agents:

(i) Preservatives were dissolved in non-aqueous vehicle;

(ii) Emulsifying agents were warmed and/or melted and added into mixture in (i) above;

(iii) Viscosity imparting agent is added to mixture of (ii) above and the resultant mixture is stirred.

(iv) Suspending agent is added and mixed with the mixture in (iii) above; and (v) The mixture of (a) above and (c) (iv) above was homogenized.

(d) The mixture in (v) above was the encapsulated in soft gelatin.

The suspending agents are Titanium dioxide and/or Tale and/or Dibasic Calcium Phosphate and/or Sodium Carboxy Methyl Cellulose and/or Simethicone and/or Colloidal Silicon dioxide.

The medicament and some of the solid components of the above excipients were milled and sifted preferably through 60 to 100 mesh sieve. The addition of all the solid and liquid excipients and its final mixing with the medicament was carried in a suitable mixer equipped with planetary movement of its agitators along with high speed homogenizer to ensure proper particle size to achieve micro suspension.

Dissolution Testing:

Drug dissolution testing is routinely used to provide critical in vitro drug release information for both quality control purposes to predict in vivo drug release profiles.

The media for dissolution test was 0.1 N. HCl with 3% Benzalkonium Chloride.

At 60 minute time frame, the % Cumulative Drug Release for Artemether, Lumefantrine and Remdesivir was 92.3%, 90.3% and 91.7% respectively

| % of Drug Release in a Dissolution Test | | | |
|---|---|---|---|
| Sample Time (minute) | % Artemether | % Lumefantrine | % Remdesivir |
| 30 | 47.3 | 81.6 | 52.6 |
| 60 | 72.25 | 93.7 | 73.4 |
| 90 | 88.7 | 100 | 85.8 |
| 120 | 93.8 | 100 | 92.6 |

It is noted that the Peak Inhibitory Concentration (Threshold) of Artemether and Remdesivir were at 120 minutes after oral administration. The Peak Inhibitory Concentration (Threshold) of Lumefantrine was at 60 minutes after oral administration.

12. Nanoparticles Based Combination Drug Therapy in Intranasal Delivery System

According to the World Health Organization, approximately 14% of patients with severe COVID-19 that require hospitalization and supplemental oxygen, and 5% will require treatment in intensive care units. More than 80% of the patients in early onset of Covid-19 can be treated at home or in alternative care settings (Clinical management of severe acute respiratory infection (SARI) when COVID-19 disease is suspected-Interim guidance 13 Mar. 2020-World Health Organization-https://www.who.int/docs/default-source/coronaviruse/clinical-management-of-novel-cov.pdf?sfvrsn=bc7da517_10&download=true).

There is a window of opportunity to mitigate or to stop the spread of Covid-19 virus infection which was found to be within the first 7 days from the date the patient was tested positive of the disease. Most patients prefer to be in quarantined at home and are not hospitalized until the symptoms become critical. Treating severe cases of Covid-19 with severe acute respiratory syndrome and other morbidities is extremely difficult and the mortality rates for severe cases of Covid-19 is high. There is an urgent need to develop drug therapeutic prevent and treatment of early onset of Covid-19 in a form of oral or intranasal formulation in home care setting that enables people with high risks to administer themselves.

The invention will describe a combination drug therapy in a form of nanoparticles in an intranasal delivery system that can be used by the patient at home for prevention and treatment of early onset of Covid-19. The advantages of intranasal drug delivery versus administration via intramuscular, subcutaneous or intravenous are obvious. Intranasal drug delivery is much easier than injection and is a non-invasive method. Additional potential advantages for intranasal administration over drug administration by injection are: better patient compliance; convenient route for drug self-administration by the patient, and thus decreasing the need for drug administration by medically trained personnel; elimination of injection-site injuries and the problem of sharps disposal factor associated with syringe needle injections and low cost to the patient and the healthcare system The present invention describes a new method to make nanoparticle formulation of an antimalarial drug such as Artemether; antiviral drug such as Remdesivir (GS-5734), Atazanavir, Digoxin; an Angiotensin I I receptor blocker such as Valsartan; an immunomodulating drug such as Teriflunomide; a neuroprotective agent such as Cyclic Prolyl Glycine (cPG); or a combination drug therapy comprising of any the above mentioned drugs.

The methods for preparing chitosan particles have been published in the literatures. Some relevant publications include: "Physicochemical properties and blood compatibility of acylated chitosan nanoparticles" (Dong-Won Lee et al., Carbohydrate Polymers, 58 (2004) 371-377) and "Reacetylated chitosan microspheres for controlled delivery of anti-microbial agents to the gastric mucosa" (A. Portero et al., MICROCAPSULATION, 19 (2002)).

The U.S. Pat. No. 8,211,475B2 patent provides a process for preparing chitosan nanoparticles in water phase, which comprises of adding water first and then followed by acetic anhydride to the chitosan solution to carryout acetylation, wherein the concentration of acetic anhydride is about 10 v/v % to about 30 v/v % of the total volume of the whole solution. In the propose process the chemical modification of the chitosan solution is chemically modified in water phase so as to convert the molecular chain of chitosan and make it amphipathic. During the formation of a gel from the modification of chitosan through acetylation, using variable concentrations of chitosan and acetic anhydride and utilizing physical dispersion, the above method yields chitosan particles of nano scale and avoids the formation of large gel mass.

The methods taught in the literatures involved complicated chemical modification and are time- and labor-consuming. In addition, the organic solvents utilized during the manufacture tend to remain in the resulting chitosan particles. Under such circumstances, even if chitosan nanoparticles are produced, it was not clear whether they are safe for use in medical applications, particularly, the nanoparticles delivery of antiviral drugs. There is still a need for a method for preparing chitosan nanoparticles which have good biocompatibility and are safe for medical applications.

One objective of the present invention is to provide a novel nanoparticle system and methods of preparation nanoparticle formulation of an antimalarial drug such as Artemether; and antiviral drug such as Remdesivir, Atazanavir, Digoxin; an Angiotensin II receptor blocker such as Valsartan; an immunomodulating drug such as Teriflunomide; a neuroprotective drug such as Donepezil, Rivastigmine, Memantine, Galantamine, and Cyclic Prolyl Glycine (cPG); an anti-inflammatory drug as Dexamethasone, Methylprednisolone, or a combination drug therapy comprising of any the above mentioned drugs.

In nanoparticle based combined drug molecules, an Angiotensin II receptor blocker will serve as a carrier to bind to and inhibit the angiotensin II type 1 receptor (AT1) and thereby block the arteriolar contraction and sodium retention effects of renin-angiotensin system. To be able to complete and prevent Covid virus from infecting the cell, the particle size of a combined drug molecule is comparable with the size of the Covid-19 virus, which is within the range of 120-150 nm.

The present invention describes the application of chitosan and chitosan derivatives as nasal absorption enhancers, for making nanoparticle formulation of the drugs of interest as mentioned above.

Chitosan is a polysaccharide derived from alkaline deacetylation of chitin mostly originating from crustacean shells. Chitosan is positively charged at acidic pH, and its apparent pKa (6.1-7.3) is directly related to the degree of deacetylation. Chitosan is insoluble at neutral and basic pH values, but forms salts with inorganic or organic acids, such as HCl and glutamic acid, that are soluble in water, up to about pH 6.3. Chitosan is biocompatible, is recognized as a generally safe (GRAS) material and has been approved in the tissue engineering field for both wound dressing applications (e.g. Hemcon® marketed products, FDA approved).

The local non-irritating characteristics of chitosan and the low local and systemic toxicity have been extensively demonstrated in the literature and confirmed by a filed DMFs (type IV) at FDA and EMA.

Chitosan is a drug carrier currently regarded as having extremely high safety (LD50>4 g/kg). Chitosan is able to interact through its positively charged amino groups with the anionic counterpart present in the mucous layers, mainly sialic acid, and to affect the permeability of the epithelial membrane by the transient opening of the tight junctions in the epithelial cells. This results in chitosan being able to retain a formulation for extended time periods in the nasal cavity and at the same time enable the transport of hydrophilic molecules across the membrane.

It is known that Chitosan (CS) has a strong affinity of adhering to the mucosal surface and transiently opening the tight junctions between epithelial cells (Pharm. Res. 1994; 11:1358-1361). Most commercially available CSs have a quite large molecular weight (MW) and need to be dissolved in an acetic acid solution at a pH value of approximately 4.0 or lower. The CS with low MW can be used together with a good solubility at a pH value close to physiological ranges (Eur. J. Pharm. Biopharm. 2004; 57:101-105). On this basis, a low-MW CS. obtained by depolymerizing a commercially available CS using cellulase, is preferable to prepare nanoparticles of the present invention.

The γ-PGA, an anionic peptide, is a natural compound produced as capsular substance or as slime by members of the genus *Bacillus* (Crit. Rev. Biotechnol. 2001; 21.219-232) γ-PGA is unique in that it is composed of naturally occurring L-glutamic acid linked together through amide bonds. It was reported from literature that this naturally occurring γ-PGA is a water-soluble, biodegradable, and non-toxic polymer. A related, but structurally different polymer. [poly(α-glutamic acid), α-PGA] has been used for drug delivery (Adv Drug Deliver. Rev. 2002; $4:695-713; Cancer Res. 1998; 58:2404-2409). α-PGA is usually synthesized from poly(α-benzyl-L-glutamate) by removing the benzyl protecting group with the use of hydrogen bromide.

In one embodiment, the molecular weight of a low-MW CS of the present invention is about 50 kDa and less than 80 kDA to be adequately soluble at a near neutral pH that maintains the bioactivity of protein and peptide drugs. The particle size and the zeta potential value of the prepared nanoparticles are controlled by their constituted compositions.

In a further embodiment, the nanoparticles have a mean particle size between about 50 and 200 nanometers, preferably between about 100 and 150 nanometers, and most preferably between about 120 and 200 nanometers. The bioactive nanoparticle fragments resulting from the nanoparticles of the present invention are generally in the range of about 50 to 150 nm, preferably in the range of about 75 to 100 nm.

In some embodiments, the nanoparticles are loaded with a therapeutically effective amount of at least one bioactive agent, wherein the bioactive agent is selected from the group consisting of antiviral agents, anti-hypertensive drugs and anti-inflammatory drugs. The bioactive agent is lipophilic, hydrophobic, or hydrophilic.

Figure 1:
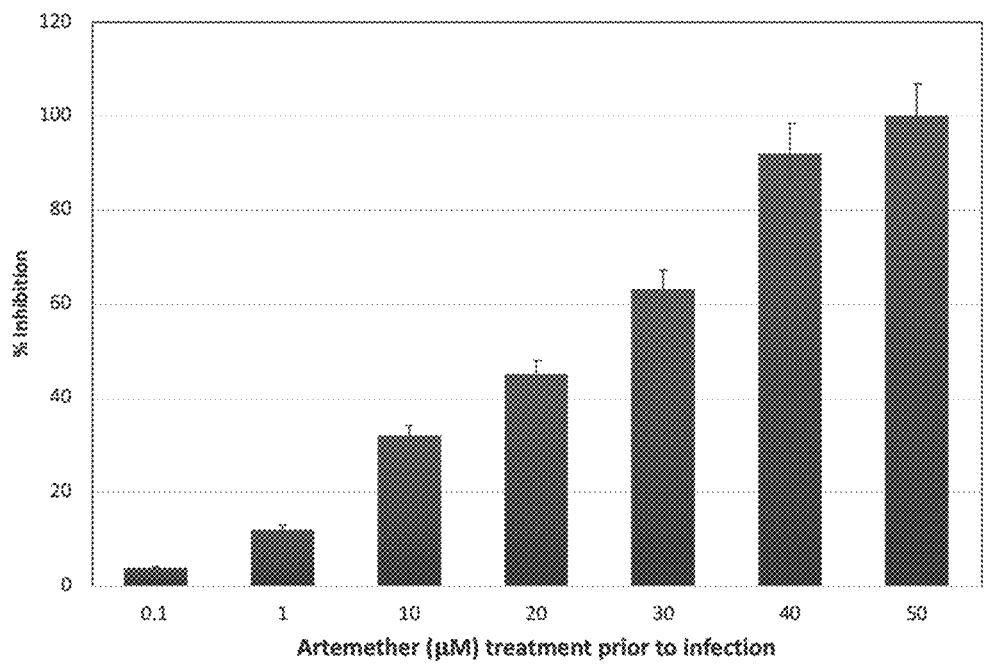
FIG. 1 generally depicts Percentage Inhibition of Artemether Treatment Prior to Infection.
Figure 2:
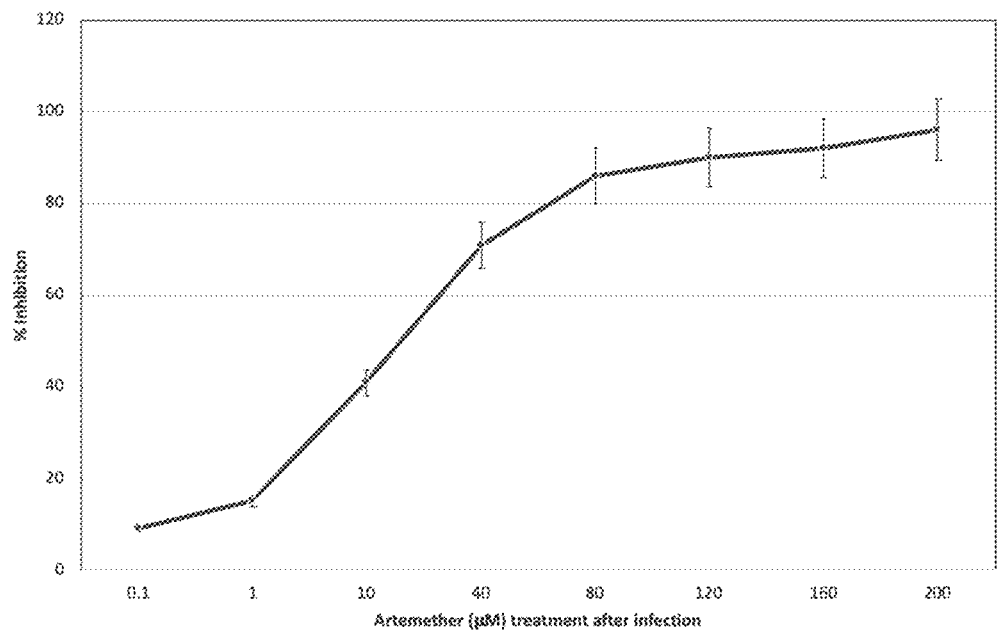
FIG. 2 generally depicts Percentage of Inhibition of Artemether Treatment After Infection.
Figure 3:
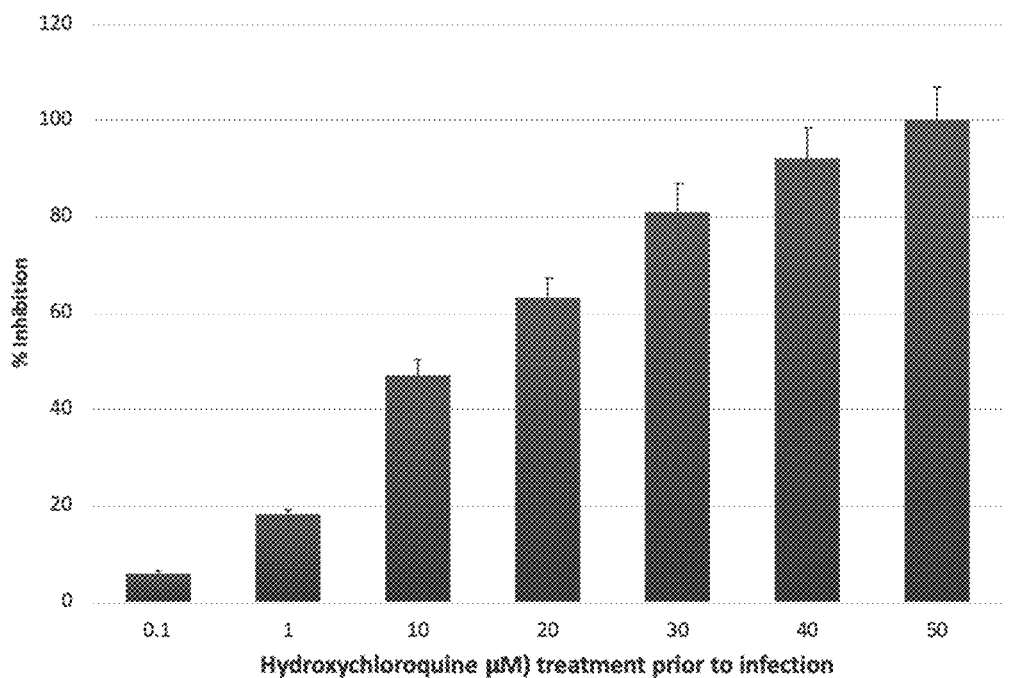
FIG. 3 generally depicts Percentage Inhibition of Hydroxychloroquine Treatment Prior to Infection.
Figure 4:
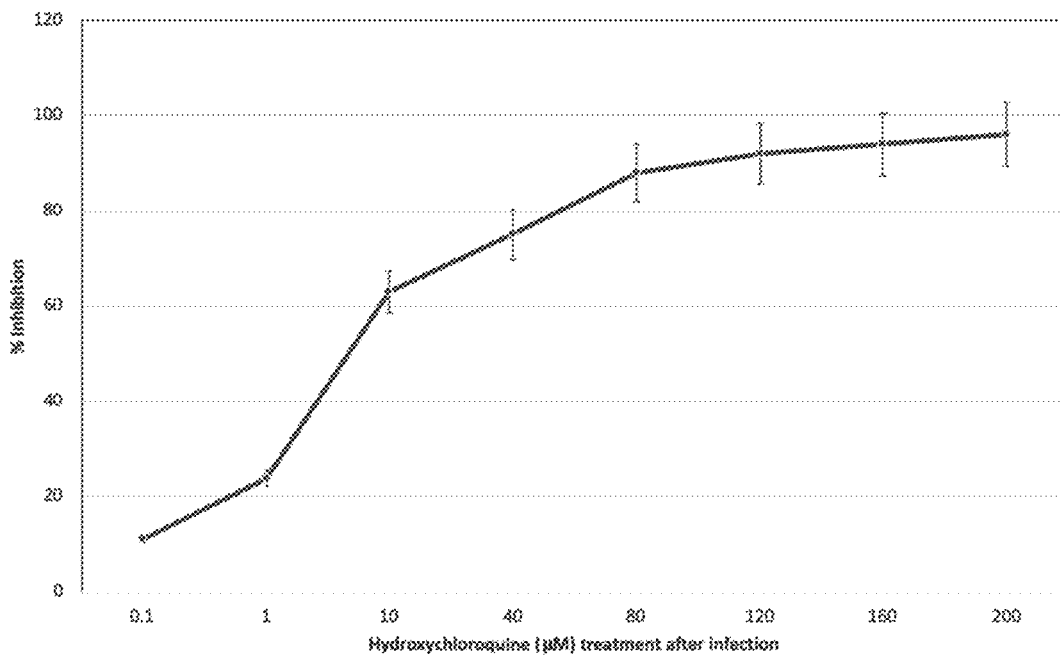
FIG. 4 generally depicts Percentage Inhibition of Hydroxychloroquine Treatment After Infection.

E6 cells with artemether rendered these cells refractory to SARS-CoV2 infection. (FIG. 1).

EXAMPLES

In Vitro Experimental Methods

In carrying out the in vitro experiments, vero E6 cells (an African green monkey kidney cell line) were infected with SARS-CoV2 at a multiplicity of infection of 0.5 for 1 hour. The cells were washed with PBS and then incubated in OPTI-MEM (Invitrogen) medium with or without various concentrations of the following drug candidates: Artemether (from BiopharmaRx) Hydroxychloroquine (from Sigma Aldrich), Atazanavir (from Sigma Aldrich), and Efavirenz (from Sigma Aldrich), Fosamprenavir Calcium (from Sigma Aldrich), Saquinavir (from Sigma Aldrich) and Remdesivir (from AOBIOUS, INC., USA)

Immunofluorescence staining was performed with SARS-CoV2-specific hyperimmune mouse ascitic fluid (HMAF) followed by anti-mouse fluorescein-coupled antibody.

Twenty four hours after infection, the virus-containing supernatants were removed, and the cells were pulsed with 35S-(Cys) for 45 min and chased for 4 hours before lysis in RIPA buffer. Clarified cell lysates and media were incubated with HMAF, and immunoprecipitated proteins were separated by 7-10% NuPAGE gel (Invitrogen); proteins were visualized by autoradiography. In some experiments, cells were washed for 4 hours with isotope-free medium. Clarified cell supernatants were also immunoprecipitated with SARS-CoV2-specific HMAF.

Experiment 1: Results for Artemether Treatment Prior to Infection

Figure 6:
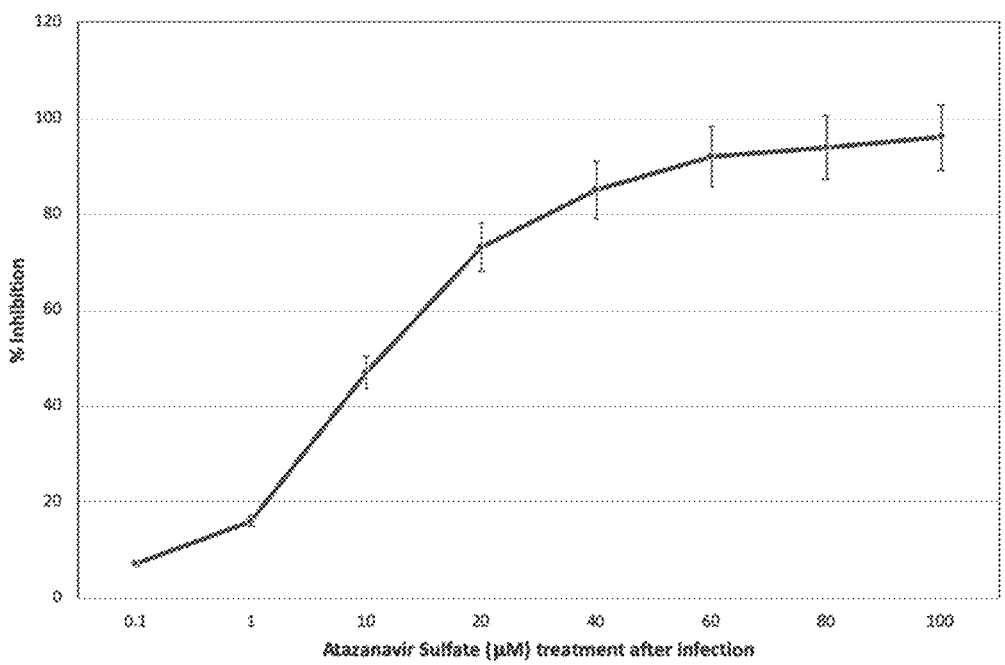
FIG. 6 generally depicts Percentage Inhibition of Atazanavir Sulfate Treatment After Infection.
Figure 7:
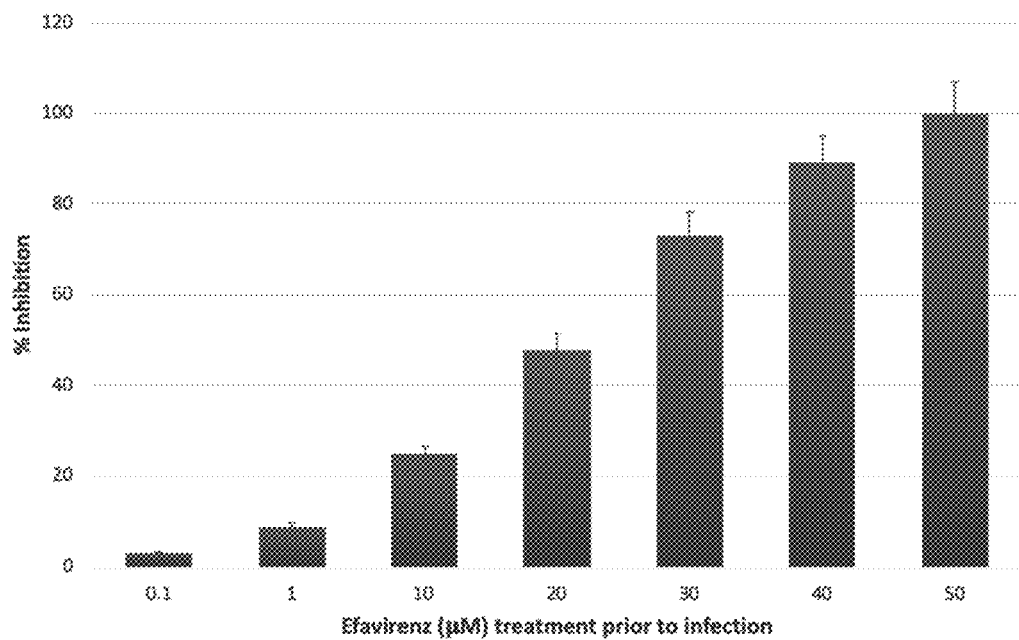
FIG. 7 generally depicts Percentage Inhibition of Efavirenz treatment prior to infection.
Figure 8:
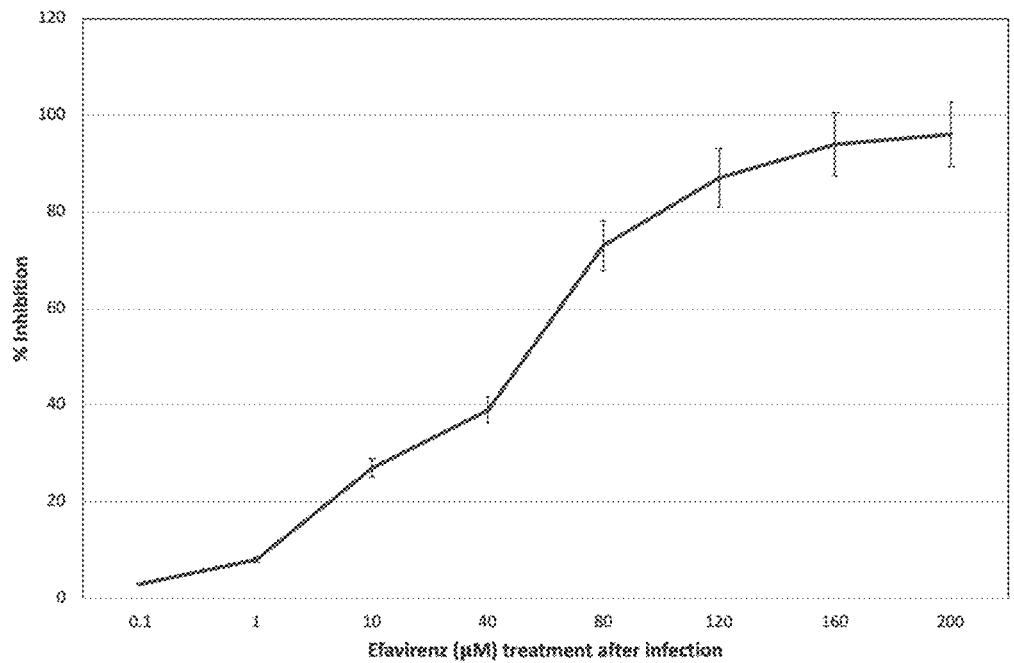
FIG. 8 generally depicts Percentage Inhibition of Efavirenz treatment after infection.
Figure 9:
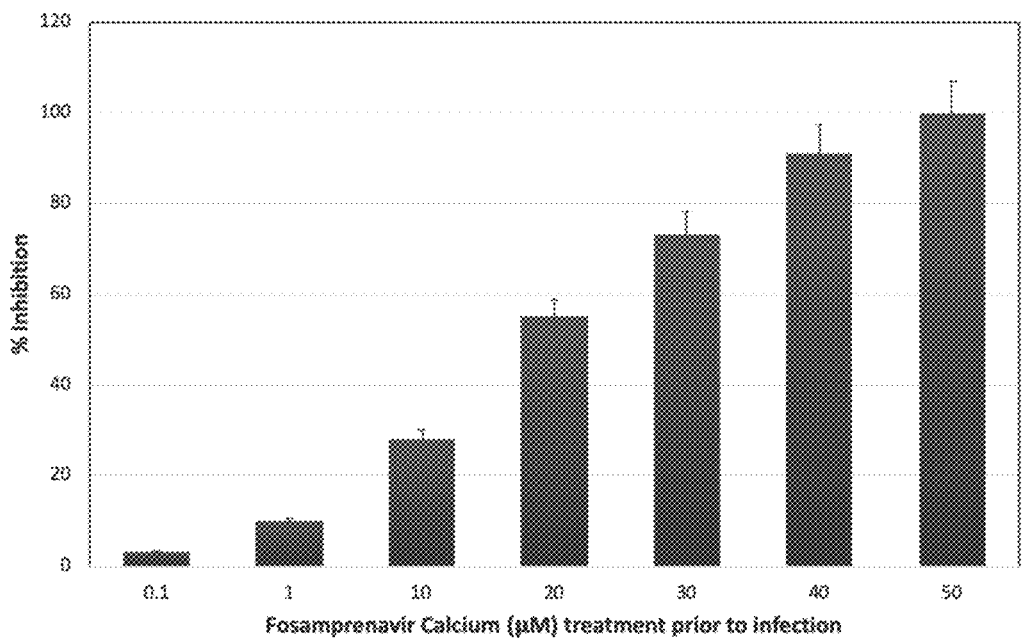
FIG. 9 generally depicts Percentage Inhibition of Fosamprenavir Calcium treatment prior to infection.
Figure 10:
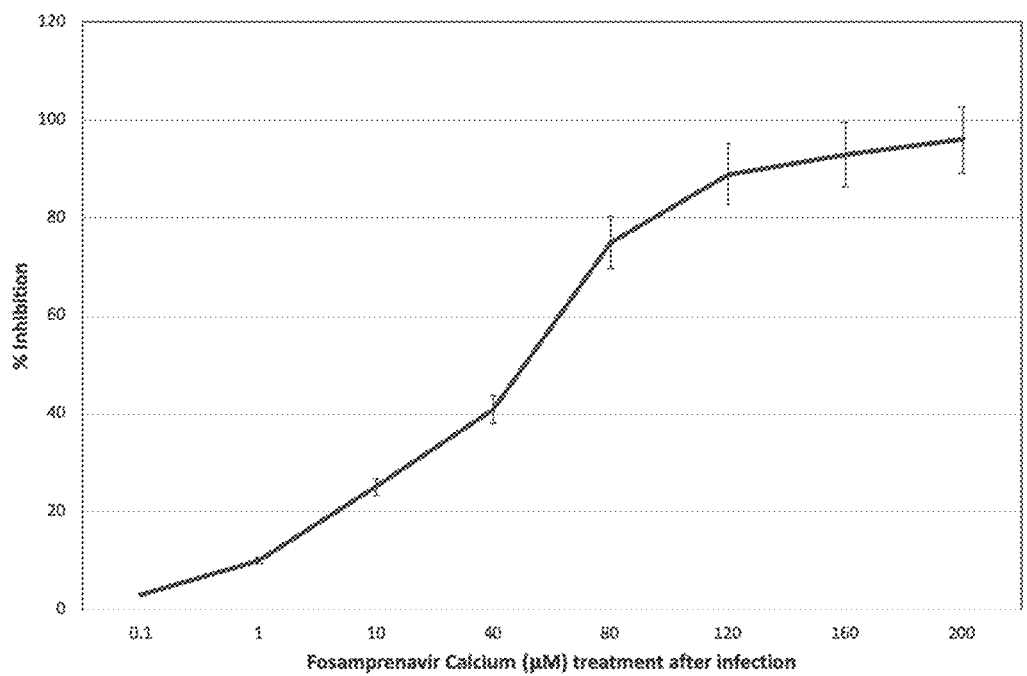
FIG. 10 generally depicts Percentage Inhibition of Fosamprenavir Calcium treatment after infection.
Figure 11:
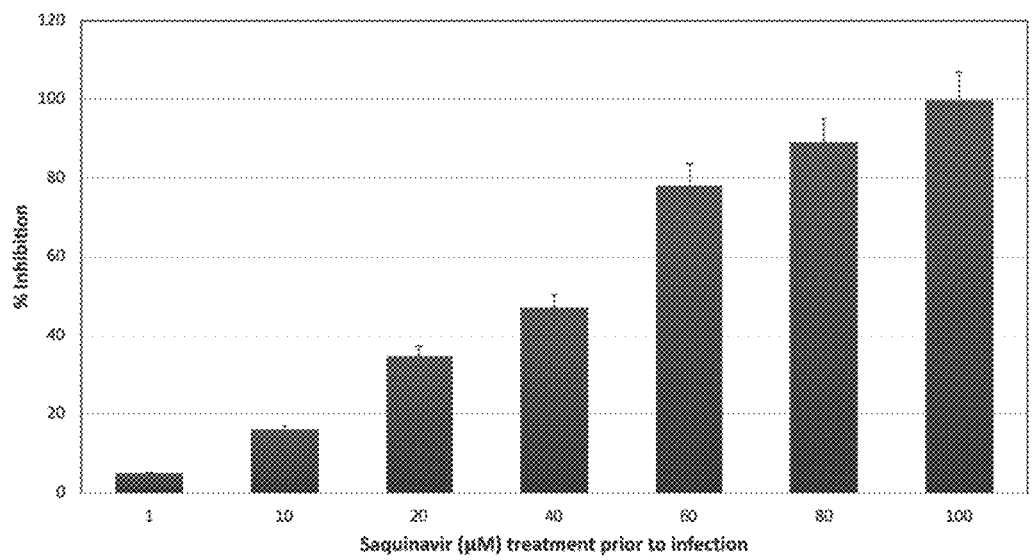
FIG. 11 generally depicts Percentage Inhibition of Saquinavir treatment prior to infection.
Figure 12:
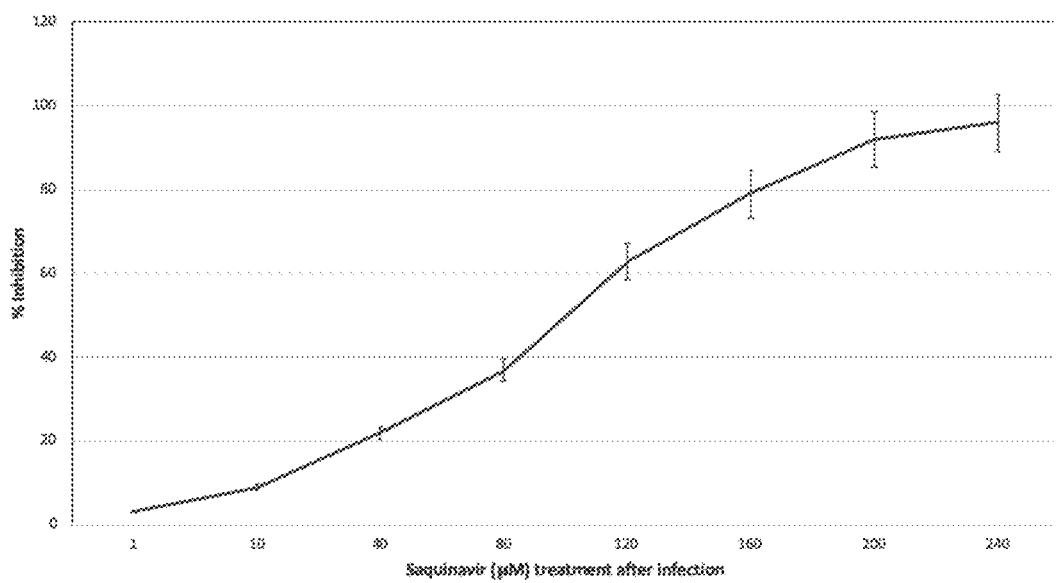
FIG. 12 generally depicts Percentage Inhibition of Saquinavir treatment after infection.
Figure 13:
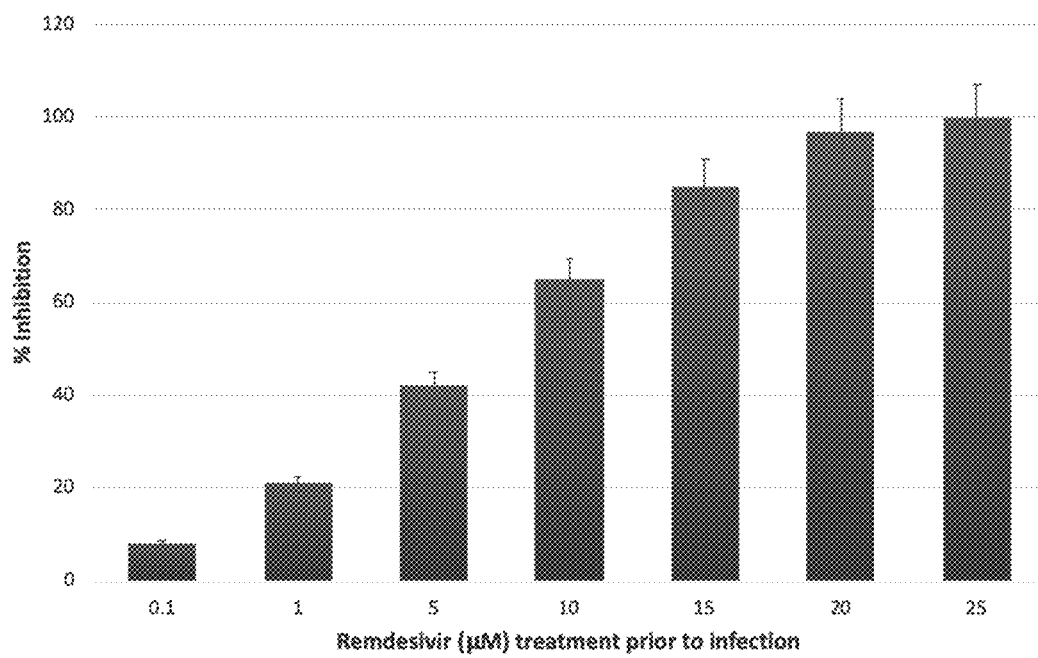
FIG. 13 generally depicts Percentage Inhibition of Remdesivir treatment prior to infection.
Figure 14:
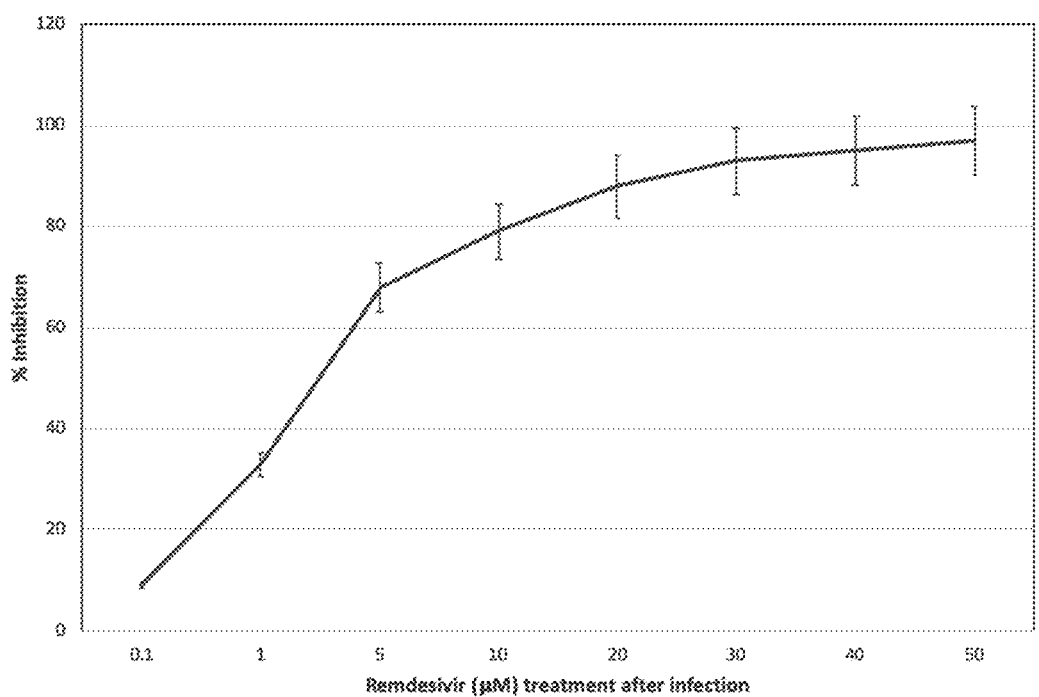
Figure 15:
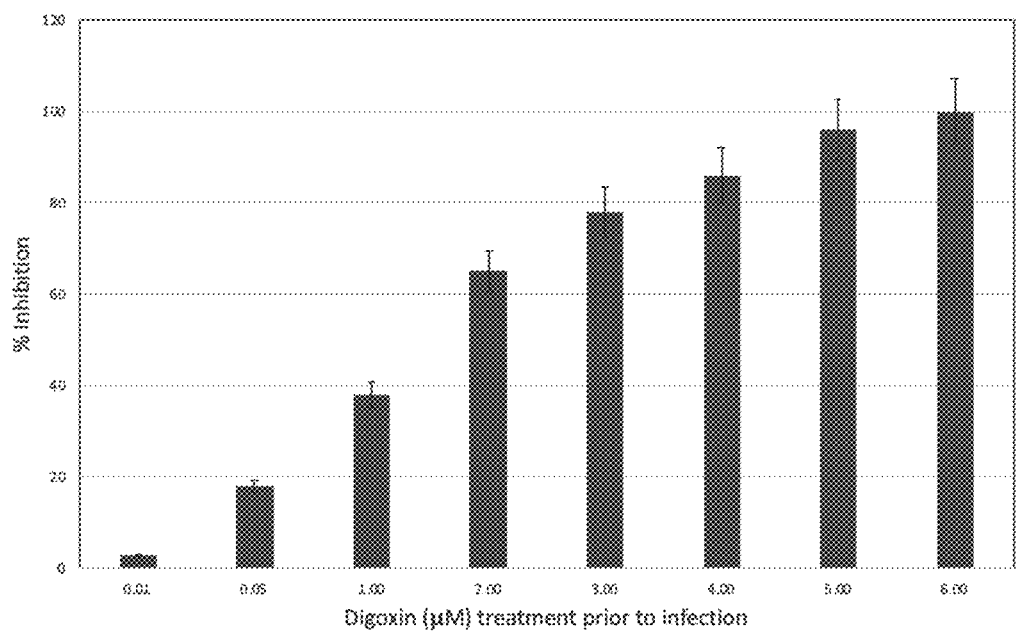
FIG. 15 generally depicts Percentage Inhibition of Digoxin treatment prior to infection.
Figure 16:
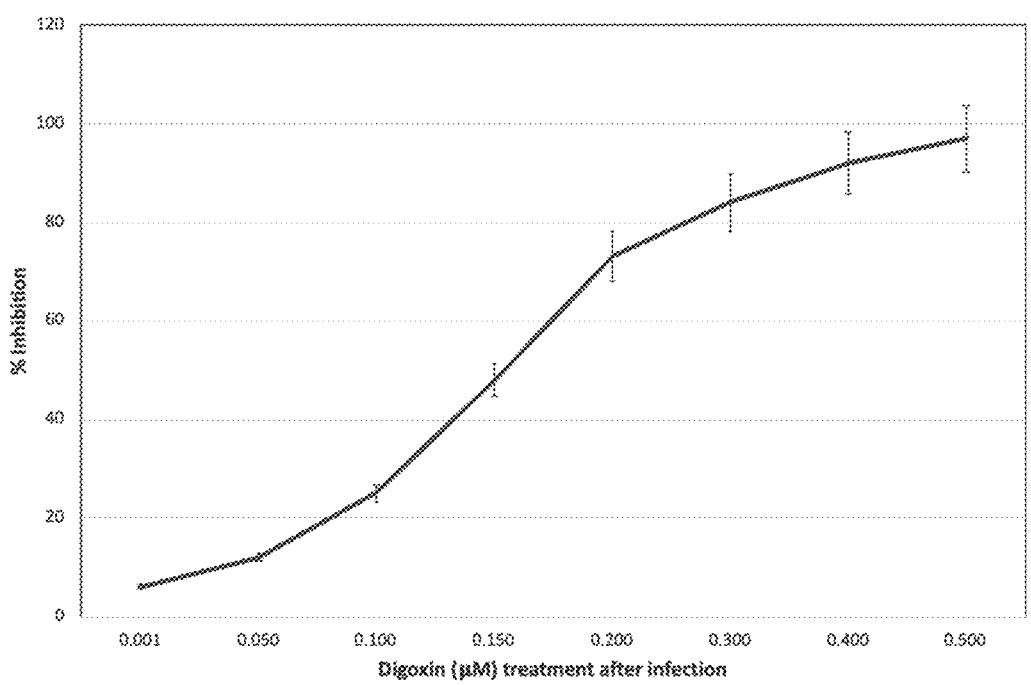
FIG. 16 generally depicts Percentage Inhibition of Digoxin treatment after infection.
Figure 17:
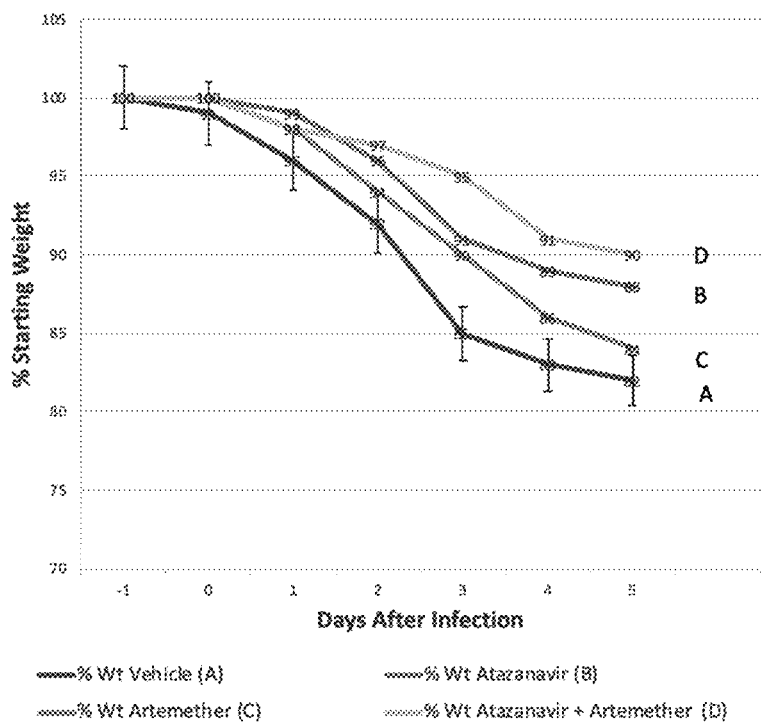
FIG. 17 generally depicts Weight Lost Studies of Artemether and Atazanavir-Oral. Percent starting weight of Ces1c−/− mice infected with 104 PFU SARS-CoV MA15 treated beginning at −1 dpi with either vehicle (n=8) or Artemether (2 mg/kg) in oral powder/suspension, Atazanavir (4 mg/kg) in oral powder/suspension, or Artemether (2 mg/kg) plus Atazanavir (4 mg/kg) in oral power/suspension (n=24).
Figure 18:
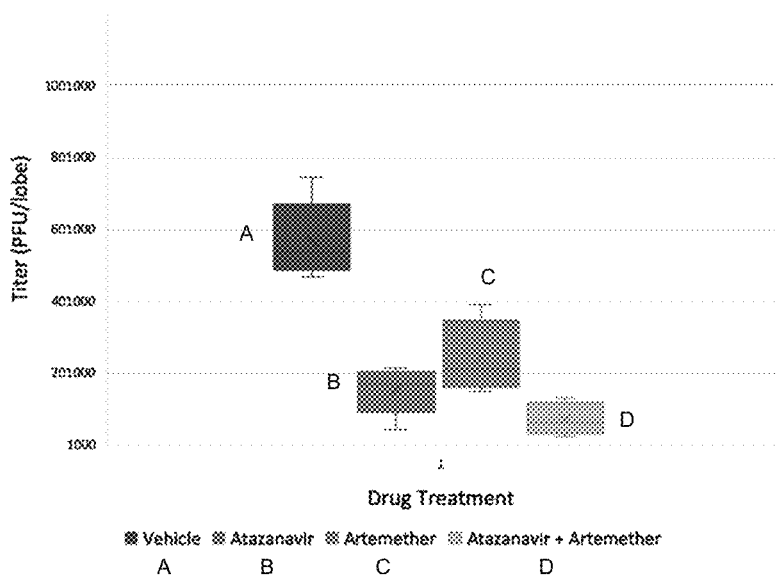
FIG. 18 generally depicts Lung Titers studies of Artemether and Atazanavir (Oral). SARS-CoV lung titers in mice infected and treated beginning at −1 dpi with either vehicle (n=8) or Artemether (4 mg/kg), Atazanavir (4 mg/kg) oral, or Artemether (4 mg/kg) plus Atazanavir (4 mg/kg) in Chitosan nanoparticles (n=24).
Figure 19:
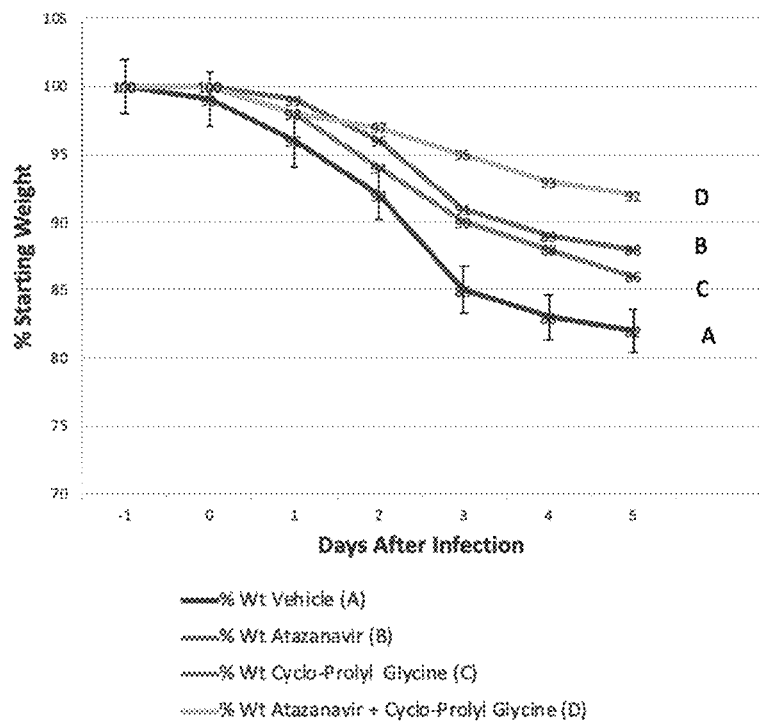
FIG. 19 generally depicts Weight Loss Studies of Cyclic Prolyl Glycine and Atazanavir-Oral. Percent starting weight of Ces1c−/− mice infected with 104 PFU SARS-CoV MA15 treated beginning at −1 dpi with either vehicle (n=8) or Cyclic Prolyl Glycine (0.2 mg/kg) in oral powder/suspension, Atazanavir (4 mg/kg) in oral powder/suspension, or Cyclic Prolyl Glycine (0.2 mg/kg) plus Atazanavir (4 mg/kg) in oral power/suspension (n=24).
Figure 20:
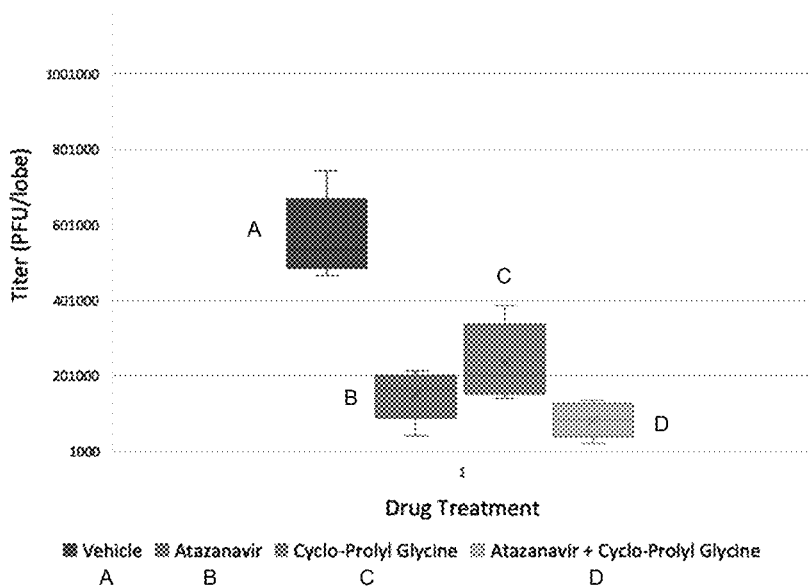
FIG. 20 generally depicts Lung Titers studies of Cyclic Prolyl Glycine and Atazanavir (Oral). SARS-CoV lung titers in mice infected and treated beginning at −1 dpi with either vehicle (n=8) or Cyclic Prolyl Glycine (0.2 mg/kg) in oral powder/suspension, Atazanavir (4 mg/kg) in oral powder/suspension, or Cyclic Prolyl Glycine (0.2 mg/kg) plus Atazanavir (4 mg/kg) in oral power/suspension (n=24).
Figure 21:
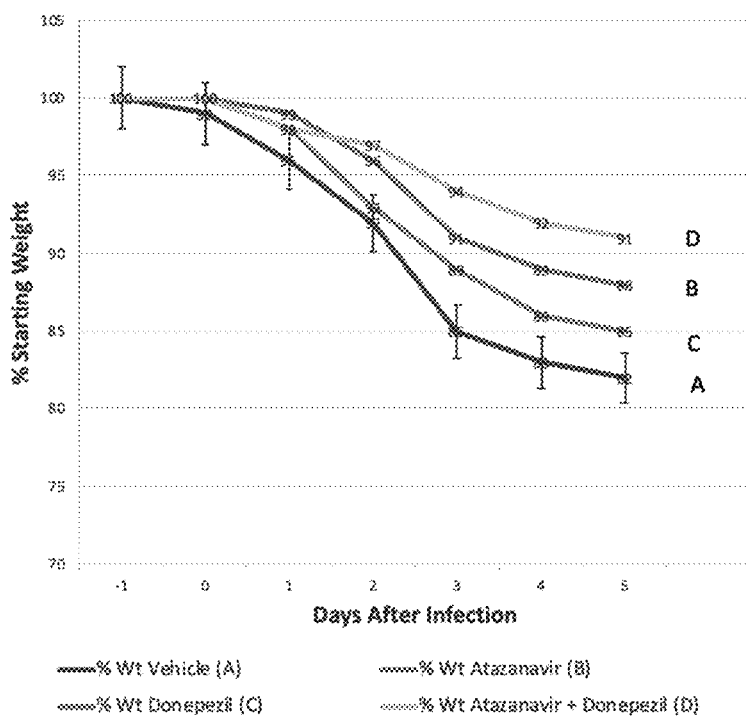
FIG. 21 generally depicts Weight Loss Studies of Donepezil and Atazanavir-Oral. Percent starting weight of Ces1c−/− mice infected with 104 PFU SARS-CoV MA15 treated beginning at −1 dpi with either vehicle (n=8) or Donepezil (0.15 mg/kg) in oral powder/suspension, Atazanavir (4 mg/kg) in oral powder/suspension, or Donepezil (0.15 mg/kg) plus Atazanavir (4 mg/kg) in oral power/suspension (n=24).
Figure 22:
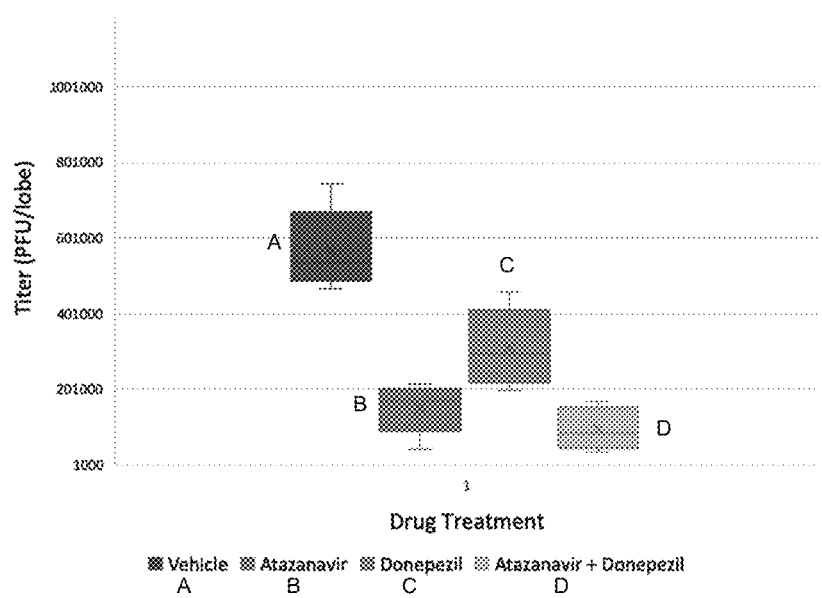
FIG. 22 generally depicts Lung Titers studies of Donepezil and Atazanavir and (Oral). SARS-CoV lung titers in mice infected and treated beginning at −1 dpi with either vehicle (n=8) or Donepezil (0.15 mg/kg) in oral powder/suspension, Atazanavir (4 mg/kg) in oral powder/suspension, or Donepezil (0.15 mg/kg) plus Atazanavir (4 mg/kg) in oral power/suspension (n=24).
Figure 23:
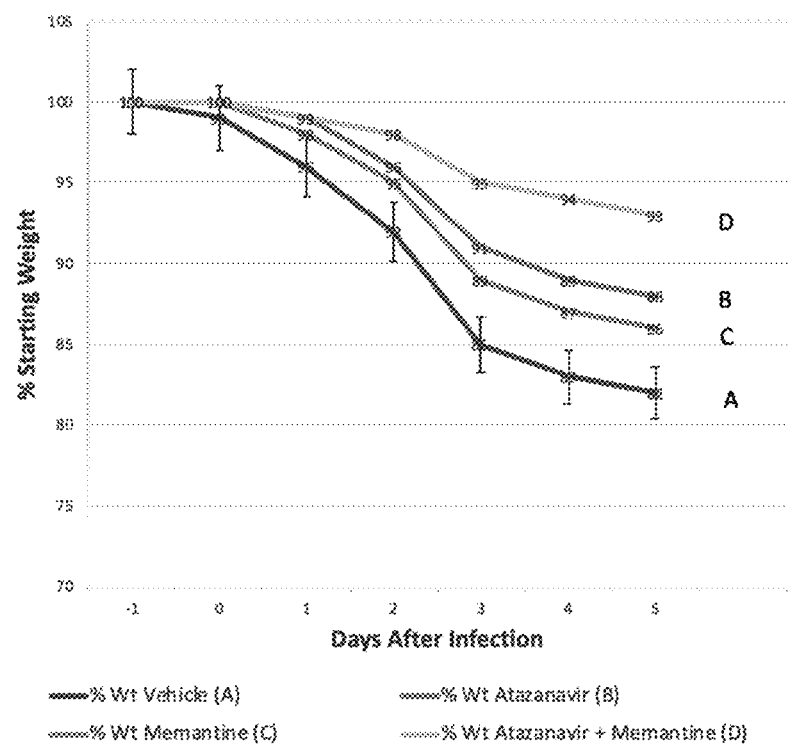
FIG. 23 generally depicts Weight Loss Studies of Memantine and Atazanavir-Oral. Percent starting weight of Ces1c−/− mice infected with 104 PFU SARS-CoV MA15 treated beginning at −1 dpi with either vehicle (n=8) or Memantine (0.15 mg/kg) in oral powder/suspension, Atazanavir (4 mg/kg) in oral powder/suspension, or Memantine (0.15 mg/kg) plus Atazanavir (4 mg/kg) in oral power/suspension (n=24).
Figure 24:
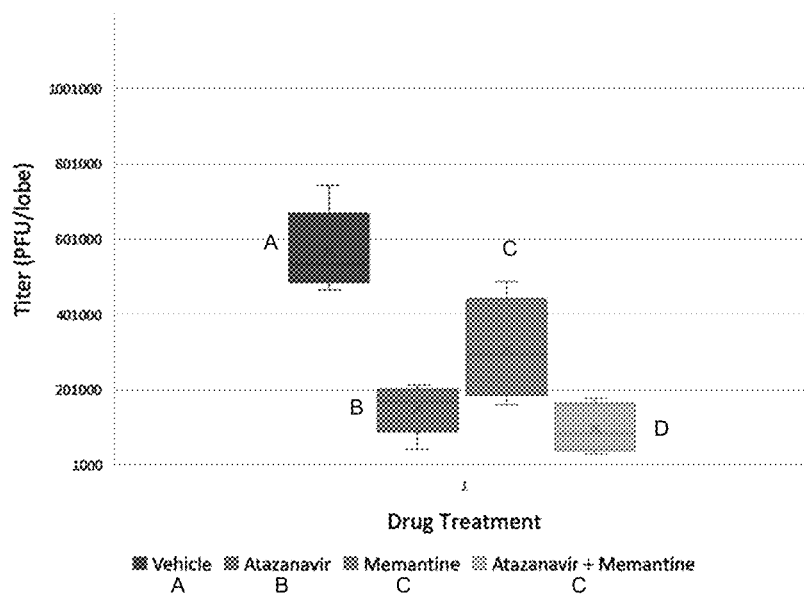
FIG. 24 generally depicts Lung Titers studies of Memantine and Atazanavir and (Oral). SARS-CoV lung titers in mice infected and treated beginning at −1 dpi with either vehicle (n=8) or Memantine (0.15 mg/kg) in oral powder/suspension, Atazanavir (4 mg/kg) in oral powder/suspension, or Memantine (0.15 mg/kg) plus Atazanavir (4 mg/kg) in oral power/suspension (n=24).
Figure 25:
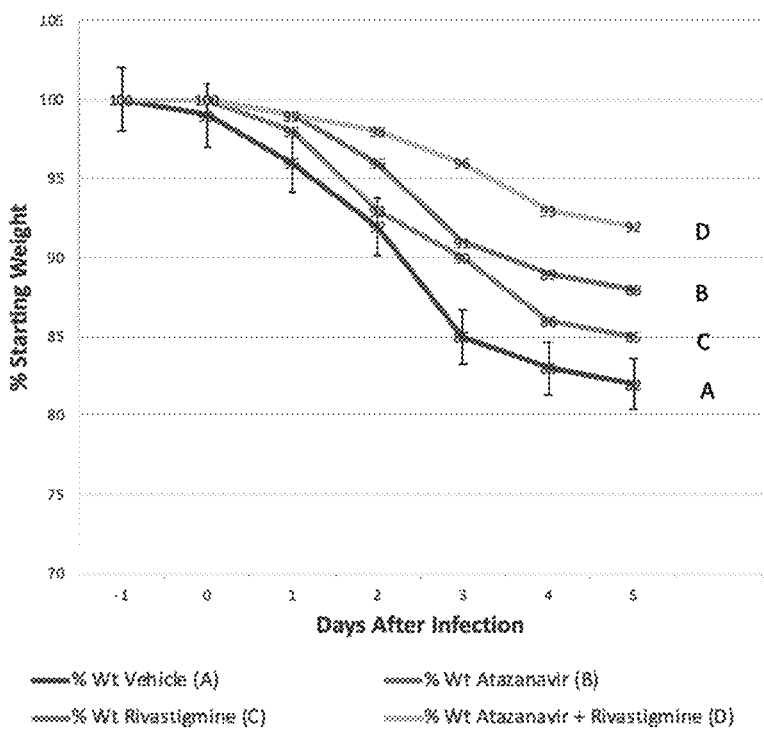
FIG. 25 generally depicts Weight Loss Studies of Rivastigmine and Atazanavir-(Oral). Percent starting weight of Ces1c−/− mice infected with 104 PFU SARS-CoV MA15 treated beginning at −1 dpi with either vehicle (n=8) or Rivastigmine (0.01 mg/kg) in oral powder/suspension, Atazanavir (4 mg/kg) in oral powder/suspension, or Rivastigmine (0.01 mg/kg) plus Atazanavir (4 mg/kg) in oral power/suspension (n=24).
Figure 26:
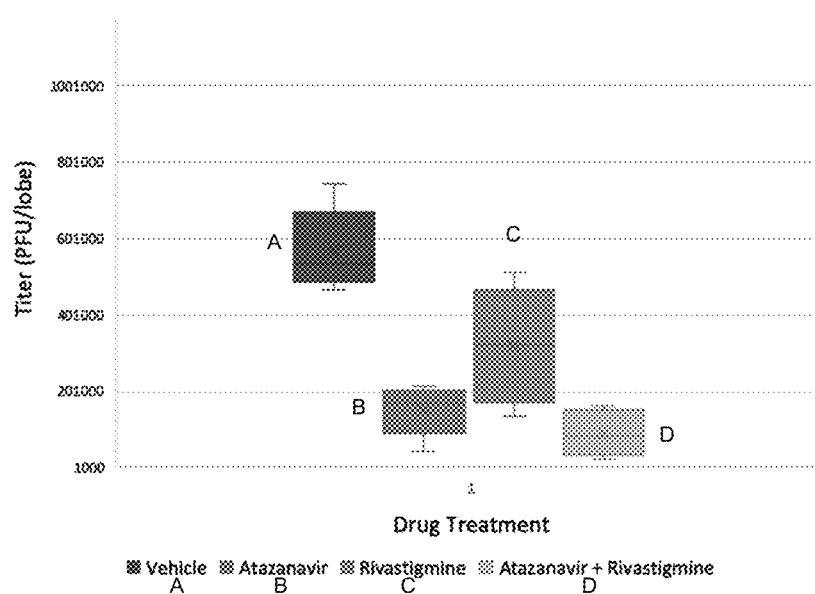
FIG. 26 generally depicts Lung Titers studies of Rivastigmine and Atazanavir and (Oral). SARS-CoV lung titers in mice infected and treated beginning at −1 dpi with either vehicle (n=8) or Rivastigmine (0.01 mg/kg) in oral powder/suspension, Atazanavir (4 mg/kg) in oral powder/suspension, or Rivastigmine (0.01 mg/kg) plus Atazanavir (4 mg/kg) in oral power/suspension (n=24).
Figure 27:
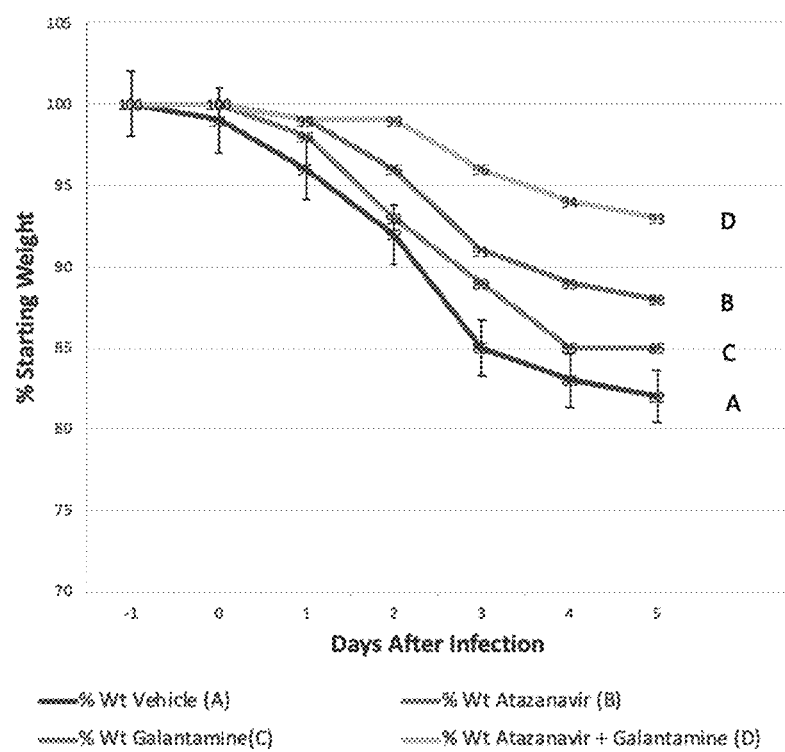
FIG. 27 generally depicts Weight Loss Studies of Galantamine and Atazanavir-(Oral). Percent starting weight of Ces1c−/− mice infected with 104 PFU SARS-CoV MA15 treated beginning at −1 dpi with either vehicle (n=8) or Galantamine (0.20 mg/kg) in oral powder/suspension, Atazanavir (4 mg/kg) in oral powder/suspension, or Galantamine (0.20 mg/kg) plus Atazanavir (4 mg/kg) in oral power/suspension (n=24).
Figure 28:
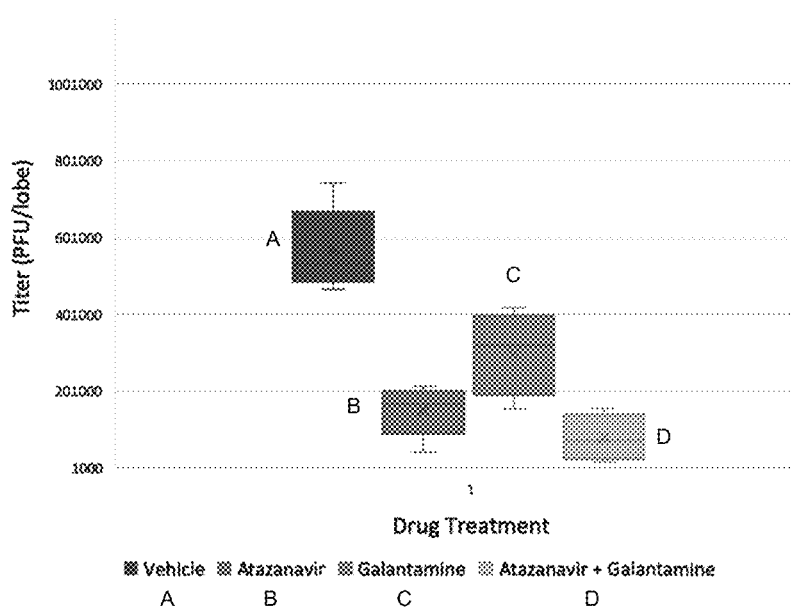
FIG. 28 generally depicts Lung Titers studies of Galantamine and Atazanavir and (Oral). SARS-CoV lung titers in mice infected and treated beginning at −1 dpi with either vehicle (n=8) or Galantamine (0.20 mg/kg) in oral powder/suspension, Atazanavir (4 mg/kg) in oral powder/suspension, or Galantamine (0.20 mg/kg) plus Atazanavir (4 mg/kg) in oral power/suspension (n=24).

Experiments were carried out to determine the impact of artemether treatment on SARS-CoV2 infection. Permissive Vero E6 cells were pre-treated with various concentrations of artemether (0.1-50 µM) for 18-24 hours prior to virus infection. Cells were then infected with SARS-CoV2, and virus antigens were visualized by indirect immunofluorescence. For quantitative purposes, we counted the number of cells stained positive from three random locations on a slide. The average number of positively stained control cells was scored as 100% and was compared with the number of positive cells observed under various artemether concentrations. Pretreatment with 0.1, 1, 10, 20, 30, 40 and 50 μM artemether reduced infectivity by 4%, 12%, 32%, 45%, 63%, 92% and 100% respectively. Reproducible results were obtained from three independent experiments. These data demonstrated that pretreatment of Vero.

Experiment 2: Results for Artemether Treatment After Infection

The antiviral properties of artemether on SARS-CoV2 after the initiation of infection were studied. Vero E6 cells were infected with the virus and fresh medium supplemented with various concentrations of artemether was added immediately after virus adsorption. Infected cells were incubated for an additional 24 hours, after which the presence of virus antigens was analyzed by indirect immunofluorescence analysis. When artemether was added after the initiation of infection, there was a dramatic dose dependent decrease in the number of virus antigen-positive cells. Approximately 10 μM artemether reduced the infection by 40% and up to 71-96% inhibition was observed with 40-100 μM concentrations. A half-maximal inhibitory effect was estimated to occur at 16.5±1.0 μM artemether. These data clearly show that addition of artemether can effectively reduce the establishment of infection and spread of SARS-CoV2 if the drug is added immediately following virus adsorption. (FIG. 2).

Experiment 3: Results for Hydroxychloroquine Treatment Prior to Infection

Experiments were carried out to determine the impact of hydroxychloroquine sulfate treatment on SARS-CoV2 infection. Permissive Vero E6 cells were pre-treated with various concentrations of hydroxychloroquine sulfate (0.1-50 μM) for 18-24 hours prior to virus infection. Cells were then infected with SARS-CoV2, and virus antigens were visualized by indirect immunofluorescence. For quantitative purposes, we counted the number of cells stained positive from three random locations on a slide. The average number of positively stained control cells was scored as 100% and was compared with the number of positive cells observed under various hydroxychloroquine sulfate concentrations. Pretreatment with 0.1, 1, 10, 20, 30, 40 and 50 μM hydroxychloroquine sulfate reduced infectivity by 6%, 18%, 47%63%, 81%, 92% and 100% respectively. Reproducible results were obtained from three independent experiments. These data demonstrated that pretreatment of Vero E6 cells with hydroxychloroquine sulfate rendered these cells refractory to SARS-CoV2 (Covid-19) infection. (FIG. 3).

Experiment 4: Results for Hydroxychloroquine Treatment After Infection

The antiviral properties of hydroxychloroquine sulfate on SARS-CoV2 after the initiation of infection were studied. Vero E6 cells were infected with the virus and fresh medium supplemented with various concentrations of hydroxychloroquine sulfate was added immediately after virus adsorption. Infected cells were incubated for an additional 24 hours, after which the presence of virus antigens was analyzed by indirect immunofluorescence analysis. When hydroxychloroquine sulfate was added after the initiation of infection, there was a dramatic dose dependent decrease in the number of virus antigen-positive cells. Approximately 10 μM hydroxychloroquine sulfate reduced the infection by 63%% and up to 75-96% inhibition was observed with 40-100 μM concentrations. A half-maximal inhibitory effect was estimated to occur at 7.5±1.0 μM hydroxychloroquine sulfate. These data clearly show that addition of hydroxychloroquine sulfate can effectively reduce the establishment of infection and spread of SARS-CoV2 if the drug is added immediately following virus adsorption. (FIG. 4).

Experiment 5: Results for Atazanavir Sulfate Treatment Prior to Infection

Experiments were carried out to determine the impact of atazanavir sulfate treatment on SARS-CoV2 infection as described above. Pretreatment with 0.1, 1, 5, 10, 15, 20 and 25 μM atazanavir sulfate reduced infectivity by 5, 15, 28, 46, 78, 92 and 100%, respectively. Reproducible results were obtained from three independent experiments. These data demonstrated that pretreatment of Vero E6 cells with atazanavir sulfate rendered these cells refractory to SARS-CoV2 infection. (FIG. 5).

Experiment 6: Results for Atazanavir Sulfate Treatment After Infection

The antiviral properties of atazanavir sulfate on SARS-CoV2 after the initiation of infection were studied as described above. When atazanavir sulfate was added after the initiation of infection, there was a dramatic dose dependent decrease in the number of virus antigen-positive cells. Approximately 11.0 μM atazanavir sulfate reduced the infection by 50% and up to 86%-96% inhibition was observed with 40-100 μM concentrations. A half-maximal inhibitory effect was estimated to occur at 11.5±1.0 μM atazanavir sulfate. These data clearly show that addition of atazanavir sulfate can effectively reduce the establishment of infection and spread of SARS-CoV2 if the drug is added immediately following virus adsorption. (FIG. 6).

Experiment 7: Results for Efavirenz Treatment Prior to Infection

Experiments were carried out to determine the impact of efavirenz treatment on SARS-CoV2 infection as described above. Permissive E6 cells were pre-treated with various concentrations of efavirenz (0.1-50 µM) for 18-24 hours prior to virus infection. Pretreatment with 0.1, 1, 10, 20, 30, 40 and 50 µM efavirenz reduced infectivity by 3%, 9%, 25%, 48%, 73%, 89% and 100%, respectively. Reproducible results were obtained from three independent experiments. These data demonstrated that pretreatment of Vero E6 cells with efavirenz rendered these cells refractory to SARS-CoV2 infection. (FIG. 7).

Experiment 8: Results for Efavirenz Treatment After Infection

The antiviral properties of efavirenz on SARS-CoV2 after the initiation of infection were studied as described above. When efavirenz was added after the initiation of infection, there was a dramatic dose dependent decrease in the number of virus antigen-positive cells. Approximately 55.0 μM efavirenz reduced the infection by 50% and up to 73%-96% inhibition was observed with 80-200 μM concentrations. A half-maximal inhibitory effect was estimated to occur at 51±1.0 μM efavirenz. These data clearly show that addition of efavirenz can effectively reduce the establishment of infection and spread of SARS-CoV2 if the drug is added immediately following virus adsorption. (FIG. 8).

Experiment 9: Results for Fosamprenavir Calcium Treatment Prior to Infection

Experiments were carried out to determine the impact of fosamprenavir calcium treatment on SARS-CoV2 infection as described above. Permissive E6 cells were pre-treated with various concentrations of fosamprenavir calcium (0.1-50 μM) for 18-24 hours prior to virus infection. Pretreatment with 0.1, 1, 10, 20, 30, 40 and 50 μM fosamprenavir calcium reduced infectivity by 3%, 10%, 28%, 55%, 73%, 91% and 100%, respectively. Reproducible results were obtained from three independent experiments. These data demonstrated that pretreatment of Vero E6 cells with fosamprenavir calcium rendered these cells refractory to SARS-CoV2 infection. (FIG. 9).

Experiment 10: Results for Fosamprenavir Calcium Treatment After Infection

The antiviral properties of fosamprenavir calcium on SARS-CoV2 after the initiation of infection were studied as described above. When fosamprenavir calcium was added after the initiation of infection, there was a dramatic dose dependent decrease in the number of virus antigen-positive cells. Approximately 58.0 μM fosamprenavir calcium reduced the infection by 50% and up to 75%-96% inhibition was observed with 80-200 μM concentrations. A half-maximal inhibitory effect was estimated to occur at 58±1.0 μM fosamprenavir calcium. These data clearly show that addition of fosamprenavir calcium can effectively reduce the establishment of infection and spread of SARS-CoV2 if the drug is added immediately following virus adsorption. (FIG. 10).

Experiment 11: Results for Saquinavir Treatment Prior to Infection

Experiments were carried out to determine the impact of saquinavir treatment on SARS-COV2 infection as described above. Permissive E6 cells were pre-treated with various concentrations of saquinavir (1-100 μM) for 18-24 hours prior to virus infection. Pretreatment with, 1, 10, 20, 40, 60, 80 and 100 μM saquinavir reduced infectivity by 5%, 16%, 35%, 47%, 78%, 85% and 100%, respectively. Reproducible results were obtained from three independent experiments. These data demonstrated that pretreatment of Vero E6 cells with saquinavir rendered these cells refractory to SARS-CoV2 infection. (FIG. 11).

Experiment 12: Results for Saquinavir Treatment After Infection

The antiviral properties of saquinavir on SARS-CoV2 after the initiation of infection were studied as described above. When was added after the initiation of infection, there was a significant dose dependent decrease in the number of virus antigen-positive cells. Approximately 95 μM fosamprenavir calcium reduced the infection by 50% and up to 63%-96% inhibition was observed with 120-240 μM concentrations. A half-maximal inhibitory effect was estimated to occur at 96±1.0 μM saquinavir. These data clearly show that addition of saquinavir can effectively reduce the establishment of infection and spread of SARS-CoV2 if the drug is added immediately following virus adsorption. (FIG. 12).

Experiment 13: Results for Remdesivir (GS-5734) Treatment Prior to Infection

Experiments were carried out to determine the impact of remdesivir treatment on SARS-COV2 infection as described above. Permissive E6 cells were pre-treated with various concentrations of remdesivir (1-25 μM) for 18-24 hours prior to virus infection. Pretreatment with, 0.1, 1, 5, 10, 15, 20 and 25 μM remdesivir reduced infectivity by 7%, 21%, 42%, 63%, 84%, 96% and 100%, respectively. Reproducible results were obtained from three independent experiments. These data demonstrated that pretreatment of Vero E6 cells with remdesivir rendered these cells refractory to SARS-CoV2 infection. (FIG. 13).

Experiment 14: Results for Remdesivir (GS-5734) Treatment After Infection

The antiviral properties of remdesivir on SARS-CoV2 after the initiation of infection were studied as described above. When was added after the initiation of infection, there was a significant dose dependent decrease in the number of virus antigen-positive cells. Approximately 2.4 μM remdesivir reduced the infection by 50% and up to 68%-96% inhibition was observed with 5-50 μM concentrations. A half-maximal inhibitory effect was estimated to occur at 2.4±1.0 μM remdesivir. These data clearly show that addition of remdesivir can effectively reduce the establishment of infection and spread of SARS-CoV2 if the drug is added immediately following virus adsorption. (FIG. 14).

Experiment 15: Results for Digoxin Treatment Prior to Infection

Experiments were carried out to determine the impact of digoxin treatment on SARS-CoV2 infection as described above. Permissive E6 cells were pre-treated with various concentrations of digoxin (0.05-5.00 μM) for 18-24 hours prior to virus infection. Pretreatment with, 0.05, 1.00, 2.00, 3.00, 4.00 and 5.00 μM digoxin reduced infectivity by 18%, 38%, 65%, 78%, 96%, 96% and 100%, respectively. Reproducible results were obtained from three independent experiments. These data demonstrated that pretreatment of Vero E6 cells with digoxin rendered these cells refractory to SARS-CoV2 infection. (FIG. 15).

Experiment 16: Results for Digoxin Treatment After Infection

The antiviral properties of digoxin on SARS-CoV2 after the initiation of infection were studied as described above. When was added after the initiation of infection, there was a significant dose dependent decrease in the number of virus antigen-positive cells. Approximately 0.17 μM digoxin reduced the infection by 50% and up to 73%-97% inhibition was observed with 0.20-0.50 μM concentrations. A half-maximal inhibitory effect was estimated to occur at 0.17±0.05 UM digoxin. These data clearly show that addition of digoxin can effectively reduce the establishment of infection and spread of SARS-CoV2 if the drug is added immediately following virus adsorption. (FIG. 16).

Animal Studies of Drugs in Oral Dosage Form

Experiment 17: Weight Loss Studies and Lung Titers Studies of Artemether and Atazanavir in Mice-Oral The SARS-CoV pathogenesis was confirmed and measured by weight loss and lung viral titers was similar in wild-type (WT) C57BL/6J and Ces1c−/− mice through the infection of age- and sex-matched mice from both strains. Mouse models of SARS-CoV disease show many aspects of SARS-CoV pathogenesis in humans including anorexia, high titers of virus replication in the lung, and the development of acute respiratory distress syndrome (ARDS) as well as an age-related exacerbation of disease (L. E. Gralinski, A. Bankhead III, S. Jeng, V. D. Menachery, S. Proll, S. E. Belisle, M. Matzke, B.-J. Webb-Robertson, M. L. Luna, A. K. Shukla, M. T. Ferris, M. Bolles, J. Chang, L. Aicher, K. M. Waters, R. D. Smith, T. O. Metz, G. L. Law, M. G. Katze, S. McWeeney, R. S. Baric, Mechanisms of severe acute respiratory syndrome coronavirus-induced acute lung injury MBio 4, e00271-13 (2013)).

Percent starting weight of Ces1c−/− mice infected with 104 PFU SARS-CoV MA15 treated beginning at −1 dpi with either vehicle (n=8) or Artemether (2 mg/kg) in oral powder/suspension, Atazanavir (4 mg/kg) in oral powder/suspension, or Artemether (2 mg/kg) plus Atazanavir (4 mg/kg) in oral power/suspension (n=24).

The weight loss studies and lung titers studies of Artemether and Atazanavir were summarized in FIG. 17 and FIG. 18 respectively. The results of the oral administration of Artemether and Atazanavir that substantially reduced the SARS-CoV-induced weight loss in infected mice, in addition to a significant reduction of lung titers thus demonstrating that combination therapy of Artemether and Atazanavir can reduce disease and suppress replication during an ongoing infection. These data suggest that a combination therapy of Artemether with Atazanavir significantly improved pulmonary function as compared to vehicle-treated controls.

Experiment 18: Weight Loss Studies and Lung Titers Studies of Cyclic Prolyl Glycine and Atazanavir in Mice-Oral Percent starting weight of Ces1c−/− mice infected with 104 PFU SARS-CoV MA15 treated beginning at −1 dpi with either vehicle (n=8) or Cyclic Prolyl Glycine (0.2 mg/kg) in oral powder/suspension, Atazanavir (4 mg/kg) in oral powder/suspension, or Cyclic Prolyl Glycine (0.2 mg/kg) plus Atazanavir (4 mg/kg) in oral power/suspension (n=24).

The weight loss studies and lung titers studies of Cyclic Prolyl Glycine and Atazanavir were summarized in FIG. 19 and FIG. 20 respectively. The results of the oral administration of Cyclic Prolyl Glycine and Atazanavir that substantially reduced the SARS-CoV-induced weight loss in infected mice, in addition to a significant reduction of lung titers thus demonstrating that combination therapy of Cyclic Prolyl Glycine and Atazanavir can reduce disease and suppress replication during an ongoing infection.

Experiment 19: Weight Lost Studies and Lung Titers Studies of Donepezil and Atazanavir in Mice-Oral Percent starting weight of Ces1c−/− mice infected with 104 PFU SARS-CoV MA15 treated beginning at −1 dpi with either vehicle (n=8) or Donepezil (0.15 mg/kg) in oral powder/suspension, Atazanavir (4 mg/kg) in oral powder/suspension, or Donepezil (0.15 mg/kg) plus Atazanavir (4 mg/kg) in oral power/suspension (n=24).

The weight loss studies and lung titers studies of Donepezil and Atazanavir were summarized in FIG. 21 and FIG. 22 respectively. The results of the oral administration of Donepezil and Atazanavir that substantially reduced the SARS-CoV-induced weight loss in infected mice, in addition to a significant reduction of lung titers thus demonstrating that combination therapy of Donepezil and Atazanavir can reduce disease and suppress replication during an ongoing infection.

Experiment 20: Weight Loss Studies and Lung Titers Studies of Memantine and Atazanavir in Mice-Oral Percent starting weight of Ces1c−/− mice infected with 104 PFU SARS-CoV MA15 treated beginning at −1 dpi with either vehicle (n=8) or Memantine (0.15 mg/kg) in oral powder/suspension, Atazanavir (4 mg/kg) in oral powder/suspension, or Memantine (0.15 mg/kg) plus Atazanavir (4 mg/kg) in oral power/suspension (n=24).

The weight loss studies and lung titers studies of Donepezil and Atazanavir were summarized in FIG. 23 and FIG. 24 respectively. The results of the oral administration of Memantine and Atazanavir that substantially reduced the SARS-CoV-induced weight loss in infected mice, in addition to a significant reduction of lung titers thus demonstrating that combination therapy of Memantine and Atazanavir can reduce disease and suppress replication during an ongoing infection.

Experiment 21: Weight Lost Studies and Lung Titers Studies of Rivastigmine and Atazanavir in Mice-Oral Percent starting weight of Ces1c−/− mice infected with 104 PFU SARS-CoV MA15 treated beginning at −1 dpi with either vehicle (n=8) or Rivastigmine (0.01 mg/kg) in oral powder/suspension, Atazanavir (4 mg/kg) in oral powder/suspension, or Rivastigmine (0.01 mg/kg) plus Atazanavir (4 mg/kg) in oral power/suspension (n=24).

The weight loss studies and lung titers studies of Donepezil and Atazanavir were summarized in FIG. 25 and FIG. 26 respectively.

The results of the oral administration of Rivastigmine and Atazanavir that substantially reduced the SARS-CoV-induced weight loss in infected mice, in addition to a significant reduction of lung titers thus demonstrating that combination therapy of Rivastigmine and Atazanavir can reduce disease and suppress replication during an ongoing infection.

Experiment 22: Weight Loss Studies and Lung Titers Studies of Galantamine and Atazanavir in Mice-Oral Percent starting weight of Ces1c−/− mice infected with 104 PFU SARS-CoV MA15 treated beginning at −1 dpi with either vehicle (n=8) or Galantamine (0.20 mg/kg) in oral powder/suspension, Atazanavir (4 mg/kg) in oral powder/suspension, or Galantamine (0.20 mg/kg) plus Atazanavir (4 mg/kg) in oral power/suspension (n=24).

The weight loss studies and lung titers studies of Donepezil and Atazanavir were summarized in FIG. 27 and FIG. 28 respectively.

The results of the oral administration of Galantamine and Atazanavir that substantially reduced the SARS-CoV-induced weight loss in infected mice, in addition to a significant reduction of lung titers thus demonstrating that combination therapy of Galantamine and Atazanavir can reduce disease and suppress replication during an ongoing infection.

Experiment 23: Weight Loss Studies and Lung Titers Studies of Valsartan and Atazanavir-in Mice-Oral Percent starting weight of Ces1c−/− mice infected with 104 PFU SARS-CoV MA15 treated beginning at −1 dpi with either vehicle (n=8) or Valsartan (2.00 mg/kg) in oral powder/suspension, Atazanavir (4 mg/kg) in oral powder/suspension, or Valsartan (2.00 mg/kg) plus Atazanavir (4 mg/kg) in oral power/suspension (n=24).

Figure 29:
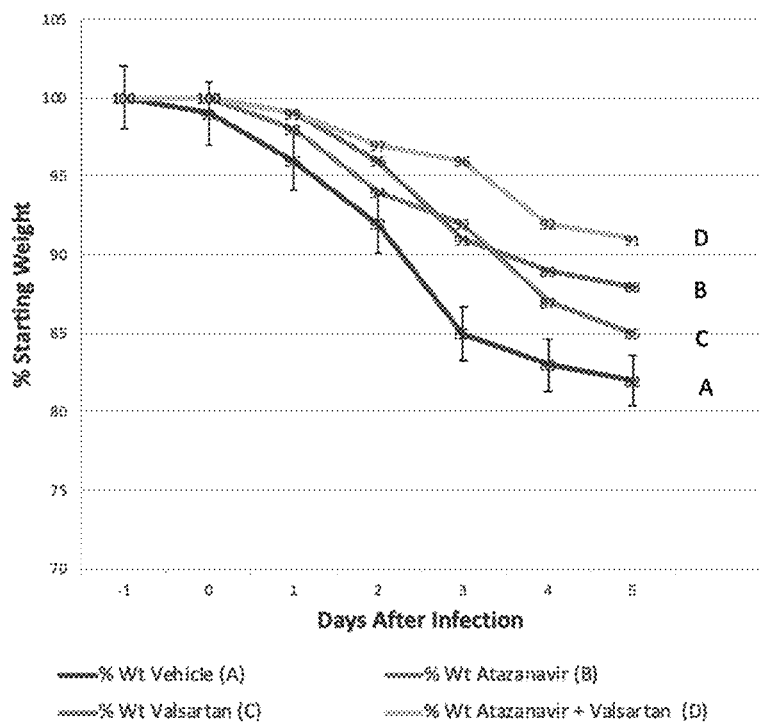
FIG. 29 generally depicts Weight Loss Studies of Valsartan and Atazanavir-Oral. Percent starting weight of Ces1c−/− mice infected with 104 PFU SARS-CoV MA15 treated beginning at −1 dpi with either vehicle (n=8) or Valsartan (2.00 mg/kg) in oral powder/suspension, Atazanavir (4 mg/kg) in oral powder/suspension, or Valsartan (2.00 mg/kg) plus Atazanavir (4 mg/kg) in oral power/suspension (n=24).
Figure 30:
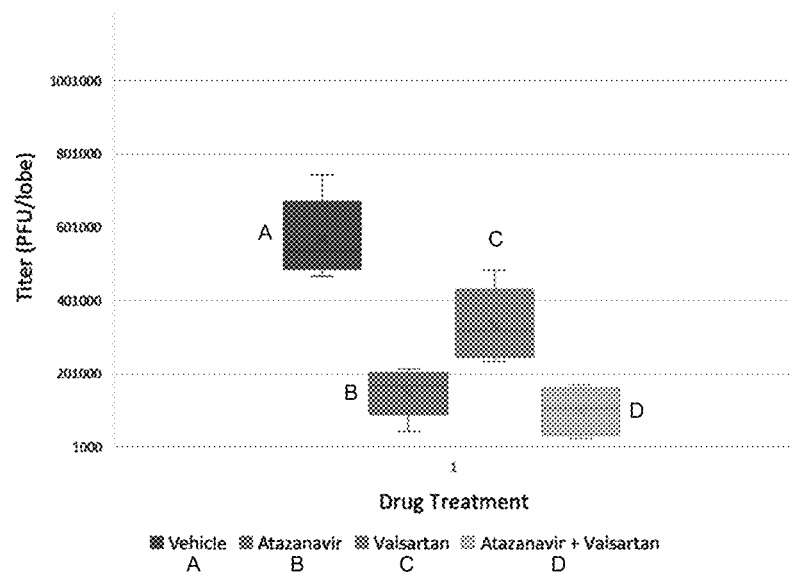
FIG. 30 generally depicts Lung Titers studies of Valsartan and Atazanavir and (Oral). SARS-CoV lung titers in mice infected and treated beginning at −1 dpi with either vehicle (n=8) or Valsartan (2.00 mg) in oral powder/suspension, Atazanavir (4 mg/kg) in oral powder/suspension, or Valsartan (2.00 mg) plus Atazanavir (4 mg/kg) in oral power/suspension (n=24).

The weight loss studies and lung titers studies of Donepezil and Atazanavir were summarized in FIG. 29 and FIG. 30 respectively.

The results of the oral administration of Valsartan and Atazanavir that substantially reduced the SARS-CoV-induced weight loss in infected mice, in addition to a significant reduction of lung titers thus demonstrating that combination therapy of Valsartan and Atazanavir can reduce disease and suppress replication during an ongoing infection.

Preparation of Nanoparticles Drug Formulation for Animal Studies

Experiment 24: Materials and Methods of Nanoparticles Preparation

Chitosan (CS) with a high degree of deacetylation of approximately 85%, low molecular weight with MW 3500-6500 was acquired from Sigma-Aldrich (St. Louis, Mo). Poly-L-γ-glutamic acid sodium salt (γ-PGA) with MW of 750,000 was purchased from Sigma-Aldrich (St. Louis, Mo). Acetic acid, cellulase (1.92 units/mg), fluorescein isothiocyanate (FITC), phosphate buffered saline (PBS), periodic acid, sodium acetate, formaldehyde, bismuth subnitrate, and Hanks balanced salt solution (HESS) were purchased from Sigma Chemical Co. (St. Louis, Mo.). Ethanol absolute anhydrous and potassium sodium tartrate were acquired from Fisher Scientific (Waltham, Massachusetts). Non-essential amino acid (NEAA) solution, fetal bovine serum (FBS), gentamicin and trypsin-EDTA were acquired from Gibco/Fisher Scientific (Grand Island, N.Y.). Eagle's minimal essential medium (MEM) was purchased from BioWest (Riverside, MO). All other chemicals and reagents used were of analytical grade.

Experiment 25: Preparation of the CS-γ-PGA Nanoparticles

Nanoparticles were obtained upon addition of γ-PGA aqueous solution (pH 7.4, 2 ml), using a pipette into a low-MW CS aqueous solution (pH 6.0, 10 ml) at varying concentrations (0.01%, 0.05%, 0.10%, 0.15%, or 0.20% by w/v) under magnetic stirring at room temperature. Nanoparticles were collected by ultracentrifugation at 38,000 rpm for 1 hour. Supernatants were discarded and nanoparticles were resuspended in deionized water for further studies. The electrostatic interaction between the two polyelectrolytes (γ-PGA and CS) instantaneously induced the formation of long hydrophobic segments with a high density of neutral ion-pairs, and thus resulted in highly neutralized complexes that segregated into colloidal nanoparticles Experiment 26: Preparation of Artemether Nanoparticles Artemether is (1R.4S,5R.8S.9R, 10S, 12R, 13R)-10-methoxy-1,5,9-trimethyl-11,14,15,16-tetraoxatetracyclo [10.3. 1.04, 13.08, 13]hexadecane Molecular Weight: 298.37 and CAS Number: 71963-77-4. Artemether is obtained from Sigma Aldrich (St Louis, MO, USA).

The net charge for artemether at pH 7.4 is slightly positive. Artemether is suitable to be incorporated in a core portion of a chitosan-shelled nanoparticles, wherein the core portion may include positively charged chitosan and negatively charged core substrate, such as γ-PGA or α-PGA. In other words, artemether may replace at least a portion of positively charged chitosan in the core portion by interacting with negatively core substrate, such as γ-PGA. In preparation, nanoparticles were obtained upon addition of a mixture of γ-PGA plus artemether aqueous solution (pH 7.4, 2 ml), using a pipette into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour Artemether is wholly or substantially totally encapsulated in the core portion of the nanoparticles. Supernatants were discarded and nanoparticles were resuspended in deionized water as the solution products Experiment 27: Preparation of Remdesivir (GS-5734) Nanoparticles Remdesivir is also called GS-5734 is 2-ethylbutyl (2S)-2-[[[(2R,3S,4R,5R)-5-(4-aminopyrrolo[2,1-f][1,2,4]triazin-7-yl)-5-cyano-3,4-dihydroxyoxolan-2-yl]methoxy-phenoxyphosphoryl]amino]propanoate.

Remdesivir Molecular Weight: 704.86- and CAS Number: 198904-31-3 was obtained from Sigma Aldrich ((St. Louis, MO, USA)

The net charge for Remdesivir at pH 7.4 is positive. GS-5734 is suitable to be incorporated in a core portion of a chitosan-shelled nanoparticles, wherein the core portion may include positively charged chitosan and negatively charged core substrate, such as γ-PGA or α-PGA. In other words, GS-5734 may replace at least a portion of positively charged chitosan in the core portion by interacting with negatively core substrate, such as γ-PGA. In preparation, nanoparticles were obtained upon addition of a mixture of γ-PGA plus GS-5734 aqueous solution (pH 7.4, 2 ml), using a pipette into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. GS-5734 is wholly or substantially totally encapsulated in the core portion of the nanoparticles. Supernatants were discarded and nanoparticles were resuspended in deionized water as the solution products.

Experiment 28: Preparation of Atazanavir Nanoparticles

Atazanavir is methyl N-[(1S)-1-{N'-[(2S,3S)-2-hydroxy-3-[(2S)-2-[(methoxycarbonyl)amino]-3,3-dimethylbutanamido]-4-phenylbutyl]-N'-{[4-(pyridin-yl)phenyl]methyl} hydrazinecarbonyl}-2.2-dimethylpropyl]carbamate.

Atazanavir molecular weight 704.8555 and CAS number is 198904-31-3, was obtained from Sigma Aldrich (St. Louis, MO, USA).

Atazanavir is suitable to be incorporated in a core portion of a chitosan-shelled nanoparticles, wherein the core portion may include positively charged chitosan and negatively charged core substrate, such as γ-PGA or α-PGA. The preparation of Atazanavir nanoparticles is described as above.

Experiment 29: Preparation of Valsartan Nanoparticles

Valsartan is (2S)-3-methyl-2-[pentanoyl]-[4-[2-(2H-tetrazol-5 yl)phenyl]phenyl methyl]amino]butanoic acid.

Valsartan Molecular Weight: 435.52, CAS Number: 137862-53-4 was obtained from (St. Louis, MO, USA).

The net charge for Valsartan at pH 7.4 is negative that is suitable to be incorporated in a core portion of a chitosan-shelled nanoparticles, wherein the core portion may include positively charged chitosan and negatively charged core substrate, such as γ-PGA or α-PGA. The preparation of Valsartan nanoparticles is described as above.

Experiment 30: Preparation of Digoxin Nanoparticles

Digoxin is 3-[(3S,5R,8R,9S, 10S, 12R, 13S, 14S, 17R)-3-[(2R,4S,5S,6R)-5-[(2S,4S,5S,6R)-5-[(2S,4S,5S,6R)-4,5-dihydroxy-6-methyloxan-2-yl]oxy-4-hydroxy-6-methyloxan-2-yl]oxy-4-hydroxy-6-methyloxan-2-yl]oxy-12,14-dihydroxy-10, 13-dimethyl-1,2,3,4,5,6,7,8,9, 11, 12, 15, 16, 17-tetradecahydrocyclopenta[a]phenanthren-17-yl]-2H-furan-5-one Digoxin Molecular Weight: 780.94, CAS Number: 20830-75-5 was obtained from Sigma Aldrich (St. Louis, MO, USA).

Digoxin is suitable to be incorporated in a core portion of a chitosan-shelled nanoparticles, wherein the core portion may include positively charged chitosan and negatively charged core substrate, such as γ-PGA or α-PGA. The preparation of Atazanavir nanoparticles is described as above.

Experiment 31: Preparation of Teriflunomide Nanoparticles

Teriflunomide is (2Z)-2-cyano-3-hydroxy-N-[4-(trifluoromethyl)phenyl]but-2-enamide.

Molecular weight: 270.21. CAS Number: 163451-81-8. Teriflunomide is obtained for animal testing from Sigma Aldrich (St. Louis, MO, USA).

Teriflunomide is suitable to be incorporated in a core portion of a chitosan-shelled nanoparticles, wherein the core portion may include positively charged chitosan and negatively charged core substrate, such as γ-PGA or α-PGA. The preparation of Teriflunomide nanoparticles is described as above.

Experiment 32: Preparation of Cyclic Prolyl Glycine Nanoparticles

Cyclic Prolyl Glycine is (S)-3,6-Dioxohexabydropyrrolo [1,2-a]pyrazine

Molecular Weight 154.17, CAS Number 3705-27-9 was obtained for animal testing from Sigma Aldrich (St. Louis, MO, USA).

Cyclic Prolyl Glycine is suitable to be incorporated in a core portion of a chitosan-shelled nanoparticles, wherein the core portion may include positively charged chitosan and negatively charged core substrate, such as γ-PGA or α-PGA The preparation of Teriflunomide nanoparticles is described as above.

Experiment 33: Preparation of Donepezil Hydrochloride Nanoparticles

Donepezil Hydrochloride is 1H-Inden-1-one, 2,3-dihydro-5,6-dimethoxy-2-[[1-(phenylmethyl)-4-piperidinyl] methyl]-, hydrochloride, Molecular Weight. 415 95 CAS Number: 120011-70-3 was obtained for animal testing from Sigma Aldrich (St. Louis, MO, USA).

Donepezil Hydrochloride is suitable to be incorporated in a core portion of a chitosan-shelled nanoparticles, wherein the core portion may include positively charged chitosan and negatively charged core substrate, such as γ-PGA or α-PGA. The preparation of Teriflunomide nanoparticles is described as above.

Experiment 34: Preparation of Memantine Hydrochloride Nanoparticles

Memantine Hydrochloride is 3,5-Dimethyl-1-adamantanamine hydrochloride, 3,5-Dimethylamantadine hydrochloride, 3,5-Dimethyltricyclo[3.3.1.13, 7]decan-1-amine hydrochloride Molecular Weight: 215.76, CAS Number: 41100-52-1, was obtained for animal testing from Sigma Aldrich (St. Louis, MO, USA).

Memantine Hydrochloride is suitable to be incorporated in a core portion of a chitosan-shelled nanoparticles, wherein the core portion may include positively charged chitosan and negatively charged core substrate, such as γ-PGA or α-PGA. The preparation of Teriflunomide nanoparticles is described as above.

Experiment 35: Preparation of Rivastigmine Tartrate Nanoparticles

Rivastigmine Tartrate is Ethylmethyl-carbamic acid 3-[(1S)-1-(dimethylamino)ethyl]phenyl ester, N-Ethyl-N-methyl-carbamic acid 3-[(1S)-1-(dimethylamino)ethyl]phenyl ester tartrate, S-Rivastigmine tartrate Molecular Weight: 400.42, CAS Number: 129101-54-8 was obtained for animal testing from Sigma Aldrich (St. Louis, MO, USA).

Rivastigmine Tartrate is suitable to be incorporated in a core portion of a chitosan-shelled nanoparticles, wherein the core portion may include positively charged chitosan and negatively charged core substrate, such as γ-PGA or α-PGA. The preparation of Teriflunomide nanoparticles is described as above.

Experiment 36: Preparation of Galantamine Hydrobromide Nanoparticles

Galantamine Hydrobromide is (1S, 12S, 14R)-9-methoxy-4-methyl-11-oxa-4-azatetracyclo[8.6.1.01, 12.06, 17]heptadeca-6(17), 7,9,15-tetraen-14-ol-bromide Molecular Weight: 368.27, CAS Number: 1953-04-4 was obtained for animal testing from Sigma Aldrich (St. Louis, MO, USA).

Galantamine Hydrobromide is suitable to be incorporated in a core portion of a chitosan-shelled nanoparticles, wherein the core portion may include positively charged chitosan and negatively charged core substrate, such as γ-PGA or α-PGA. The preparation of Teriflunomide nanoparticles is described as above.

Experiment 37: Preparation of Dexamethasone Nanoparticles

Dexamethasone is (8S,9R,10S, 11S, 13S, 14S, 16R, 17R)-9-fluoro-11, 17-dihydroxy-17-(2-hydroxyacetyl)-10, 13,16-trimethyl-6,7,8,11,12,14,15,16-octahydrocyclopenta[a] phenanthren-3-one Molecular Weight. 392.46

CAS Number: 50-02-2

Dexamethasone is suitable to be incorporated in a core portion of a chitosan-shelled nanoparticles, wherein the core portion may include positively charged chitosan and negatively charged core substrate, such as γ-PGA or α-PGA. The preparation of Teriflunomide nanoparticles is described as above.

Animal Studies

Materials and Methods

Viruses and cells. Recombinant mouse-adapted SARS-CoV (MA15) was propagated on Vero E6 cells, and its titer was determined. For virus titration, half of the right lung was used to give PFU per lung using Vero E6 cells with a detection limit of 100 PFU. All experiments were performed in a class II biological safety cabinet in a certified biosafety level 3 laboratory. (Deming D. Sheahan T, Heise M. Yount B, Davis N, Sims A. Suthar M, Harkema J, Whitmore A, Pickles R. West A. Donaldson E, Curtis K, Johnston R, Baric R 2006. Vaccine efficacy in senescent mice challenged with recombinant SARS-Cov bearing epidemic and zoonotic spike variants PLOS Med 3.e525. doi. 10.1371/journal.pmed.0030525).

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Experiment 38: Animal Studies of Artemether and GS-5734 Nanoparticles in Mice Male and female (25-to 28-week-old) mice were genetically deleted for carboxylesterase 1C (Ces1c−/−) (stock 014096, The Jackson Laboratory).

Animals were maintained in HEPA-filtered Micro-Isolator® Systems (Lab Products, Inc. Seaford, Delaware, USA). All animal studies and care were conducted in accordance with the Guide for the Care and Use of Laboratory Animals endorsed by the National Institutes of Health. (National Research Council. 2011. Guide for the care and use of laboratory animals, 8th ed. National Academy Press, Washington, DC.)

The animals were anesthetized with ketamine/xylazine and infected with 104 PFU/50 ml (prophylactic studies) or 103 PFU/50 ml (therapeutic studies) SARS-CoV MA15. Animals were weighed daily to monitor virus associated weight loss and to determine the appropriate dose volume of drugs (GS-5734) or vehicle. The drug or vehicle was administered intranasally 12 hours apart.

For each experiment there were initially 8 mice per drug-treated group and placebos. For studies involving intranasal treatments, mice were anesthetized as described above and treated with a 50-μl volume of saline alone (placebo) or saline containing drugs. The drugs are Artemether (4 mg/kg) in Chitosan nanoparticles, GS-5734 (4 mg/kg) in Chitosan nanoparticles, or Artemether (4 mg/kg) plus GS-5734 (4 mg/kg) in Chitosan nanoparticles. The drug solutions and placebo were administered twice a day for 5 days (at 12-h intervals) starting either 2 h prior to or 4 h after virus exposure.

On day 5 post infection (5 dpi) mice were sacrificed and necropsied for analysis of lung parameters (lung hemorrhage scores, weights, and virus titers). The lungs were weighed on a precision balance, followed by freezing at −80° C. for viral titration via plaque assay, as described by Gralinski et al. The inferior right lobe was placed in 10% buffered formalin and stored at 4° C. until histological analysis Weight loss significance was determined by Student's t test (Microsoft Excel) Aberrations in lung function were determined by WBP (Data Sciences International), as described by Menachery et al. (Gralinski L E, Bankhead A, III, Jeng S, Menachery V D, Proll S, Belisle S E, Matzke M, Webb-Robertson B-JM, Luna M L, Shukla A K, Ferris M T, Bolles M, Chang J, Aicher L, Waters K M, Smith R D, Metz T O, Law G L, Katze M G, McWeeney S, Baric R S. 2013. Mechanisms of severe acute respiratory syndrome coronavirus-induced acute lung injury. mBio 4(4): e00271-13. doi: 10.1128/mBio.00271-13.) (V. D. Menachery, L. E. Gralinski, R. S. Baric, M. T. Ferris, New metrics for evaluating viral respiratory pathogenesis PLOS ONE 10, e0131451 (2015).).

Artemether and GS-5734 can be incorporated in a core portion of a chitosan-shelled nanoparticles, wherein the core portion may include positively charged chitosan and negatively charged core substrate, such as γ-PGA or α-PGA. The preparation of artemether and GS-5734 nanoparticles is described above. Artemether and GS-5734 is wholly or substantially totally encapsulated in the core portion of the nanoparticles.

Figure 31:
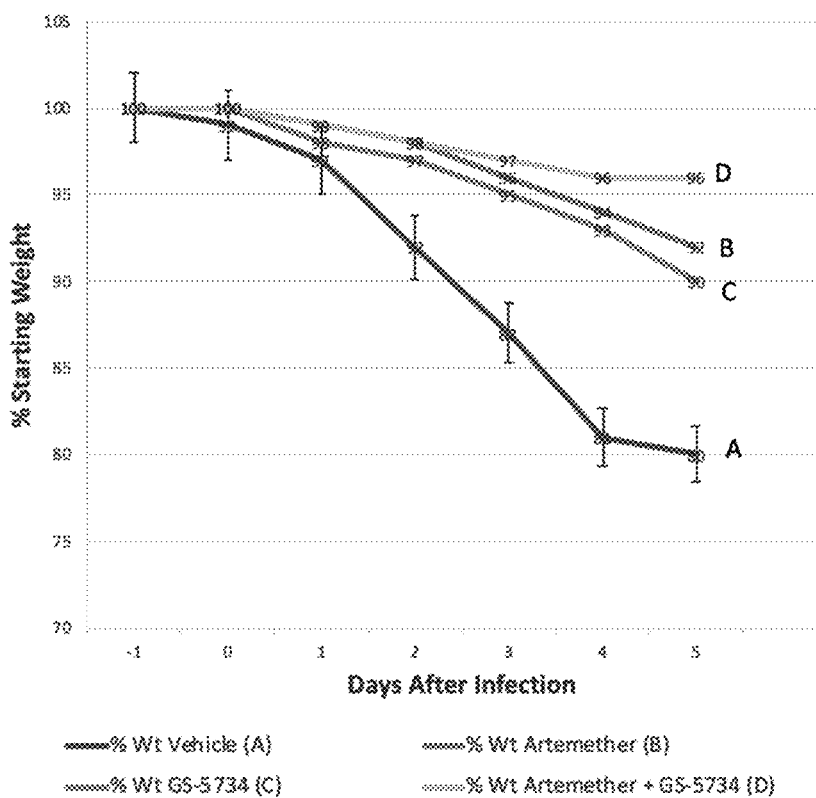
FIG. 31 generally depicts Weight loss studies of Artemether and GS-5734 (Intranasal). Percent starting weight of Ces1c−/− mice infected with 104 PFU SARS-CoV MA15 treated beginning at −1 dpi with either vehicle (n=8) or Artemether (4 mg/kg) in Chitosan nanoparticles, GS-5734 (4 mg/kg) in Chitosan nanoparticles, or Artemether (4 mg/kg) plus GS-5734 (4 mg/kg) in Chitosan nanoparticles (n=24).
Figure 32:
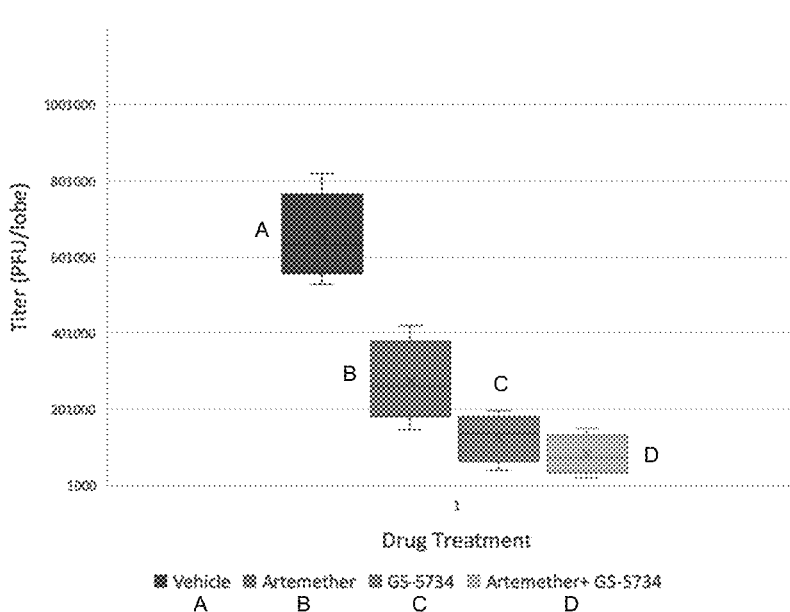
FIG. 32 generally depicts Lung Titers studies of Artemether and GS-5734 (intranasal). SARS-CoV lung titers in mice infected and treated beginning at −1 dpi with either vehicle (n=8) or Artemether (4 mg/kg) in Chitosan nanoparticles, GS-5734 (4 mg/kg) in Chitosan nanoparticles, or Artemether (4 mg/kg) plus GS-5734 (4 mg/kg) in Chitosan nanoparticles (n=24).

The weight loss studies and lung titers studies of Artemether and GS-5734 were summarized in FIG. 31 and FIG. 32 respectively.

The results of the intranasal administration of Artemether and GS-5734 that substantially reduced the SARS-CoV-induced weight loss in infected mice, thus demonstrating that combination therapy of Artemether GS-5734 can reduce disease and suppress replication during an ongoing infection. These data suggest that a combination therapy of Artemether with Remdesivir (GS-5734) significantly improved pulmonary function as compared to vehicle-treated controls.

The compounds mentioned in the summary section above, and elsewhere herein, can be preliminarily screened by in vitro assays for their efficacy against the replication of SARS-CoV2 virus. Other methods will also be apparent to those of ordinary skill in the art. These compounds can be further screened by in vivo assays.

Experiment 39: Animal Studies of GS-5734 and Valsartan Nanoparticles in Mice

GS-S734 and valsartan can be incorporated in a core portion of a chitosan-shelled nanoparticles, wherein the core portion may include positively charged chitosan and negatively charged core substrate, such as γ-PGA or α-PGA. The preparation of GS-5734 and valsartan nanoparticles is described above. GS-5734 and valsartan is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Valsartan (2 mg/kg) in Chitosan nanoparticles, GS-5734 (4 mg/kg) in Chitosan nanoparticles, or Valsartan (2 mg/kg) plus GS-5734 (4 mg/kg) in Chitosan nanoparticles (n=24).

Figure 33:
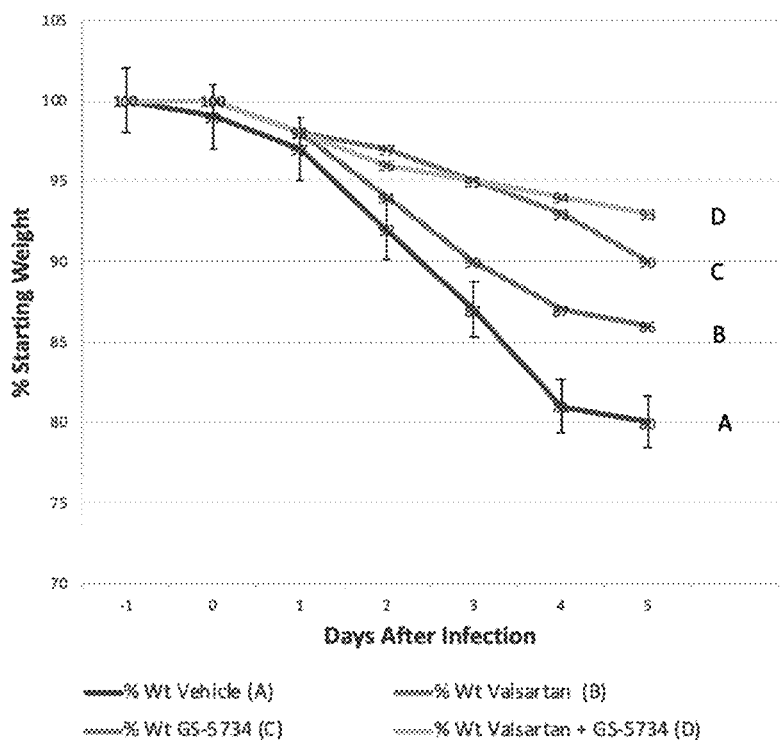
FIG. 33 generally depicts Weight loss studies of Valsartan and GS-5734 (Intranasal). Percent starting weight of Ces1c−/− mice infected with 104 PFU SARS-CoV MA15 treated beginning at −1 dpi with either vehicle (n=8) or Valsartan (2 mg/kg) in Chitosan nanoparticles, GS-5734 (4 mg/kg) in Chitosan nanoparticles, or Valsartan (2 mg/kg) plus GS-5734 (4 mg/kg) in Chitosan nanoparticles (n=24).
Figure 34:
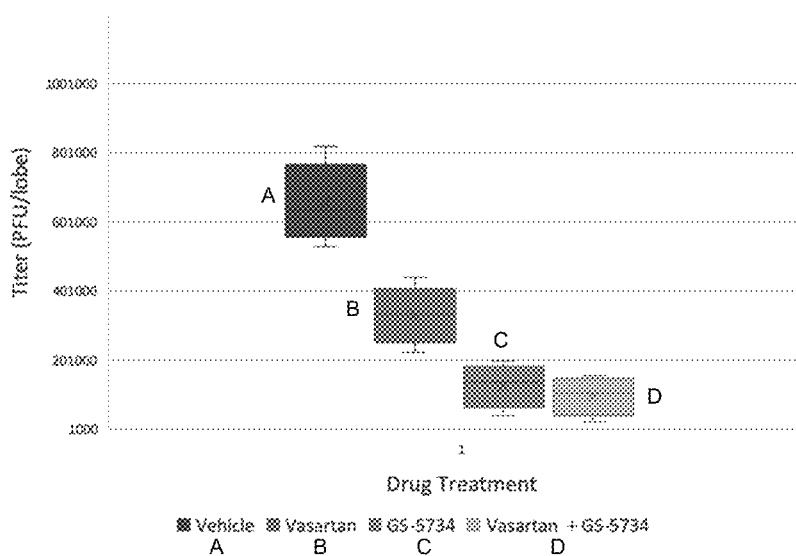
FIG. 34 generally depicts Lung Titers studies of Valsartan and GS-5734 (intranasal). SARS-CoV lung titers in mice infected and treated beginning at −1 dpi with either vehicle (n=8) or Valsartan (2 mg/kg) in Chitosan nanoparticles, GS-5734 (4 mg/kg) in Chitosan nanoparticles, or Valsartan (2 mg/kg) plus GS-5734 (4 mg/kg) in Chitosan nanoparticles (n=24).

The weight loss studies and lung titers studies of Valsartan and GS-5734 were summarized in FIG. 33 and FIG. 34 respectively.

The results of the intranasal administration of GS-5734 and Valsartan show reduced the SARS-CoV-induced weight loss in infected mice, thus demonstrating that combination therapy administration of GS-5734 and Valsartan can reduce disease and suppress replication during an ongoing infection.

Experiment 40: Animal Studies of GS-5734 and Atazanavir Nanoparticles in Mice

GS-5734 and atazanavir can be incorporated in a core portion of a chitosan-shelled nanoparticles, wherein the core portion may include positively charged chitosan and negatively charged core substrate, such as γ-PGA or α-PGA. The preparation of GS-5734 and atazanavir nanoparticles is described above. GS-5734 and atazanavir is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Atazanavir (4 mg/kg) in Chitosan nanoparticles, GS-5734 (4 mg/kg) in Chitosan nanoparticles, or Atazanavir (4 mg/kg) plus GS-5734 (4 mg/kg) in Chitosan nanoparticles (n=24).

Figure 35:
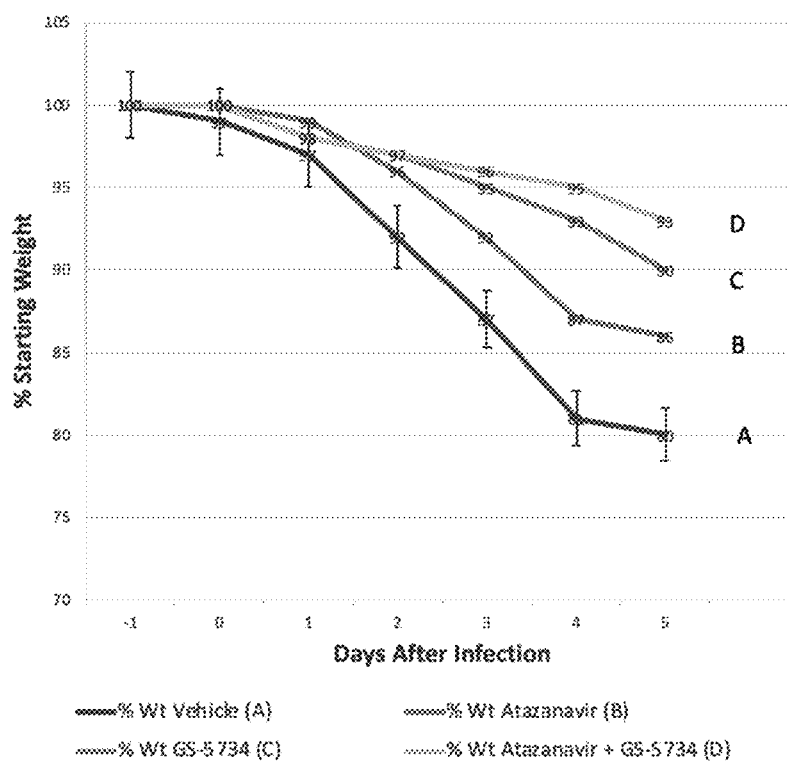
FIG. 35 generally depicts Weight loss studies of Atazanavir and GS-5734 (Intranasal). Percent starting weight of Ces1c−/− mice infected with 104 PFU SARS-CoV MA15 treated beginning at −1 dpi with either vehicle (n=8) or Atazanavir (4 mg/kg) in Chitosan nanoparticles, GS-5734 (4 mg/kg) in Chitosan nanoparticles, or Atazanavir (4 mg/kg) plus GS-5734 (4 mg/kg) in Chitosan nanoparticles (n=24).
Figure 36:
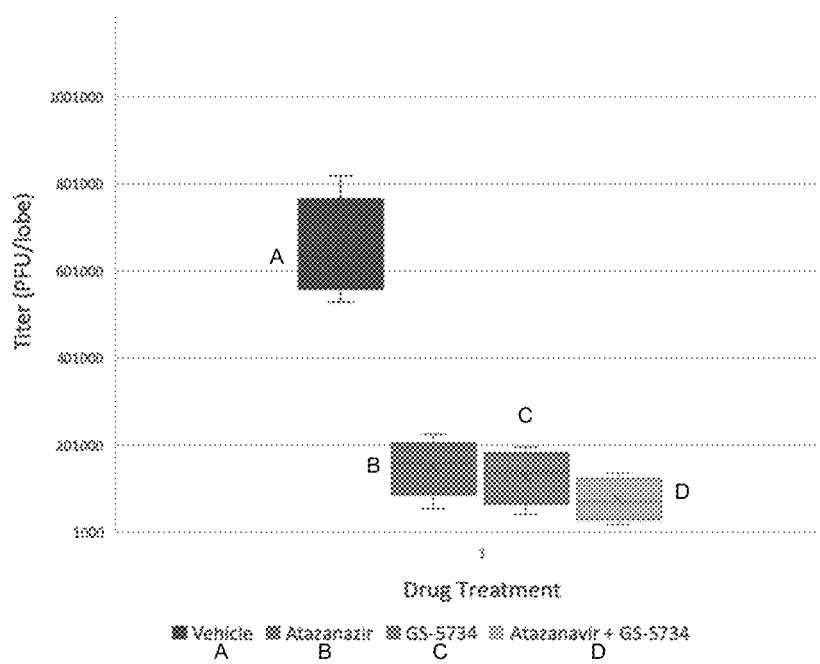
FIG. 36 generally depicts Lung Titers studies of Atazanavir and GS-5734 (intranasal). SARS-CoV lung titers in mice infected and treated beginning at −1 dpi with either vehicle (n=8) or Atazanavir (4 mg/kg) in Chitosan nanoparticles, GS-5734 (4 mg/kg) in Chitosan nanoparticles, or Atazanavir (4 mg/kg) plus GS-5734 (4 mg/kg) in Chitosan nanoparticles (n=24).

The weight loss studies and lung titers studies of atazanavir and GS-5734 were summarized in FIG. 35 and FIG. 36 respectively.

The results of the intranasal administration of GS-5734 and atazanavir show reduced the SARS-CoV-induced weight loss in infected mice, thus demonstrating that combination therapy administration of GS-5734 and atazanavir can reduce disease and suppress replication during an ongoing infection.

Experiment 41: Animal Studies of GS-5734 and Digoxin Nanoparticles in Mice

GS-5734 and digoxin can be incorporated in a core portion of a chitosan-shelled nanoparticles, wherein the core portion may include positively charged chitosan and negatively charged core substrate, such as γ-PGA or α-PGA. The preparation of GS-5734 and digoxin nanoparticles is described above. GS-5734 and digoxin is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Digoxin (10 μg/kg) in Chitosan nanoparticles, GS-5734 (4 mg/kg) in Chitosan nanoparticles, or Digoxin (10 μg/kg) plus GS-5734 (4 mg/kg) in Chitosan nanoparticles (n=24).

Figure 37:
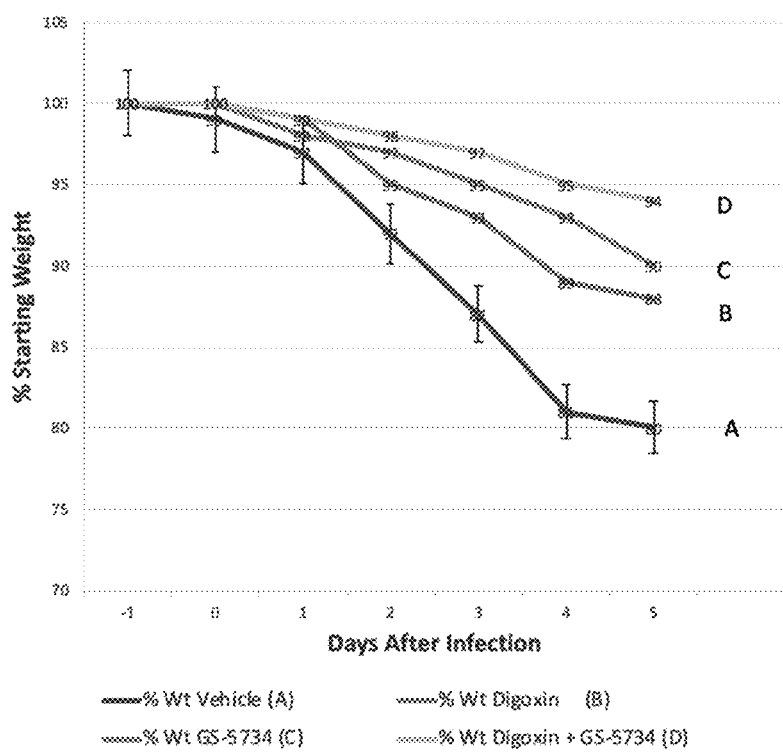
FIG. 37 generally depicts Weight loss studies of Digoxin and GS-5734 (Intranasal). Percent starting weight of Ces1c−/− mice infected with 104 PFU SARS-CoV MA15 treated beginning at −1 dpi with either vehicle (n=8) or Digoxin (10 μg/kg) in Chitosan nanoparticles, GS-5734 (4 mg/kg) in Chitosan nanoparticles, or Digoxin (10 μg/kg) plus GS-5734 (4 mg/kg) in Chitosan nanoparticles (n=24).
Figure 38:
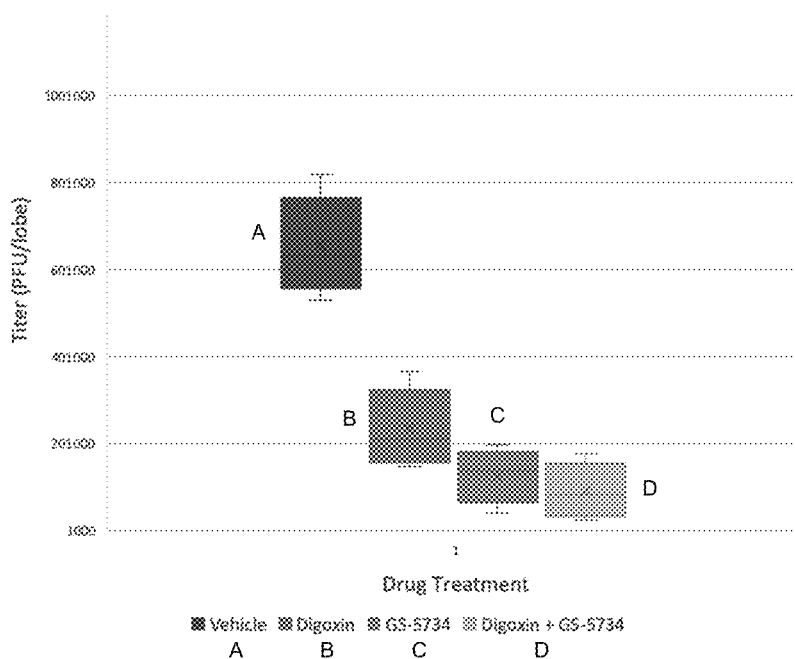
FIG. 38 generally depicts Lung Titers studies of Digoxin and GS-5734 (intranasal). SARS-CoV lung titers in mice infected and treated beginning at −1 dpi with either vehicle (n=8) or Digoxin (10 μg/kg) in Chitosan nanoparticles, GS-5734 (4 mg/kg) in Chitosan nanoparticles, or Digoxin (10 μg/kg) plus GS-5734 (4 mg/kg) in Chitosan nanoparticles (n=24).

The weight loss studies and lung titers studies of digoxin and GS-5734 were summarized in FIG. 37 and FIG. 38 respectively.

The results of the intranasal administration of GS-5734 and digoxin show reduced the SARS-COV-induced weight loss in infected mice, thus demonstrating that combination therapy administration of GS-5734 and digoxin can reduce disease and suppress replication during an ongoing infection.

Experiment 42: Animal Studies of GS-5734 and Teriflunomide Nanoparticles in Mice GS-5734 and teriflunomide can be incorporated in a core portion of a chitosan-shelled nanoparticles, wherein the core portion may include positively charged chitosan and negatively charged core substrate, such as γ-PGA or α-PGA. The preparation of GS-5734 and teriflunomide nanoparticles is described above. GS-5734 and teriflunomide is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Teriflunomide (0.2 mg/kg) in Chitosan nanoparticles, GS-5734 (4 mg/kg) in Chitosan nanoparticles, or Teriflunomide (0.2 mg/kg) plus GS-5734 (4 mg/kg) in Chitosan nanoparticles (n=24).

Figure 39:
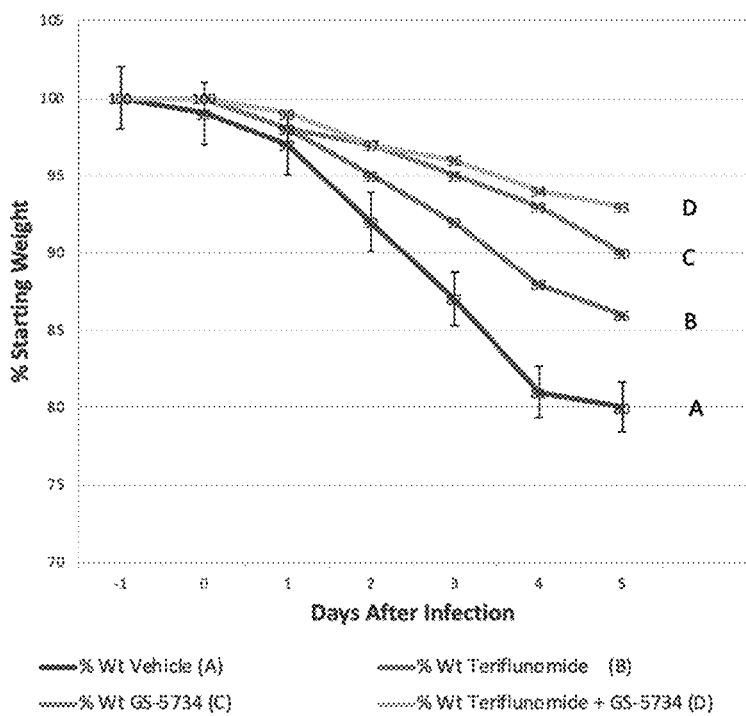
FIG. 39 generally depicts Weight loss studies of Teriflunomide and GS-5734 (Intranasal). Percent starting weight of Ces1c−/− mice infected with 104 PFU SARS-CoV MA15 treated beginning at −1 dpi with either vehicle (n=8) or Teriflunomide (0.2 mg/kg) in Chitosan nanoparticles, GS-5734 (4 mg/kg) in Chitosan nanoparticles, or Teriflunomide (0.2 mg/kg) plus GS-5734 (4 mg/kg) in Chitosan nanoparticles (n=24).
Figure 40:
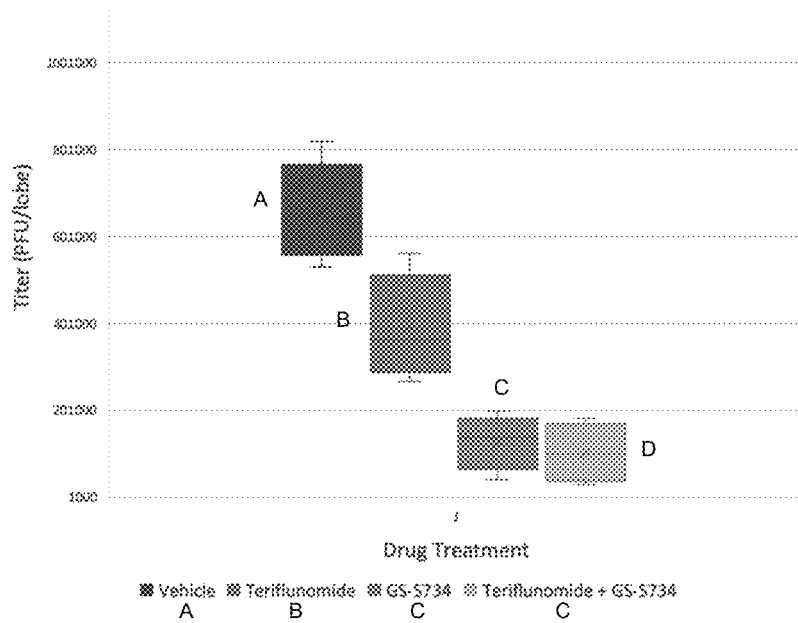
FIG. 40 generally depicts Lung Titers studies of Teriflunomide and GS-5734 (intranasal). SARS-CoV lung titers in mice infected and treated beginning at −1 dpi with either vehicle (n=8) or Teriflunomide (0.2 mg/kg) in Chitosan nanoparticles, GS-5734 (4 mg/kg) in Chitosan nanoparticles, or Teriflunomide (0.2 mg/kg) plus GS-5734 (4 mg/kg) in Chitosan nanoparticles (n=24).

The weight loss studies and lung titers studies of teriflunomide and GS-5734 were summarized in FIG. 39 and FIG. 40 respectively.

The results of the intranasal administration of GS-5734 and teriflunomide show reduced the SARS-CoV-induced weight loss in infected mice, thus demonstrating that combination therapy administration of GS-S734 and teriflunomide can reduce disease and suppress replication during an ongoing infection.

Experiment 43: Animal Studies of GS-5734 and Cyclic Prolyl Glycine Nanoparticles in Mice GS-5734 and Cyclic Prolyl Glycine can be incorporated in a core portion of a chitosan-shelled nanoparticles, wherein the core portion may include positively charged chitosan and negatively charged core substrate, such as γ-PGA or α-PGA. The preparation of GS-5734 and Cyclic Prolyl Glycine nanoparticles is described above. GS-$734 and Cyclic Prolyl Glycine is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Cyclic Prolyl Glycine (0.2 mg/kg) in Chitosan nanoparticles, GS-5734 (4 mg/kg) in Chitosan nanoparticles, or Cyclic Prolyl Glycine (0.2 mg/kg) plus GS-5734 (4 mg/kg) in Chitosan nanoparticles (n=24).

Figure 41:
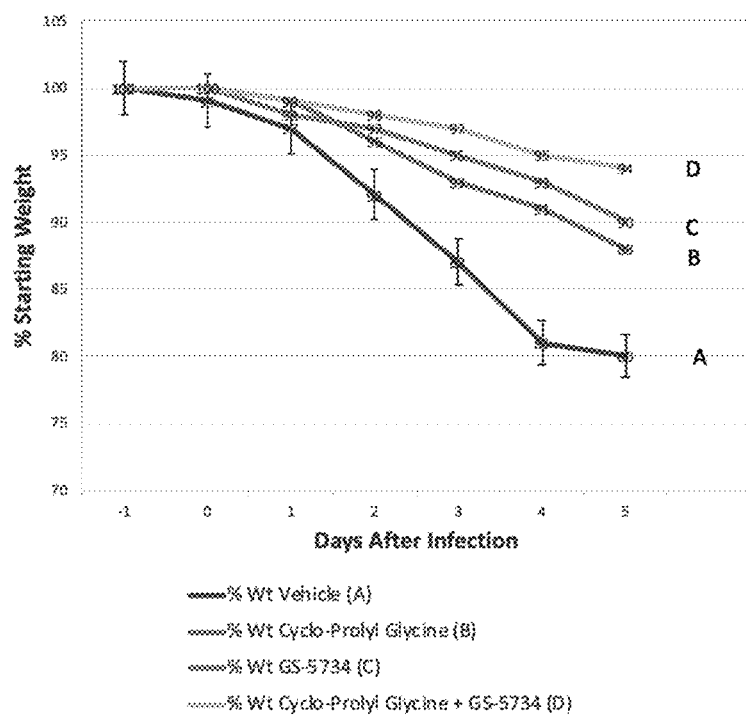
FIG. 41 generally depicts Weight loss studies of Cyclic Prolyl Glycine and GS-5734 (Intranasal). Percent starting weight of Ces1c−/− mice infected with 104 PFU SARS-CoV MA15 treated beginning at −1 dpi with either vehicle (n=8) or Cyclic Prolyl Glycine (0.2 mg/kg) in Chitosan nanoparticles, GS-5734 (4 mg/kg) in Chitosan nanoparticles, or Cyclic Prolyl Glycine (0.2 mg/kg) plus GS-5734 (4 mg/kg) in Chitosan nanoparticles (n=24).
Figure 42:
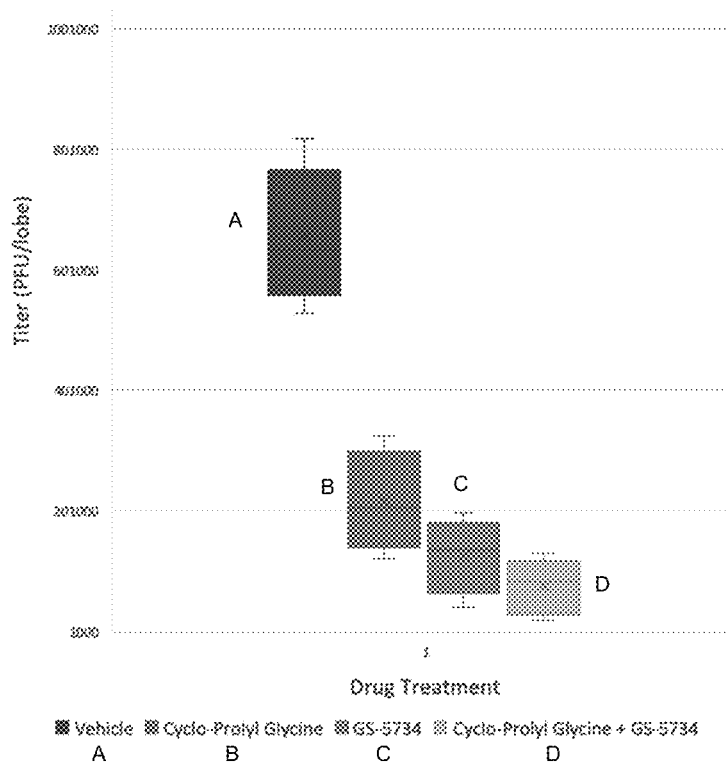
FIG. 42 generally depicts Lung Titers studies of Cyclic Prolyl Glycine and GS-5734 (intranasal). SARS-CoV lung titers in mice infected and treated beginning at −1 dpi with either vehicle (n=8) or Cyclic Prolyl Glycine (0.2 mg/kg) in Chitosan nanoparticles, GS-5734 (4 mg/kg) in Chitosan nanoparticles, or Cyclic Prolyl Glycine (0.2 mg/kg) plus GS-5734 (4 mg/kg) in Chitosan nanoparticles (n=24).

The weight loss studies and lung titers studies of Cyclic Prolyl Glycine and GS-5734 were summarized in FIG. 41 and FIG. 42 respectively.

The results of the intranasal administration of GS-5734 and Cyclic Prolyl Glycine show reduced the SARS-CoV-induced weight loss in infected mice, thus demonstrating that combination therapy administration of GS-$734 and Cyclic Prolyl Glycine can reduce disease and suppress replication during an ongoing infection.

Experiment 44: Animal Studies of Atazanavir and Cyclic Prolyl Glycine Nanoparticles in Mice Atazanavir and Cyclic Prolyl Glycine can be incorporated in a core portion of a chitosan-shelled nanoparticles, wherein the core portion may include positively charged chitosan and negatively charged core substrate, such as γ-PGA or α-PGA. The preparation of atazanavir and Cyclic Prolyl Glycine nanoparticles is described above. Atazanavir and Cyclic Prolyl Glycine is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Cyclic Prolyl Glycine (0.2 mg/kg) in Chitosan nanoparticles, Atazanavir (4 mg/kg) in Chitosan nanoparticles, or Cyclic Prolyl Glycine (0.2 mg/kg) plus Atazanavir (4 mg/kg) in Chitosan nanoparticles (n=24).

Figure 43:
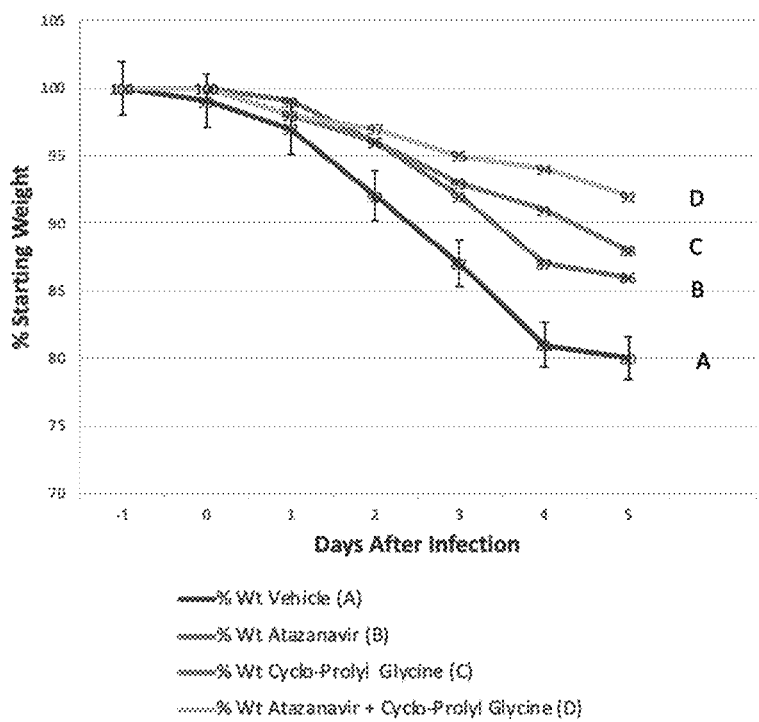
FIG. 43 generally depicts Weight loss studies of Cyclic Prolyl Glycine and Atazanavir (Intranasal). Percent starting weight of Ces1c−/− mice infected with 104 PFU SARS-CoV MA15 treated beginning at −1 dpi with either vehicle (n=8) or Cyclic Prolyl Glycine (0.2 mg/kg) in Chitosan nanoparticles, Atazanavir (4 mg/kg) in Chitosan nanoparticles, or Cyclic Prolyl Glycine (0.2 mg/kg) plus Atazanavir (4 mg/kg) in Chitosan nanoparticles (n=24).
Figure 44:
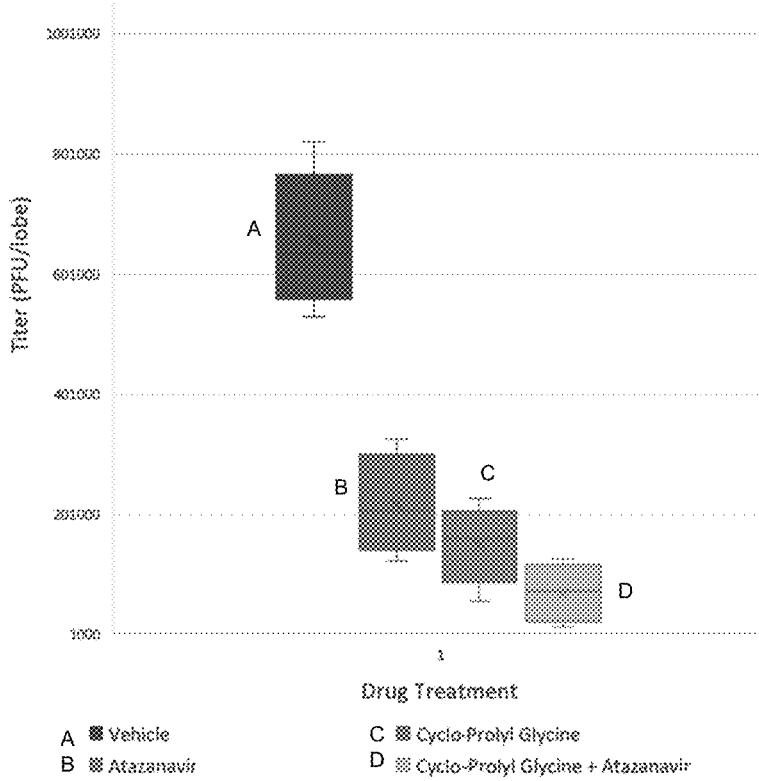
FIG. 44 generally depicts Lung Titers studies of Cyclic Prolyl Glycine and Atazanavir (intranasal). SARS-CoV lung titers in mice infected and treated beginning at −1 dpi with either vehicle (n=8) or Cyclic Prolyl Glycine (0.2 mg/kg) in Chitosan nanoparticles, Atazanavir (4 mg/kg) in Chitosan nanoparticles, or Cyclic Prolyl Glycine (0.2 mg/kg) and Atazanavir (4 mg/kg) in Chitosan nanoparticles (n=24).

The weight loss studies and lung titers studies of atazanavir and Cyclic Prolyl Glycine were summarized in FIG. 43 and FIG. 44 respectively.

The results of the intranasal administration of atazanavir and Cyclic Prolyl Glycine show reduced the SARS-CoV-induced weight loss in infected mice, thus demonstrating that combination therapy administration of atazanavir and Cyclic Prolyl Glycine can reduce disease and suppress replication during an ongoing infection.

Experiment 45: Animal Studies of Teriflunomide and Cyclic Prolyl Glycine Nanoparticles in Mice Teriflunomide and Cyclic Prolyl Glycine can be incorporated in a core portion of a chitosan-shelled nanoparticles, wherein the core portion may include positively charged chitosan and negatively charged core substrate, such as γ-PGA or α-PGA. The preparation of teriflunomide and Cyclic Prolyl Glycine nanoparticles is described above. Teriflunomide and Cyclic Prolyl Glycine is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Teriflunomide (0.2 mg/kg) in Chitosan nanoparticles, Cyclic Prolyl Glycine (0.2 mg/kg) in Chitosan nanoparticles, or Teriflunomide (0.2 mg/kg) plus Cyclic Prolyl Glycine (0.2 mg/kg) in Chitosan nanoparticles (n=24).

Figure 45:
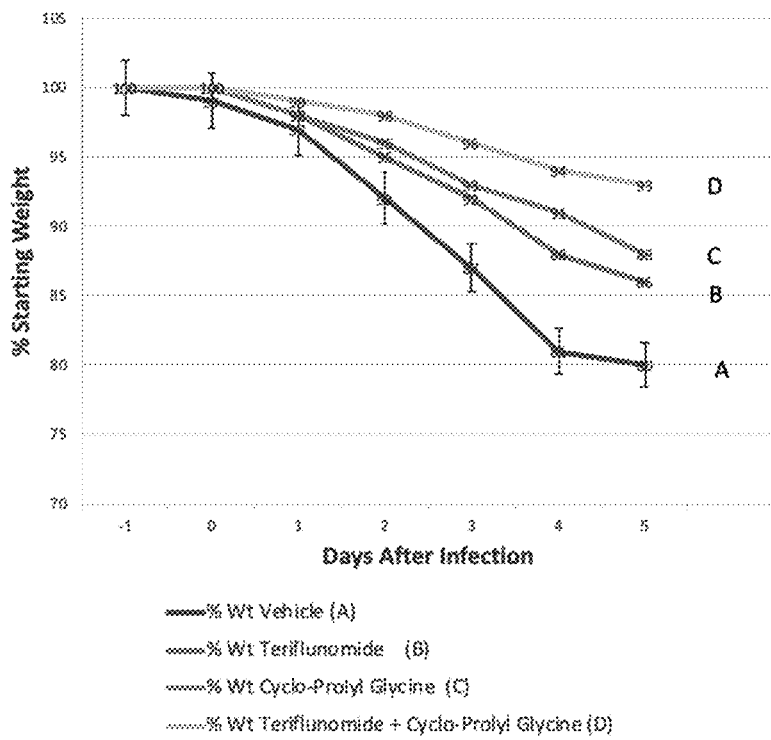
FIG. 45 generally depicts Weight loss studies of Teriflunomide and Cyclic Prolyl Glycine (Intranasal). Percent starting weight of Ces1c−/− mice infected with 104 PFU SARS-CoV MA15 treated beginning at −1 dpi with either vehicle (n=8) or Teriflunomide (0.2 mg/kg) in Chitosan nanoparticles, Cyclic Prolyl Glycine (0.2 mg/kg) in Chitosan nanoparticles, or Teriflunomide (0.2 mg/kg) plus Cyclic Prolyl Glycine (0.2 mg/kg) in Chitosan nanoparticles (n=24).
Figure 46:
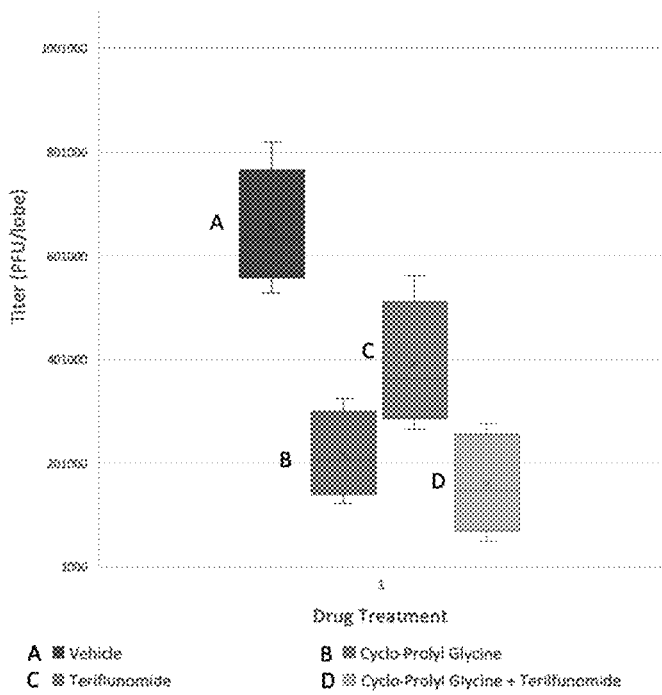
FIG. 46 generally depicts Lung Titers studies of Teriflunomide and Cyclic Prolyl Glycine (intranasal). SARS-CoV lung titers in mice infected and treated beginning at −1 dpi with either vehicle (n=8) or Teriflunomide (0.2 mg/kg) in Chitosan nanoparticles, Cyclic Prolyl Glycine (0.2 mg/kg) in Chitosan nanoparticles, or Teriflunomide (0.2 mg/kg) plus Cyclic Prolyl Glycine (0.2 mg/kg) in Chitosan nanoparticles (n=24).

The weight loss studies and lung titers studies of teriflunomide and Cyclic Prolyl Glycine were summarized in FIG. 45 and FIG. 46 respectively.

The results of the intranasal administration of teriflunomide and Cyclic Prolyl Glycine show reduced the SARS-CoV-induced weight loss in infected mice, thus demonstrating that combination therapy administration of teriflunomide and Cyclic Prolyl Glycine can reduce disease and suppress replication during an ongoing infection.

Experiment 46: Animal Studies of GS-5734 and Donepezil Nanoparticles in Mice

GS-5734 and donepezil can be incorporated in a core portion of a chitosan-shelled nanoparticles, wherein the core portion may include positively charged chitosan and negatively charged core substrate, such as γ-PGA or α-PGA. The preparation of GS-5734 and donepezil nanoparticles is described above. GS-5734 and donepezil is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or donepezil (0.15 mg/kg) in Chitosan nanoparticles, GS-5734 (4 mg/kg) in Chitosan nanoparticles, or donepezil (0.15 mg/kg) plus GS-5734 (4 mg/kg) in Chitosan nanoparticles (n=24).

Figure 47:
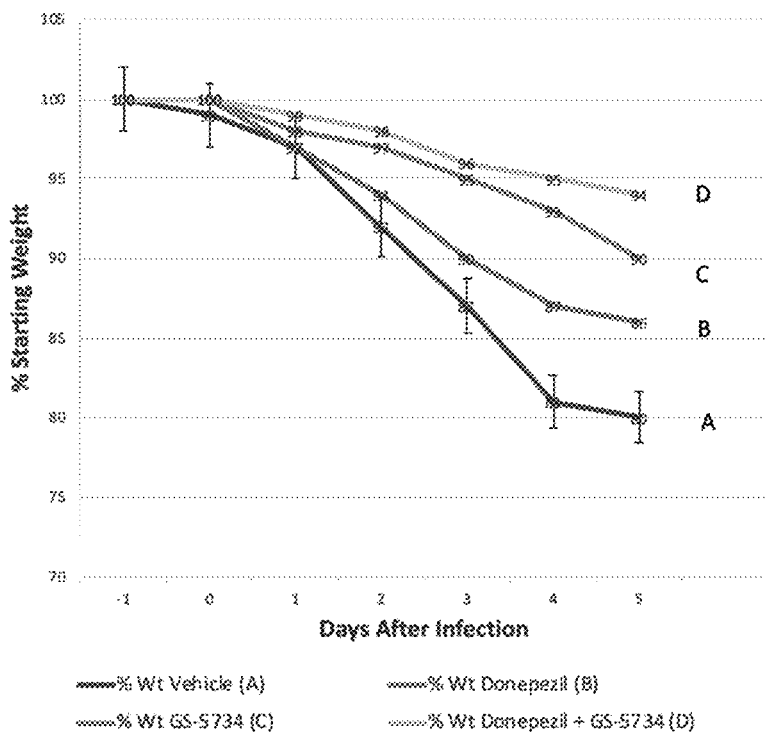
FIG. 47 generally depicts Weight loss studies of Donepezil and GS-5734 (Intranasal). Percent starting weight of Ces1c−/− mice infected with 104 PFU SARS-CoV MA15 treated beginning at −1 dpi with either vehicle (n=8) or Donepezil (0.15 mg/kg) in Chitosan nanoparticles, GS-5734

The weight loss studies and lung titers studies of donepezil and GS-5734 were summarized in FIG. 47 and FIG. 48 respectively.

The results of the intranasal administration of GS-5734 and donepezil show reduced the SARS-CoV-induced weight loss in infected mice, thus demonstrating that combination therapy administration of GS-5734 and donepezil can reduce disease and suppress replication during an ongoing infection.

Experiment 47: Animal Studies of GS-5734 and Memantine Nanoparticles in Mice

GS-5734 and memantine can be incorporated in a core portion of a chitosan-shelled nanoparticles, wherein the core portion may include positively charged chitosan and negatively charged core substrate, such as γ-PGA or α-PGA. The preparation of GS-5734 and memantine nanoparticles is described above. GS-5734 and memantine is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Memantine (0.15 mg/kg) in Chitosan nanoparticles, GS-5734 (4 mg/kg) in Chitosan nanoparticles, or Memantine (0.15 mg/kg) plus GS-5734 (4 mg/kg) in Chitosan nanoparticles (n=24).

The weight loss studies and lung titers studies of d memantine and GS-5734 were summarized in FIG. 49 and FIG. 50 respectively.

The results of the intranasal administration of GS-5734 and memantine show reduced the SARS-CoV-induced weight loss in infected mice, thus demonstrating that combination therapy administration of GS-5734 and memantine can reduce disease and suppress replication during an ongoing infection.

Experiment 48: Animal Studies of GS-5734 and Rivastigmine Nanoparticles in Mice

GS-S734 and rivastigmine can be incorporated in a core portion of a chitosan-shelled nanoparticles, wherein the core portion may include positively charged chitosan and negatively charged core substrate, such as γ-PGA or α-PGA. The preparation of GS-5734 and rivastigmine nanoparticles is described above. GS-5734 and rivastigmine is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Rivastigmine (0.01 mg/kg) in Chitosan nanoparticles, GS-5734 (4 mg/kg) in Chitosan nanoparticles, or Rivastigmine (0.4 mg/kg) plus GS-5734 (4 mg/kg) in Chitosan nanoparticles (n=24).

The weight loss studies and lung titers studies of rivastigmine and GS-5734 were summarized in FIG. 51 and FIG. 52 respectively.

The results of the intranasal administration of GS-5734 and rivastigmine show reduced the SARS-CoV-induced weight loss in infected mice, thus demonstrating that combination therapy administration of GS-5734 and rivastigmine can reduce disease and suppress replication during an ongoing infection.

Experiment 49: Animal Studies of GS-5734 and Galantamine Nanoparticles in Mice

GS-5734 and galantamine can be incorporated in a core portion of a chitosan-shelled nanoparticles, wherein the core portion may include positively charged chitosan and negatively charged core substrate, such as γ-PGA or α-PGA. The preparation of GS-5734 and galantamine nanoparticles is described above. GS-5734 and galantamine is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Rivastigmine (0.01 mg/kg) in Chitosan nanoparticles, GS-5734 (4 mg/kg) in Chitosan nanoparticles, or Rivastigmine (0.4 mg/kg) plus GS-5734 (4 mg/kg) in Chitosan nanoparticles (n=24).

The weight loss studies and lung titers studies of galantamine and GS-5734 were summarized in FIG. 53 and FIG. 54 respectively.

The results of the intranasal administration of GS-5734 and galantamine show reduced the SARS-CoV-induced weight loss in infected mice, thus demonstrating that combination therapy administration of GS-S734 and galantamine can reduce disease and suppress replication during an ongoing infection.

Experiment 50: Animal Studies of Cyclic Profyl Glycine and Dexamethasone in Mice-Oral Percent starting weight of Ces1c−/− mice infected with 104 PFU SARS-CoV MA15 treated beginning at −1 dpi with either vehicle (n=8) or Cyclic Prolyl Glycine (0.2 mg/kg) in oral powder/suspension, Dexamethasone (0.1 mg/kg) in oral powder/suspension, or Cyclic Prolyl Glycine (0.2 mg/kg) plus Dexamethasone (0.1 mg/kg) in oral power/suspension (n=24).

The weight loss studies and lung titers studies of Cyclic Prolyl Glycine and were Dexamethasone summarized in FIG. 55 and FIG. 56 respectively. The results of the oral administration of Cyclic Prolyl Glycine and Dexamethasone that substantially reduced the SARS-COV-induced weight loss in infected mice, in addition to a significant reduction of lung titers thus demonstrating that combination therapy of Cyclic Prolyl Glycine and Dexamethasone can reduce disease and suppress replication during an ongoing infection.

Experiment 51: Animal Studies of Donepezil and Dexamethasone in Mice-Oral

Percent starting weight of Ces1c−/− mice infected with 104 PFU SARS-CoV MA15 treated beginning at −1 dpi with either vehicle (n=8) or Donepezil (0.15 mg/kg) in oral powder/suspension, Dexamethasone (0.1 mg/kg) in oral powder/suspension, or Donepezil (0.15 mg/kg) plus Dexamethasone (0.1 mg/kg) in oral power/suspension (n=24).

The weight loss studies and lung titers studies of Donepezil and Dexamethasone were summarized in FIG. 57 and FIG. 58 respectively. The results of the oral administration of Donepezil and Dexamethasone that substantially reduced the SARS-CoV-induced weight loss in infected mice, in addition to a significant reduction of lung titers thus demonstrating that combination therapy of Donepezil and Dexamethasone can reduce disease and suppress replication during an ongoing infection.

Experiment 52: Animal Studies of Atazanavir and Dexamethasone in Mice-Oral

Percent starting weight of Ces1c−/− mice infected with 104 PFU SARS-CoV MA15 treated beginning at −1 dpi with either vehicle (n=8) or Atazanavir (4.00 mg/kg) in oral powder/suspension, Dexamethasone (0.1 mg/kg) in oral powder/suspension, or Atazanavir (4.00 mg/kg) plus Dexamethasone (0.1 mg/kg) in oral power/suspension (n=24).

The weight loss studies and lung titers studies of Atazanavir and Dexamethasone were summarized in FIG. 59 and FIG. 60 respectively. The results of the oral administration of Atazanavir and Dexamethasone that substantially reduced the SARS-CoV-induced weight loss in infected mice, in addition to a significant reduction of lung titers thus demonstrating that combination therapy of Atazanavir and Dexamethasone can reduce disease and suppress replication during an ongoing infection.

Experiment 53: Animal Studies of GS-5734 and Dexamethasone Nanoparticles in Mice GS-$734 and Dexamethasone can be incorporated in a core portion of a chitosan-shelled nanoparticles, wherein the core portion may include positively charged chitosan and negatively charged core substrate, such as γ-PGA or α-PGA. The preparation of GS-5734 and Dexamethasone nanoparticles is described above. GS-5734 and Dexamethasone is wholly or substantially totally encapsulated in the core portion of the nanoparticles.

Experimental parameters:

Percent starting weight of Ces1c−/− mice infected with 104 PFU SARS-CoV MA15 treated beginning at −1 dpi with either vehicle (n=8) or Dexamethasone (0.10 mg/kg) in Chitosan nanoparticles, GS-5734 (4 mg/kg) in Chitosan nanoparticles, or Dexamethasone (0.10 mg/kg) plus GS-5734 (4 mg/kg) in Chitosan nanoparticles (n=24).

The weight loss studies and lung titers studies of Dexamethasone and GS-5734 were summarized in FIG. 61 and FIG. 62 respectively.

The results of the intranasal administration of GS-5734 and Dexamethasone show reduced the SARS-CoV-induced weight loss in infected mice, thus demonstrating that combination therapy administration of GS-5734 and Dexamethasone can reduce disease and suppress replication during an ongoing infection.

Experiment 54: Animal Studies of Cyclic Prolyl Glycine and Methylprednisolone in Mice-Oral Percent starting weight of Ces1c−/− mice infected with 104 PFU SARS-CoV MA15 treated beginning at −1 dpi with either vehicle (n=8) or Cyclic Prolyl Glycine (0.2 mg/kg) in oral powder/suspension, Methylprednisolone (0.5 mg/kg) in oral powder/suspension, or Cyclic Prolyl Glycine (0.2 mg/kg) plus Methylprednisolone (0.5 mg/kg) in oral power/suspension (n=24).

The weight loss studies and lung titers studies of Cyclic Prolyl Glycine and were Methylprednisolone summarized in FIG. 63 and FIG. 64 respectively. The results of the oral administration of Cyclic Prolyl Glycine and Methylprednisolone that substantially reduced the SARS-CoV-induced weight loss in infected mice, in addition to a significant reduction of lung titers thus demonstrating that combination therapy of Cyclic Prolyl Glycine and Methylprednisolone can reduce disease and suppress replication during an ongoing infection.

Experiment 55: Animal Studies of Donepezil and Methylprednisolone Mice-Oral

Percent starting weight of Ces1c−/− mice infected with 104 PFU SARS-CoV MA15 treated beginning at −1 dpi with either vehicle (n=8) or Donepezil (0.15 mg/kg) in oral powder/suspension, Methylprednisolone (0.5 mg/kg) in oral powder/suspension, or Donepezil (0.15 mg/kg) plus Dexamethasone (0.1 mg/kg) in oral power/suspension (n=24).

The weight loss studies and lung titers studies of Donepezil and Methylprednisolone were summarized in FIG. 65 and FIG. 66 respectively. The results of the oral administration of Donepezil and Methylprednisolone that substantially reduced the SARS-CoV-induced weight loss in infected mice, in addition to a significant reduction of lung titers thus demonstrating that combination therapy of Donepezil and Methylprednisolone can reduce disease and suppress replication during an ongoing infection.

Experiment 56: Animal Studies of Teriflunomide and Dexamethasone Mice-Oral

Percent starting weight of Ces1c−/− mice infected with 104 PFU SARS-CoV MA15 treated beginning at −1 dpi with either vehicle (n=8) or Teriflunomide (0.20 mg/kg) in oral powder/suspension, Dexamethasone (0.10 mg/kg) in oral powder/suspension, or Donepezil (0.15 mg/kg) plus Dexamethasone (0.1 mg/kg) in oral power/suspension (n=24).

The weight loss studies and lung titers studies of Donepezil and Dexamethasone were summarized in FIG. 67 and FIG. 68 respectively. The results of the oral administration of Teriflunomide and Dexamethasone that substantially reduced the SARS-CoV-induced weight loss in infected mice, in addition to a significant reduction of lung titers thus demonstrating that combination therapy of Teriflunomide and Dexamethasone can reduce disease and suppress replication during an ongoing infection.

Experiment 57: Animal Studies of Teriflunomide and Methylprednisolone Mice-Oral

Percent starting weight of Ces1c−/− mice infected with 104 PFU SARS-CoV MA15 treated beginning at −1 dpi with either vehicle (n=8) or Teriflunomide (0.20 mg/kg) in oral powder/suspension, Methylprednisolone (0.50 mg/kg) in oral powder/suspension, or Donepezil (0.15 mg/kg) plus Methylprednisolone (0.50 mg/kg) in oral power/suspension (n=24).

The weight loss studies and lung titers studies of Teriflunomide and Methylprednisolone were summarized in FIG. 69 and FIG. 70 respectively. The results of the oral administration of Teriflunomide and Methylprednisolone that substantially reduced the SARS-CoV-induced weight loss in infected mice, in addition to a significant reduction of lung titers thus demonstrating that combination therapy of Teriflunomide and Methylprednisolone can reduce disease and suppress replication during an ongoing infection.

Experiment 58: Animal Studies of Cyclic Prolyd Glycine and Ivermectin-Oral

Percent starting weight of Ces1c−/− mice infected with 104 PFU SARS-CoV MA15 treated beginning at −1 dpi with either vehicle (n=8) or Cyclic Prolyl Glycine (0.2 mg/kg) in oral powder/suspension, Ivermectin (0.4 mg/kg) in oral powder/suspension, or Cyclic Prolyl Glycine (0.2 mg/kg) plus Ivermectin (0.4 mg/kg) in oral power/suspension (n=24).

The weight loss studies and lung titers studies of Cyclic Prolyl Glycine and were Methylprednisolone summarized in FIG. 71 and FIG. 72 respectively. The results of the oral administration of Cyclic Prolyl Glycine and Ivermectin that substantially reduced the SARS-CoV-induced weight loss in infected mice, in addition to a significant reduction of lung titers thus demonstrating that combination therapy of Cyclic Prolyl Glycine and Ivermectin can reduce disease and suppress replication during an ongoing infection.

Experiment 59: Animal Studies of Oral Cyclic Prolyl Glycine and Oral Polio Vaccine Male and female (25-to 28-week-old) mice were genetically deleted for carboxylesterase 1C (Ces1c−/−) (stock 014096, The Jackson Laboratory). Animals were maintained in HEPA-filtered Micro-Isolator® Systems (Lab Products, Inc. Seaford, Delaware, USA). All animal studies and care were conducted in accordance with the Guide for the Care and Use of Laboratory Animals endorsed by the National Institutes of Health. (National Research Council. 2011. Guide for the care and use of laboratory animals, 8th ed. National Academy Press, Washington, DC.).

The recommended method for the titration of viruses is outlined in the WHO Recommendations to Assure the Quality, Safety and Efficacy of Live Attenuated Poliomyelitis Vaccine (oral) (WHO Expert Committee on Biological Standardization: sixty-third report. Geneva: World Health Organization; 2014: Annex 2 (WHO Technical Report Series, No. 980;

http://www.who.int/biologicals/
WHO_TRS_980_WEB.pdf?ua=1, accessed 27 Apr. 2015).).

Briefly, this method is based upon a determination of the cell culture infectious dose ($CCID_{50}$) in Hep2C cell cultures. For estimation of the titre of any sample, replicates were performed to within precision of ±0.5 $\log^{10}$ CCID50/ml or better for the 95% confidence limits of the mean.

The dilutions of vaccine may be made in advance and aliquoted in multiple containers which should be stored at ≤−70° C. The doses for Type 1 serotype for Type 1 of OPV: 2.25 ($\log^{10}$ $CCID_{50}$/5 µl).

The vaccine and reference preparation were diluted with Eagle's minimum essential medium (EMEM) containing 0.14% bovine albumin and 0.22% sodium bicarbonate, and Earle's balanced salt solution containing 0.5% lactalbumin hydrolysate which were by the U. S. Food and Drug Administration.

For each experiment there were initially 8 mice per drug-treated group and placebos. Mice were anesthetized as described above and treated with a 50-µl volume of saline alone (placebo) or saline containing Cyclic Prolyl Glycine (cPG) or and cPG plus Oral Polio Vaccine (OPV). In the treatment drug group, 50-µl volume of cPG (0.2 mg/kg) was administered orally once a day for Day 1 and Day 28. In the treatment vaccine group, 50-µl volume of Oral Polio Vaccine (OPV) at concentration 0.45 ($\log^{10}$ $CCID_{50}$/µl) was administered orally once a day on Day 1, and Day 28. In the group with combination of drug and vaccine treatment, 50-µl volume containing cPG (0.2 mg/kg) and OPV at concentration 0.45 ($\log^{10}$ $CCID_{50}$/µl) were administered orally once a day for Day 1 and Day 28 In the placebo group, 50-µl volume containing saline solution was administered orally once a day on Day 1 and Day 28.

The animals were anesthetized with ketamine/xylazine and infected with 104 PFU/50 ml (prophylactic studies) or 103 PFU/50 ml (therapeutic studies) SARS-CoV MA15. Animals were weighed daily to monitor virus associated weight loss and to determine the appropriate dose volume of drug (Cyclo Prolyl Glycine), drug plus oral polio vaccine and or vehicle.

On day 5 post infection (S dpi) mice were sacrificed and necropsied for analysis of lung parameters (lung hemorrhage scores, weights, and virus titers). The lungs were weighed on a precision balance, followed by freezing at −80° C. for viral titration via plaque assay, as described by Gralinski et al. The inferior right lobe was placedin 10% buffered formalin and stored at 4° C. until histological analysis. Weight loss significance was determined by Student's t test (Microsoft Excel). Aberrations in lung function were determined by WBP (Data Sciences International), as described by Menachery et al.

Figure 74:
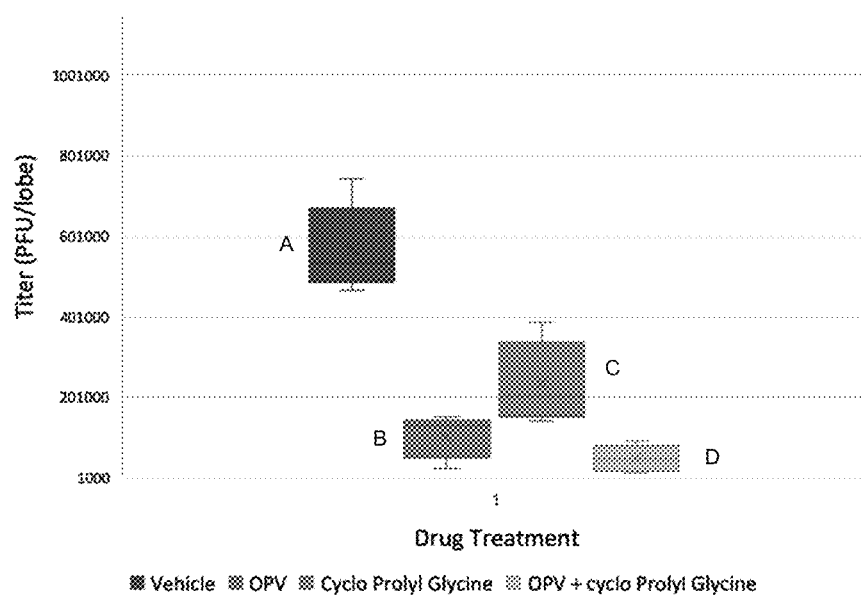

The weight loss studies and lung titers studies of cPG and OPV were summarized in FIG. 73 and FIG. 74, respectively.

The results of the oral administration of cPG and OPV that substantially reduced the SARS-COV-induced weight loss in infected mice, thus demonstrating that combination therapy of cPG and OPV can reduce disease and suppress replication during an ongoing infection. These data suggest that a combination therapy of cPG and OPV can serve as a prophylaxis and treatment that can prevent SARS-CoV and improved pulmonary function as compared to vehicle-treated controls.

The compounds mentioned in the summary section above, and elsewhere herein, can be preliminarily screened by in vitro assays for their efficacy against the replication of SARS-CoV2 virus. Other methods will also be apparent to those of ordinary skill in the art. These compounds can be further screened by in vivo assays.

Pharmaceutical Dosages-Various Embodiments

The co-administration of an antimalarial drug such as artemether and an antiviral drug such as atazanavir is described above as an example and is a non-limiting example of the present invention. Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Generally, administration is affected as long as virus is found in the subject and/or until at least one of the symptoms associated with the disease are alleviated.

In some embodiments of the present invention, the composition is formulated so as to provide a desired overlapping efficacy window of the two agents. This can be achieved by formulating a composition for releasing a desired therapeutically effective amount of each agent (for example, an amount for providing optional synergy) in a controlled manner.

In some embodiments of the present invention, the additional antiviral agent is unsuitable for inclusion in the composition, and as therefore administered separately.

According to some embodiments of the present invention, the therapeutically effective amount of artemether and the therapeutically effective amount of atazanavir are selected such that artemether and atazanavir in optional synergy.

According to some embodiments of the present invention, the therapeutically effective amount of artemether is in a range of from about 50 to about 400 mg per day.

According to some embodiments of the present invention, the therapeutically effective amount of hydroxychloroquine is in a range of from about 200 to about 400 mg per day.

According to some embodiments of the present invention, the therapeutically effective amount of atazanavir sulfate is in a range of from about 100 to about 600 mg per day.

According to some embodiments of the present invention, the therapeutically effective amount of Efavirenz is in a range of from about 50 mg, about 100 mg, about 200 mg, to about 600 mg per day.

According to some embodiments of the present invention, the therapeutically effective amount of Fosamprenavir is in a range of from about 700 mg to about 1,400 mg per day.

According to some embodiments of the present invention, the therapeutically effective amount of Saquinavir is in a range of from about 500 mg to about 1,000 mg per day.

An embodiment of the present invention is a preventive protection for first responders, physicians, nurses and other healthcare workers who are in frequent contact with patients infected with Covid-19. A recommended dosage for prophylaxis application is co-administration of artemether and atazanavir at lower dosage than for treatment for patients in critical condition. For example: Atazanavir is available in capsules of about 150 mg, about 200 mg, and about 300 mg. Artemether is available in the market as in a table form comprising of artemether/lumefantrine (about 20 mg/about 120 mg). A recommended dosage for prophylaxis is one table of artemether/lumefantrine and one about 150 mg capsule of atazanavir per day.

An embodiment of the present invention for treatment of Covid-19 infection is co-administration of up to 4 tablets of artemether/lumefantrine (about 20 mg/about 120 mg), in conjunction with one about 300 mg capsule of atazanavir twice per day, depending on the condition of the patient.

An embodiment of the present invention is a preventive protection for first responders, physicians, nurses and other healthcare workers who are in frequent contact with patients infected with Covid-19. A recommended dosage for prophylaxis application is co-administration of artemether and efavirenz at lower dosage than for treatment for patients in critical condition. A recommended dosage for prophylaxis is one table of artemether/lumefantrine and one about 50 mg capsule of efavirenz per day.

An embodiment of the present invention for treatment of Covid-19 infection is co-administration of up to 4 tablets of artemether/lumefantrine (about 20 mg/about 120 mg), in conjunction with one about 600 mg capsule of efavirenz twice per day, depending on the condition of the patient An embodiment of the present invention is a preventive protection for first responders, physicians, nurses and other healthcare workers who are in frequent contact with patients infected with Covid-19. A recommended dosage for prophylaxis application is co-administration of artemether and fosamprenavir at lower dosage than for treatment for patients in critical condition. A recommended dosage for prophylaxis is one table of artemether/lumefantrine and one about 700 mg tablet of fosamprenavir per day.

An embodiment of the present invention for treatment of Covid-19 infection is co-administration of up to 4 tablets of artemether/lumefantrine (about 20 mg/about 120 mg), in conjunction with one about 700 mg tablet of fosamprenavir twice per day, depending on the condition of the patient.

An embodiment of the present invention is a preventive protection for first responders, physicians, nurses and other healthcare workers who are in frequent contact with patients infected with Covid-19. A recommended dosage for prophylaxis application is co-administration of artemether and saquinavir at lower dosage than for treatment for patients in critical condition. A recommended dosage for prophylaxis is one table of artemether/lumefantrine and one about 500 mg tablet of saquinavir per day An embodiment of the present invention for treatment of Covid-19 infection is co-administration of up to 4 tablets of artemether/lumefantrine (about 20 mg/about 120 mg), in conjunction with one about 1,000 mg tablet of saquinavir twice per day, depending on the condition of the patient.

An embodiment of the present invention is a preventive protection for first responders, physicians, nurses and other healthcare workers who are in frequent contact with patients infected with Covid-19. A recommended dosage for prophylaxis application is co-administration of Remdesivir (GS-5734) and Artemether at lower dosage than for treatment for patients in critical condition. A recommended dosage for prophylaxis is one capsule containing about 40 mg of Artemether and about 50 mg of GS-5734 per day.

An embodiment of the present invention for treatment of Covid-19 infection is co-administration of up to 4 tablets of artemether/lumefantrine (each contains about 20 mg of artemether and about 120 mg lumefantrine), in conjunction with about 200 mg of GS-5734 in intravenous form in the first day twice per day, followed by 4 tablets of artemether/lumefantrine (each contains about 20 mg of artemether/about 120 mg lumefantrine), in conjunction with about 100 mg of GS-5734 in intravenous form for the 7 days, depending on the conditions of the patient.

An embodiment of the present invention for the prevention and treatment of Covid-19 infection is combination therapy of nanoparticle intranasal formulation containing about 10 mg to about 20 mg of Artemether and about 20 mg to about 100 mg of GS-5734 once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 20 mg to about 40 mg of Valsartan once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 10 mg to about 20 mg of Atazanavir once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 0.005 mg/kg to about 0.04 mg/kg of Digoxin once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 7 mg to about 14 mg of Teriflunomide once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 10 mg to about 50 mg of Cyclic Prolyl Glycine once or twice per day, under physician prescription depending on the conditions of the patient.

An embodiment of the present invention for prevention and treatment of Covid-19 infection is combination therapy of oral formulation containing about 10 mg to about 50 mg of Cyclic Prolyl Glycine and about 10 mg to about 20 mg of Atazanavir once or twice per day, under physician prescription depending on the conditions of the patient.

An embodiment of the present invention for prevention and treatment of Covid-19 infection is combination therapy of nanoparticle intranasal formulation containing about 10 mg to about 20 mg of Artemether and about 20 mg to about 100 mg of GS-5734 once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 20 mg to about 40 mg of Valsartan once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 10 mg to about 20 mg of Atazanavir once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 0.005 mg/kg to about 0.04 mg/kg of Digoxin once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 7 mg to about 14 mg of Teriflunomide once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 10 mg to about 50 mg of Cyclic Prolyl Glycine once or twice per day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 0.15 mg to about 1.00 mg/kg of Donepezil once or twice a day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 0.15 mg to about 0.50 mg/kg of Memantine once or twice a day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 0.01 mg to about 0.4 mg/kg of Rivastigmine once or twice a day, under physician prescription depending on the conditions of the patient.

An embodiment of the present invention for prevention and treatment of Covid-19 infection is combination therapy of nanoparticle intranasal formulation containing about 20 mg to about 100 mg of GS-5734 and about 0.20 mg to about 1.00 mg/kg of Galantamine once or twice a day, under physician prescription depending on the conditions of the patient.

An embodiment of the present invention for prevention and treatment of Covid-19 infection is combination therapy of oral formulation containing about 10 mg to about 50 mg of Cyclic Prolyl Glycine and about 7 mg to about 14 mg of Teriflunomide once or twice per day, under physician prescription depending on the conditions of the patient.

An embodiment of the present invention for prevention and treatment of Covid-19 infection by administering to a patient a combination therapy of oral formulation containing about 10 mg to about 50 mg of Cyclic Prolyl Glycine and about 80 to about 160 mg of Valsartan once or twice per day, under physician prescription depending on the conditions of the patient.

An embodiment of the present invention for prevention and treatment of Covid-19 infection is combination therapy of oral formulation containing about 10 mg to about 50 mg of Cyclic Prolyl Glycine and about 0.10 to about 1.00 mg/kg of Donepezil once or twice per day, under physician prescription depending on the conditions of the patient.

An embodiment of the present invention for prevention and treatment of Covid-19 infection is combination therapy of oral formulation containing about 10 mg to about 50 mg of Cyclic Prolyl Glycine and about 0.01 to about 0.10 mg/kg of Rivastigmine once or twice per day, under physician prescription depending on the conditions of the patient.

An embodiment of the present invention for prevention and treatment of Covid-19 infection is combination therapy of oral formulation containing about 10 mg to about 50 mg of Cyclic Prolyl Glycine and about 0.20 mg to about 1.00 mg/kg of Memantine once or twice per day, under physician prescription depending on the conditions of the patient.

An embodiment of the present invention for prevention and treatment of Covid-19 infection is combination therapy of oral formulation containing about 10 mg to about 50 mg of Cyclic Prolyl Glycine and about 0.20 mg to about 1.00 mg/kg of Galantamine once or twice per day, under physician prescription depending on the conditions of the patient.

An embodiment of the present invention for prevention and treatment of Covid-19 infection is combination therapy of oral formulation containing about 10 mg to about 50 mg of Cyclic Prolyl Glycine and about 0.20 mg to about 1.00 mg/kg of Memantine once or twice per day, under physician prescription depending on the conditions of the patient.

An embodiment of the present invention for prevention and treatment of Covid-19 infection is combination therapy of oral formulation containing about 10 mg to about 20 mg of Atazanavir and about 0.10 mg to about 1.00 mg/kg of Donepezil once or twice per day, under physician prescription depending on the conditions of the patient.

An embodiment of the present invention for prevention and treatment of Covid-19 infection is combination therapy of oral formulation containing about 10 mg to about 20 mg of Atazanavir and about 0.01 to about 0.10 mg/kg of Rivastigmine once or twice per day, under physician prescription depending on the conditions of the patient.

An embodiment of the present invention for prevention and treatment of Covid-19 infection is combination therapy of oral formulation containing about 10 mg to about 20 mg of Atazanavir and about 0.20 mg to about 1.00 mg/kg of Memantine once or twice per day, under physician prescription depending on the conditions of the patient.

An embodiment of the present invention for prevention and treatment of Covid-19 infection is combination therapy of oral formulation containing about 10 mg to about 20 mg of Atazanavir and about 0.20 mg to about 1.00 mg/kg of Galantamine once or twice per day, under physician prescription depending on the conditions of the patient.

An embodiment of the present invention for prevention and treatment of Covid-19 infection is combination therapy of oral formulation containing about 10 mg to about 20 mg of Atazanavir and about 80 to about 160 mg of Valsartan once or twice per day, under physician prescription depending on the conditions of the patient.

An embodiment of the present invention for prevention and treatment of Covid-19 infection is combination therapy of oral formulation containing about 10 mg to about 20 mg of Atazanavir and about 7 to about 14 mg of Teriflunomide once or twice per day, under physician prescription depending on the conditions of the patient.

An embodiment of the present invention for prevention and treatment of Covid-19 infection is combination therapy of oral formulation containing about 1 to about 6 mg of Dexamethasone and about 10 to about 50 mg of Cyclic Prolyl Glycine once or twice per day, under physician prescription depending on the conditions of the patient.

An embodiment of the present invention for prevention and treatment of Covid-19 infection is combination therapy of oral formulation containing about 1 to about 6 mg of Dexamethasone and about 0.15 mg to about 1.00 mg/kg of Donepezil once or twice per day, under physician prescription depending on the conditions of the patient An embodiment of the present invention for prevention and treatment of Covid-19 infection is combination therapy of oral formulation containing about 1 to about 6 mg of Dexamethasone and about 10 to about 20 mg of Atazanavir once or twice per day, under physician prescription depending on the conditions of the patient An embodiment of the present invention for prevention and treatment of Covid-19 infection is combination therapy of nanoparticle intranasal formulation containing about 1 to about 6 mg of Dexamethasone and about 20 mg to about 100 mg of GS-5734 once or twice a day, under physician prescription depending on the conditions of the patient.

An embodiment of the present invention for prevention and treatment of Covid-19 infection is combination therapy of oral formulation containing about 8 to about 48 mg of Methylprednisolone and about 10 to about 50 mg of Cyclic Prolyl Glycine once or twice per day, under physician prescription depending on the conditions of the patient.

An embodiment of the present invention for prevention and treatment of Covid-19 infection is combination therapy of oral formulation containing about 8 to about 48 mg of Methylprednisolone and about 0.15 mg to about 1.00 mg/kg Donepezil once or twice per day, under physician prescription depending on the conditions of the patient.

An embodiment of the present invention for prevention and treatment of Covid-19 infection is combination therapy of oral formulation containing about 1 to about 6 mg of Dexamethasone and about 7-14 mg of Teriflunomide once or twice per day, under physician prescription depending on the conditions of the patient.

An embodiment of the present invention for prevention and treatment of Covid-19 infection is combination therapy of oral formulation containing about 8 to about 48 mg of Methylprednisolone and about 7 to about 14 mg of Teriflunomide once or twice per day, under physician prescription depending on the conditions of the patient.

An embodiment of the present invention for prevention and treatment of Covid-19 infection is combination therapy of oral formulation preferably containing about 10 mg to about 50 mg of Cyclic Prolyl Glycine and about 0.4 mg/kg of Ivermectin once or twice per day, under physician prescription depending on the conditions of the patient.

An embodiment of the present invention is a preventive protection for first responders, physicians, nurses and other healthcare workers who are in frequent contact with patients infected with Covid-19. A recommended dosage for prophylaxis application is co-administration of about 10 to about 50 mg of Cyclic Prolyl Glycine(oral) and Oral Polio Vaccine at an average dose of about 0.45 ($\log^{10}$ $CCID_{50}/\mu l$ on Day 1 and on Day 28. It is recommended that a second vaccination to be carried 28 days after the initial vaccination.

Pharmaceutical compositions are well known in the medical arts and can include formulations in solid form such as a tablet to be administered orally. Formulations of the present invention can also include liquid, gel, semisolid, colloidal, vapor and gas phase formulations capable of oral, nasal, bronchial, intestinal, or colonic (anal and perianal) delivery. In one embodiment, the compositions of the present invention are administered mucosally (for example, to the mucosa of the subject). By mucosa is meant anybody mucosa including oral, nasal, bronchial, esophageal, intestinal, and anal or perianal.

It will be recognized to the skilled clinician, choice of a carrier, including a physiologically acceptable compound, depends, for example, on the manner in which the peptide or encoding polynucleotide is to be administered, as well as on the route of administration of the composition and its dose. Where the composition is administered under immunizing conditions, for example, as a vaccine, it generally is administered intramuscularly, intradermally, or subcutaneously, but also can be administered parenterally such as intravenously, and can be administered by injection, intubation, or other such method known in the art. Where the desired modulation of the immune system is tolerization, the composition preferably is administered orally, or can be administered as above.

The term "therapeutically effective amount" or "effective amount" means the amount of a compound or pharmaceutical composition that will elicit the biological or medical response of a tissue, system, animal or human that is being sought by the researcher, veterinarian, medical doctor or other clinician. Thus, the total amount of a composition to be administered in practicing a method of the present invention can be administered to a subject as a single dose, either as a bolus or by infusion over a relatively short period of time, and can be followed up with one or more booster doses over a period of time. The amount of the composition to stimulate an immune response in a subject depends on various factors including the age and general health of the subject, as well as the route of administration and the number of treatments to be administered. In view of these factors, the skilled clinician will know to adjust the particular dosage as necessary.

The total amount of a compound or composition to be administered in practicing a method of the present invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the compositions of the present invention to treat SARS in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

All of the compositions and methods disclosed and claimed herein can be made and executed without undue experimentation in light of the present disclosure. While the compositions and methods of the present invention have been described in terms of preferred embodiments, it will be apparent to those of skill in the art that variations may be applied to the compositions and methods and in the steps or in the sequence of steps of the method described herein without departing from the spirit and scope of the present invention. More specifically, the described embodiments are to be considered in all respects only as illustrative and not restrictive. All similar substitutes and modifications apparent to those skilled in the art are deemed to be within the spirit and scope of the present invention as defined by the appended claims.

Alternatively, or additionally, additional antiviral agent may optionally be unsuitable for the frequency of administration of the composition, for example, wherein the composition is formulated for administration once per day, and the additional antiviral agent is more suitable for administration once per week (for example, a PEGylated interferon-alpha).

The composition may be, for example, in the form of a liquid, a semi-solid (for example, gel), or solid.

In some embodiments of the present invention, the composition is in a solid form. Examples of solid forms for a composition include, without limitation, a tablet, a capsule (for example, comprising an encapsulated solid), a caplet, a powder, microspheroids, and granules.

The composition is preferably formulated in accordance with the intended frequency of administration of the composition. This, in turn, will depend on the properties of the active agents. As discussed herein, artemether and atazanavir may be administered, for example, once per day, but also at other frequencies (for example, twice or thrice a day).

It is to be appreciated that an active agent can be made more suitable for less frequent administration (for example, once per day, as is particularly convenient, instead of twice or more per day) by formulating a composition appropriately, for example, by formulating the composition for slow release of the active agents therein.

Slow release preparations typically include slow release biodegradable carriers. Slow release biodegradable carriers are well known in the art. These are materials that may form particles that may capture therein an active compound(s) and slowly degrade/dissolve under a suitable environment (for example, aqueous, acidic, basic, etc.) and thereby degrade/dissolve in body fluids and release the active compound(s) therein. The particles are preferably nanoparticles (for example, in the nanometer range, for example, in the range of about 1 to about 500 nm in diameter, preferably about 50 to about 200 nm in diameter, most preferably about 100 nm in diameter).

Oral slow-release forms are often designed to maintain therapeutic drug concentrations for greater than 12 hours. The absorption rate can be controlled by coating drug particles with wax or other water-insoluble material, by embedding the drug in a matrix from which it is released slowly during transit through the GI tract, or by complexing the drug with ion-exchange resins.

Thus, for example, a slow-release formulation in tablet form, can be based on the use of a hydrophilic polymer which swells in contact with gastrointestinal fluids, to form a gel, which creates a barrier that enrobes the tablet. The barrier limits physical exchanges between the inside of the tablet and the surrounding medium. As a consequence, intrusion of water towards the tablet matrix and diffusion of drug are slowed down, allowing a controlled slow release of the drug.

Various types of polymers may be used as a matrix for the slow-release of drugs, such as polyvinyl chloride, polyethylene polyamides, ethylcellulose, silicone, poly (hydroxyethyl methacrylate), other acrylic co-polymers, and polyvinylacetate-polyvinyl chloride copolymers.

In some embodiments of the present invention, the composition is a unit dosage form (for example, a unit dosage form formulated for oral administration).

Pharmaceutical compositions can be administered by an appropriate route of administration at an appropriate dose and an appropriate regime.

Pharmaceutical compositions for use in accordance with embodiments of the present invention thus may be formulated in conventional manner using one or more pharmaceutically acceptable carriers comprising excipients and auxiliaries, which facilitate processing of the active ingredients (artemether and antiviral agents described herein) into preparations which, can be used pharmaceutically. Proper formulation is dependent upon the route of administration chosen.

For injection, the active ingredient(s) of embodiments of the present invention may be formulated in aqueous solutions, preferably in physiologically compatible buffers such as Hank's solution, Ringer's solution, or physiological saline buffer with or without organic solvents such as propylene glycol, polyethylene glycol.

For oral administration, the active ingredients can be formulated readily by combining the active ingredients described herein with pharmaceutically acceptable carriers well known in the art. Such carriers enable the active ingredient(s) to be formulated as tablets, pills, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients described herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

The active ingredients described herein can be formulated for parenteral administration, for example, by bolus injection or continuous infusion. Formulations for injection may be presented in unit dosage form, for example, in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredients.

Additionally, suspensions of the active ingredients may be prepared as appropriate oily injection suspensions and emulsions (for example, water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredients may be in powder form for constitution with a suitable vehicle, for example, sterile, pyrogen-free water, before use.

The active ingredients of embodiments of the present invention may also be formulated in rectal compositions such as suppositories or retention enemas, using, for example, conventional suppository.

For administration by inhalation, the active ingredient(s) for use according to embodiments of the present invention are conveniently delivered in the form of an aerosol spray presentation (which typically includes powdered, liquefied and/or gaseous carriers) from a pressurized pack or a nebulizer, with the use of a suitable propellant, for example, dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, for example, gelatin for use in an inhaler or insufflator may be formulated containing a powder mix of the active ingredient(s) and a suitable powder base such as, but not limited to, lactose or starch.

The choice of drug delivery methods requires understanding of tissue distribution, metabolism and cellular effects as well as an understanding of the interaction of the drug with the specific underlying pathological processes of the disease under treatment, for which general and specific teaching are available in the art.

Because the route of drug administration determines bioavailability and tissue levels and distribution, change in delivery may modify fundamentally the location, nature, extent and duration of disease condition, as well as alter dosing requirements and toxicities.

However, it was observed that when artemether is administered locally via nasal delivery system in vivo, the drug was adsorbed quickly with more bioavailability and short duration of action in treating the fever very quickly than when administered systemically.

In the treatment of Covid-19, there is believed to be a window of opportunity within 3-5 days in which the coronavirus spreads can be effectively slowed down to enable the body immune system to fight back. Most patients are admitted to hospital after several days of developing obvious symptoms including fever, coughing and hard to breathe. By that time, it is difficult to treat effectively. It is desirable that the patient receive medications to control fever and severe respiratory conditions immediately. The oral administration of drugs might not provide sufficient bioavailability quick enough to stop the destruction of the Covid-19. In critical care cases, it is recommended that the patient to receive a combination of an antiviral and antimalarial drug via inhalation rapid absorption that will reach to the disease area rapidly.

Specifically, the present invention provides a method for treating severe acute respiratory syndrome (SARS) and Covid-19 condition, especially in the pulmonary system, comprising administering via localized delivery to an area of inflammation in a subject in need thereof an anti-inflammatory effective amount of an anti-malarial and an antiviral drug compound. An example of a particular application of the method of the present invention is treatment of Covid-19 by inhalation of to an aerosolized anti-malarial and antiviral drug compound. The method of the invention unexpectedly shows a rapid, therapeutic effect compared to systemic administration.

For pulmonary delivery, a therapeutic composition of the invention can be formulated and administered to the patient in solid or liquid particulate form by direct administration for example, inhalation into the respiratory system.

Solid or liquid particulate forms of the active compound prepared for practicing the present invention include particles of respirable size: that is, particles of a size sufficiently small to pass through the mouth and larynx upon inhalation and into the bronchi and alveoli of the lungs. In general, particles ranging from about 1 to about 10 microns in size are within the general respirable range. The therapeutic composition containing the anti-malarial and antiviral compounds are preferably administered by direct inhalation into the respiratory system for delivery as a mist or other aerosol or dry powder.

The dosage of active compound via this route may vary depending on the condition being treated and the state of the subject, but generally may be an amount sufficient to achieve dissolved concentrations of anti-malarial and antiviral compound on the airway surfaces of the subject. Depending upon the solubility of the particular formulation of active compound administered, the daily dose may be divided among one or several unit dose administrations. The daily dose administered via direct inhalation is normally much less than oral dose. For example, a daily dose of artemether administered via direct inhalation ranges from 20 to 40 mg per day and Atazanavir from about 25 mg to about 100 mg per day. The doses of the active compounds can be provided as one or several prepackaged units.

Aerosols of liquid particles comprising the anti-malarial and antiviral compounds can be produced by any suitable means, such as inhalatory delivery systems. One is a traditional nebulizer which works in a mechanism similar to the familiar perfume atomizer. The airborne particles are generated by a jet of air from either a compressor or compressed gas cylinder-passing through the device (pressure driven aerosol nebulizer) (U.S. Pat. No. 4,501,729-"Aerosolized amiloride treatment of retained pulmonary secretions").

While various embodiments of the present invention have been described above, it should be understood that they have been presented by way of examples only, and not limitation. It will be understood by those skilled in the art that various changes in form and detail may be made therein without departing from the spirit and scope of the present invention as defined in the appended claims. Thus, the breadth and scope of the present invention should not be limited by any of the above-described exemplary embodiments, but should be defined in accordance with the following claims and their equivalents.

The present invention is described with reference to specific embodiments thereof. Other features and embodiments of the present invention can be produced by those of skill in the art without undue experimentation and a reasonably likelihood of success. All of those and other embodiments are considered to be part of the present invention.

All publication, including patent documents and scientific articles, referred to in this application, including any bibliography, are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A method of prophylaxis or treatment of severe acute respiratory syndrome caused by SARS-CoV2, comprising:
   a. providing a subject in need of said prophylaxis or treatment of severe acute respiratory syndrome caused by SARS-CoV2;
   b. providing at least one pharmaceutical composition comprising one or more of the following components:
      1) at least one cPG compound;
      2) donepezil; or
      3) a combination thereof;
      wherein said components are administered together or separately; and
      further wherein said components are provided in a pharmaceutically acceptable diluent, adjuvant, excipient, or a combination thereof;
   c. administering a pharmaceutically effective amount of said at least one pharmaceutical composition to said subject;
wherein said subject is provided prophylaxis or treatment of severe acute respiratory syndrome caused by SARS-CoV2.

2. The method of claim 1, wherein said prophylaxis or treatment of severe acute respiratory syndrome caused by SARS-CoV2 addresses high lung viral titer, weight loss, acute respiratory distress syndrome, impaired pulmonary function, acute lung injury, fever, coughing, severe respiratory conditions, or a combination thereof.

3. The method of claim 1, wherein said severe acute respiratory syndrome caused by SARS-CoV2 comprises high lung viral titer.

4. The method of claim 1, wherein said severe acute respiratory syndrome caused by SARS-CoV2 comprises weight loss.

5. The method of claim 1, wherein said severe acute respiratory syndrome caused by SARS-CoV2 comprises acute lung injury.

6. The method of claim 1, wherein said at least one pharmaceutical composition comprising at least one nanoparticle formulation.

7. The method of claim 6, wherein said at least one nanoparticle formulation comprises chitosan.

8. The method of claim 1, wherein said at least one cPG compound comprises Cyclic Prolyl Glycine, Cyclic Glycyl-2-Allyl Proline, Cyclic (glycyl-L-prolylglycyl-L-prolylglycyl-L-prolyl), or a combination thereof.

9. The method of claim 8, wherein said at least one cPG compound comprises Cyclic Prolyl Glycine.

10. The method of claim 9, wherein said Cyclic Prolyl Glycine is provided in a dose of about 10 mg to about 50 mg.

11. The method of claim 9, wherein said Cyclic Prolyl Glycine is provided in a dose of about 0.1 to about 1.0 mg/kg.

12. The method of claim 9, wherein said Cyclic Prolyl Glycine is administered once a day, twice a day, or a combination thereof.

13. The method of claim 9, wherein said Cyclic Prolyl Glycine is administered orally, intranasally, or a combination thereof.

14. The method of claim 8, wherein said at least one cPG compound comprises Cyclic Glycyl-2-Allyl Proline.

15. The method of claim 14, wherein said Cyclic Glycyl-2-Allyl Proline is provided in a dose of about 20 mg to about 60 mg.

16. The method of claim 14, wherein said Cyclic Glycyl-2-Allyl Proline is provided in a dose of about 0.1 to about 1.0 mg/kg.

17. The method of claim 14, wherein said pharmaceutical composition comprising Cyclic Glycyl-2-Allyl Proline is administered once a day, twice a day, or a combination thereof.

18. The method of claim 14, wherein said pharmaceutical composition comprising Cyclic Glycyl-2-Allyl Proline is administered orally, intranasally, or a combination thereof.

19. The method of claim 8, wherein said at least one cPG compound comprises Cyclic (glycyl-L-prolylglycyl-L-prolylglycyl-L-prolyl).

20. The method of claim 19, wherein said pharmaceutical composition comprises Cyclic (glycyl-L-prolylglycyl-L-prolylglycyl-L-prolyl) is provided in a dose of about 30 mg to about 100 mg.

21. The method of claim 19, wherein said pharmaceutical composition comprises Cyclic (glycyl-L-prolylglycyl-L-prolylglycyl-L-prolyl) is provided in a dose of about 0.1 to about 2.0 mg/kg.

22. The method of claim 19, wherein said pharmaceutical composition comprising Cyclic (glycyl-L-prolylglycyl-L-prolylglycyl-L-prolyl) is administered once a day, twice a day, or a combination thereof.

23. The method of claim 19, wherein said pharmaceutical composition comprising Cyclic (glycyl-L-prolylglycyl-L-prolylglycyl-L-prolyl) is administered orally, intranasally, or a combination thereof.

24. The method of claim 1, wherein said pharmaceutical composition comprises donepezil.

25. The method of claim 24, wherein said donepezil is provided in a dose of about 0.1 to about 0.50 mg/kg.

26. The method of claim 24, wherein said donepezil is administered once a day, twice a day, or a combination thereof.

27. The method of claim 24, wherein said donepezil is administered orally, intranasally, or a combination thereof.

28. The method of claim 1, wherein said prophylaxis or treatment further comprises neuroprotection.

29. The method of claim 28, wherein said neuroprotection is mediated by said at least one cPG compound.

30. The method of claim 1, wherein said prophylaxis or treatment of severe acute respiratory syndrome caused by SARS-CoV2 is prophylaxis.

31. The method of claim 1,
wherein said prophylaxis or treatment of severe acute respiratory syndrome caused by SARS-CoV2 is treatment.

32. A method of prophylaxis or treatment of severe acute respiratory syndrome caused by SARS-CoV2, comprising:
a. providing a subject in need of said prophylaxis or treatment of severe acute respiratory syndrome caused by SARS-CoV2;
b. providing at least one pharmaceutical composition comprising the following components:
1. At least one cPG compound;
wherein said components are administered together or separately; and
further wherein said components are provided in a pharmaceutically acceptable diluent, adjuvant, excipient, or a combination thereof;
c. administering a pharmaceutically effective amount of said at least one pharmaceutical composition to said subject;
wherein said subject is provided prophylaxis or treatment of severe acute respiratory syndrome caused by SARS-CoV2.

33. The method of claim 32,
wherein said prophylaxis or treatment of severe acute respiratory syndrome caused by SARS-CoV2 addresses high lung viral titer, weight loss, acute respiratory distress syndrome, impaired pulmonary function, acute lung injury, fever, coughing, severe respiratory conditions, or a combination thereof.

34. The method of claim 12,
wherein said severe acute respiratory syndrome caused by SARS-CoV2 comprises high lung viral titer.

35. The method of claim 32,
wherein said severe acute respiratory syndrome caused by SARS-CoV2 comprises weight loss.

36. The method of claim 32,
wherein said severe acute respiratory syndrome caused by SARS-CoV2 comprises acute lung injury.

37. The method of claim 32,
wherein said at least one pharmaceutical composition comprising at least one nanoparticle formulation.

38. The method of claim 37,
wherein said at least one nanoparticle formulation comprises chitosan.

39. The method of claim 32,
wherein said at least one cPG compound comprises Cyclic Prolyl Glycine, Cyclic Glycyl-2-Allyl Proline, Cyclic (glycyl-L-prolylglycyl-L-prolylglycyl-L-prolyl), or a combination thereof.

40. The method of claim 39,
wherein said at least one cPG compound comprises Cyclic Prolyl Glycine.

41. The method of claim 40,
wherein said Cyclic Prolyl Glycine is provided in a dose of about 10 mg to about 50 mg.

42. The method of claim 20,
wherein said Cyclic Prolyl Glycine is provided in a dose of about 0.1 to about 1.0 mg/kg.

43. The method of claim 40,
wherein said Cyclic Prolyl Glycine is administered once a day, twice a day, or a combination thereof.

44. The method of claim 40,
wherein said Cyclic Prolyl Glycine is administered orally, intranasally, or a combination thereof.

45. The method of claim 39,
wherein said at least one cPG compound comprises Cyclic Glycyl-2-Allyl Proline.

46. The method of claim 45,
wherein said Cyclic Glycyl-2-Allyl Proline is provided in a dose of about 20 mg to about 60 mg.

47. The method of claim 45,
wherein said Cyclic Glycyl-2-Allyl Proline is provided in a dose of about 0.1 to about 1.0 mg/kg.

48. The method of claim 45,
wherein said pharmaceutical composition comprising Cyclic Glycyl-2-Allyl Proline is administered once a day, twice a day, or a combination thereof.

49. The method of claim 45,
wherein said pharmaceutical composition comprising Cyclic Glycyl-2-Allyl Proline is administered orally, intranasally, or a combination thereof.

50. The method of claim 39,
wherein said at least one cPG compound comprises Cyclic (glycyl-L-prolylglycyl-L-prolylglycyl-L-prolyl).

51. The method of claim 50,
wherein said pharmaceutical composition comprises Cyclic (glycyl-L-prolylglycyl-L-prolylglycyl-L-prolyl) is provided in a dose of about 30 mg to about 100 mg.

52. The method of claim 50,
wherein said pharmaceutical composition comprises Cyclic (glycyl-L-prolylglycyl-L-prolylglycyl-L-prolyl) is provided in a dose of about 0.1 to about 2.0 mg/kg.

53. The method of claim 50,
wherein said pharmaceutical composition comprising Cyclic (glycyl-L-prolylglycyl-L-prolylglycyl-L-prolyl) is administered once a day, twice a day, or a combination thereof.

54. The method of claim 50,
wherein said pharmaceutical composition comprising Cyclic (glycyl-L-prolylglycyl-L-prolylglycyl-L-prolyl) is administered orally, intranasally, or a combination thereof.

55. The method of claim 32,
wherein said prophylaxis or treatment further comprises neuroprotection.

56. The method of claim 55,
wherein said neuroprotection is mediated by said at least one cPG compound.

57. The method of claim 32,
wherein said prophylaxis or treatment of severe acute respiratory syndrome caused by SARS-CoV2 is prophylaxis.

58. The method of claim 32,
wherein said prophylaxis or treatment of severe acute respiratory syndrome caused by SARS-CoV2 is treatment.

* * * * *